(12) United States Patent
Ohlrogge et al.

(10) Patent No.: US 7,868,156 B2
(45) Date of Patent: *Jan. 11, 2011

(54) PLANT SEED SPECIFIC PROMOTERS

(75) Inventors: John B. Ohlrogge, Okemos, MI (US);
Christoph Benning, East Lansing, MI (US); Hongbo Gao, East Lansing, MI (US); Thomas Arno Alfred Girke, Poway, CA (US); Joseph A. White, Gaithersburg, MD (US)

(73) Assignee: Board of Trustees of Michigan State University, East Lansing, MI (US)

( * ) Notice: Subject to any disclaimer, the term of this patent is extended or adjusted under 35 U.S.C. 154(b) by 200 days.

This patent is subject to a terminal disclaimer.

(21) Appl. No.: 12/172,832

(22) Filed: Jul. 14, 2008

(65) Prior Publication Data

US 2009/0100551 A1 Apr. 16, 2009

Related U.S. Application Data

(63) Continuation of application No. 11/488,274, filed on Jul. 18, 2006, now Pat. No. 7,405,345, which is a continuation of application No. 09/998,059, filed on Nov. 30, 2001, now Pat. No. 7,081,565.

(60) Provisional application No. 60/250,401, filed on Dec. 1, 2000.

(51) Int. Cl.
C07H 21/04 (2006.01)
C12N 5/10 (2006.01)
C12N 15/82 (2006.01)
A01H 5/10 (2006.01)
A01H 5/00 (2006.01)

(52) U.S. Cl. .................. 536/24.1; 435/320.1; 435/419; 435/468; 800/287; 800/298

(58) Field of Classification Search .................. None
See application file for complete search history.

(56) References Cited

PUBLICATIONS

Bevan et al., GenBank Acc. No. AL021749, Aug. 3, 1999.*
Lin et al., GenBank Acc. No. AC006587, Mar. 23, 1999.*

* cited by examiner

Primary Examiner—Ashwin Mehta
(74) Attorney, Agent, or Firm—Medlen & Carroll, LLP

(57) ABSTRACT

The present invention relates to novel seed specific promoter regions. The present invention further provide methods of producing proteins and other products of interest and methods of controlling expression of nucleic acid sequences of interest using the seed specific promoter regions. The present invention also provides methods of identifying and isolating novel seed specific promoters.

9 Claims, 25 Drawing Sheets

Promoter 01

```
-1161  CACAAACATA CACTCAAAAT CCAGACTCAC ATCTACTCAA TTATGCAACT
-1111  TCATCATGAA AACATCAAAA ACAGTCAAAG TAACAAAATC AAGTCAGATT
-1061  CAGCACACAA AGCCAGTAAA GATAGAAAAT TTAACGAACG CTCATGCTAA
-1011  GCTGCGCAAA ATACTTCCTA ATCAAACAG  TAACAACGAG TAATTAGCAA
- 961  AATCCGAGCA GAAACTCTC  ACCCACCTCC GAAATTCACG TCTTCACTAA
- 911  AATTTTCGAA AGGAATCGAT CAATACCAAC CCATTACACA AAATACATAA
- 861  TCAAAATGGC GAGAATCGTA CCTGGAAACT TGCTTCAAG  TCGCAGAGAG
- 811  AGGAAAAGGA AGATCGTGGA GAAGGGGTT  TAGGGTTTAA GCTCAGACTT
- 761  CTATTGGAGT AAATGGGACG GTGTCACATT TTCCGTTTTG GAAATGAACT
- 711  TTGGGCTCAC GTTATGGGCT ATTAGATATT TGATGGGCTT TCTAGTAAAT
- 661  ACAATATAAG TTATTGGGCT TAGTTTAAAT AAGCCCATGT TGGAAATATT
- 611  TGACACATGT CTTGGCTACT AGTGCTAAAC ATGCAACCGA ACAGTTGTCG
- 561  AGACAAGTCG CAGCATATAC AATGGATCAA ACACGCCTAG TGTCGCCGCG
- 511  TCTCGCTCAT GTGTCACCTT GTTCCTCGT  TTTTTTTTAA TTTTTCATAA
- 461  GTTCTTTTGT TTTATCTTCA ATACAAATTT TTGGCTGTAT CTTGCAAACT
- 411  CTTCGATCAT ATCGCCAATA TACGTGAACA CTGGTGATCT AATTTGTTGT
- 361  GTTAATTGTT AAATTTAGAT TCTATTCTCC GGTTTAAAAG TGAATTATAT
- 311  GTATCATGGT TAAAACATTG TAAGTAAGAT GATAATAAAA TGATAAATTT
- 261  AGTTGATGGA TAACGTGAAG CAAAAAATGA GATAGATACA TTTGATTTTG
- 211  TCGTATTTTG ACATATGCGG AGAGTGAGCT ACGCGCATGA AGATCAAGAG
- 161  ACACTTGCTC GAGCTCACAG AGTGACGTGT AAAAAGCTTA GACTGAAGTC
- 111  CCCATGCAAA CCTAATCCTA CGTGGCTCAA ACCACGAGCT CACTTGACAA
-  61  TATATAAACT CCTCCTAAGT CCCGTTCTCT TCATCCATCT CTCACAACAA
-  11  ACAAAAAG   -4

-   3  AAAATG
```

Figure 1

Promoter 03

```
-1148 CAAGAGTGTA AAACGTACCG ATCAAATGTC TTTATAAAAA AAACGTGTTG
-1098 ATGTTGTTCT GTGAATACAA TTAGTTCTGG TTAACAGCTG GTCGACCATT
-1048 TTCTGATGAG AATTTATGTA AGGCCATTGC TCTGGTGTTG AGAAGGTTTA
- 998 GTTTGGTTCA AGCTAACCGT GGTTAGAAAG TTAGAATATA ATGTGTTTCT
- 948 TGATCAGTGA TATCGATCGG ATTTGTATTA TTCATATTGT TTACTCTTTG
- 898 AGTAATTCAT AGTGGTAACT CTTTTTTTTT TTTTTTTTT TTCATATTGG
- 848 TAACTCTTTG AAATGAAAAA CATAGCTAAG AATTGCTAGC TTTGATTTAG
- 798 TCGAGACGTA CGAACTCTCG ATTTGGTTT TTGATTTGTT GGTGTAAAAC
- 748 TCTCGATATT CATAACTCGT AAGATTTGT ACGTATCATC TTCTTATTCT
- 698 CTTCATCGCT CTGTTTTCAA TTTTATGTCA AAACATGGTT TTGGTAATTT
- 648 CTTTTACTCC TACTTCACGG TTTGAGTTAT AATTTTTTG GTAAACCCTT
- 598 AACCACGAGT TTTGATGTAT TTTGACACCT CTAATTATGT GTGTATACGT
- 548 ACACATATAA TTCGGTATTT TCTTAACATA TATATCCCTC ATAAAAATTT
- 498 CTTACATGCA TTGTTCGTGA GTGACCCGTT AATATATATA TTGATAGATA
- 448 CTCTTATAAA ATTATATTCT AAATTTCAGA TTAAGCTGGC ACAACTATAT
- 398 TTCCAACATC ACTAGCTACC ATCAAAAGAT TGACTTCTCA TCTTACTCGA
- 348 TTGAAACCAA ATTAACATAG GGTTTTTATT TAAATAAAAG TTTAACCTTC
- 298 TTTTTAAAAA ATTGTTCATA GTGTCATGTC AGAACAAGAG CTACAAATCA
- 248 CACATAGCAT GCATAAGCGG AGCTATGATG AGTGGTATTG TTTTGTTCGT
- 198 CACTTGTCAC TCTTTTCCAA CACATAATCC CGACAACAAC GTAAGAGCAT
- 148 CTCTCTCTCT CCACACACAC TCATGCATGC ATGCATTCTT ACACGTGATT
-  98 GCCATGCAAA TCTCCTTTCT CACCTATAAA TACAAACCAA CCCTTCACTA
-  48 CACTCTTCAC TCAAACCAAA ACAAGAAAAC ATACACAAAT AGCAAAAC -1

1 ATGGCTA
```

Figure 2

Promoter 04

```
-1037  CAAACCATTG  TTTACACGTC  AATTTGAATT  GCGTCAAATA  TTCGACTGGA
- 987  ATCCTACAAC  ATATTTCTTC  TATTATATCA  ATAGGAAGCA  ACGAACGTTC
- 937  ACATGAAGCC  ATGCAAAAAC  AAATTGAGAA  AAAAAATCAG  AAAATTTATG
- 887  ACAAGTGGTC  TTGCTTCTTA  TACTACGTCG  TGAATGGATG  GTAATAAACA
- 837  ATTAAATGTT  ACCTCTAGTT  TTTTTTTTTT  GAGAGAATGG  TTTTTATCCG
- 787  TATATGGCTT  ATTACAAGTT  TCCTCCTTTT  TCGAGTTTGG  TTTGAGGTCT
- 737  ATATTGAAGA  TGAGATACTA  AAAATTGAGG  TAAATTCTTT  AGTGTGAAGG
- 687  AAAATTAGTA  AATACGATAC  GTTTGGAATT  GTTTACTACT  AAAAAAAAAA
- 637  TTGTTTTAGA  CCAAGCCAGT  CCGACAAAAA  GGCGTGTGAA  TCATAAGAAG
- 587  TATCACATGA  TGCTAGACAT  AAAAGATTTT  TCAAACATGA  CAAAACAAAT
- 537  TGTGAGTGTC  TTAGTCATGC  CATTTGAAGT  AGAACGAAAC  TTAGTGATGA
- 487  GACACGTAAC  ATCAGTGAGA  ATCAAGATCT  AACTTCGGAC  TTATCGTACG
- 437  TACCACGTCC  ACCTAAGTGT  TATCCATATC  TACTACATGT  CTATCTTCAT
- 387  TCAATTTTTT  TTTTGCATTA  ACTTGTAAAC  ATAGTGCATA  ATAATTAGAA
- 337  TCAAGATTTG  AATCCAATTC  GCTTACTAAA  TCCTAAATGT  TAAAAGCATA
- 287  CATGTTTTTC  AAATCCTACT  TTTAGGTGCT  AAGTTTTTTT  TCTAAGGTAG
- 237  TTAGAGATTG  TTAGATTTTA  TATCATTGAA  CTGATCATCA  GTCTCTATAC
- 187  TAACTTCTAG  ATCTCATTGA  ATGTTACTC   AATTTTTTTT  AATTTTTTGT
- 137  TTGGATAATC  GTCTGCTCGT  GGTTTTGATG  CGTACGAACA  CTCGTCACCA
-  87  TGCATGTCAA  GCTCTCCTTC  CTATATAAAC  TAAAACCACC  CATTATTGTC
-  37  CTCAAAAACA  AACACATCAA  CAAAACAACA  AG   -6

-   5  AAAAAATG
```

Figure 3

Promoter 06

```
-1413  CTAAACGAGT  AAAGTTTAGC  ACGATTGAGA  CCACACTGAC  CCATAGCAGT
-1363  CCAATGAGCT  ACGGAAGGCC  TAGGGCTTGA  GGCTTGATGA  GCGCGTGGTG
-1313  GAATAGCGTT  TGAATCTAAA  GTTCGGTTTG  GTACGACTTG  TAATATGAAA
-1263  TAATAATGTA  CAAAGAAGTT  CTACGCTTAA  GGGAACTGTT  TTGTTTTGAG
-1213  CTTTGTATTA  GGACGTCTAG  TGTACAACAA  CGAACGTCGT  GTATAAGCGA
-1163  TCGTTGACTC  TGCACATGTA  ACTCTTTCCT  GAATAAAAAA  TCTTTAAGTC
-1113  TTTAATTTCT  ACATCTTTTA  GGATTATATA  AACGTTACTA  TATAAATAAA
-1063  AAAGAAAAAA  AAATCAGTTC  ACTAACATGC  GAGACTTTGG  GCTAAATATA
-1013  GTGATTCCAA  AGAAAATGAG  TTATAATATT  AATTAATATA  AAGCTCATTT
- 963  TCTTTGGAAT  ATCGTTATAA  GAATATTTTA  ACTTGGATAT  AACTGGGCTT
- 913  ACGCCATTTG  CATCTCGAGG  ATTTTTTGTT  TTTGTTTTTG  TTTTTTTAAT
- 863  ACATTCTCGC  ACTTACACAC  TAAAAATCAT  AATGATCTTC  TTAATTCTTT
- 813  AGCGGAACCA  CCAATTAATC  TTTTTATTAA  GAACTTTATT  ACTTATTTCA
- 763  CTTATTTGTG  CATACGTGCA  TTATTTGGC   AGTAACAAAT  ATCGCGTTAT
- 713  ATATACTGAA  ATCCGGACGC  ATTAATAATA  GGGATATGAT  TATATGAACC
- 663  ACTATCTAGC  TTTGGTAGAA  ACCCAATTAT  AATCAAATAA  TTTACCATTA
- 613  TTGAATAAAT  TAGGCTATAT  AAGTTCATTA  ATAGATGCTA  TAGGTTTTTC
- 563  TTACAAGGCA  CACATTTGAT  TGTTATTTTC  TTTCATATAC  ACTGAATGTA
- 513  CATGTGTACA  CTTGGCATAC  ATGGCAAGAT  TATGTGTTAC  AATATAGACT
- 463  GTGCCATTGC  CATGCAATGT  GACTCCTGTG  GCCATTTCTA  TCACAATGTG
- 413  TCAATCTTGG  AGTATCCGTT  GTTTATCCTC  TAATTTACTG  ATTAATTTAT
- 363  GAACATGTAT  AATTATTTAT  ATCATATGAT  CTCGTAAGAT  ATCTTAGCAT
- 313  TTTCCACCAT  ATGTTATTAG  TAAATCATCT  AGATGGATTG  ATGTAAATAG
- 263  GAAAGTTAAA  TTAACACACC  AAAAAGTAA   CTGATTAAAA  GCATACAACT
- 213  TAATATTCAG  ATTATGGTAA  CTAAATCAGT  CTCATGCAAA  CTCCAAAAAA
- 163  TTATACGAGT  CACAACTCTT  GATTTTTTC   CGGTTAAACA  AAATACATAT
- 113  TTTCATTTGT  ATGCAACCAG  AATAAAACAC  TAACTATCTC  CTTTAAATAC
-  63  CATTTTCCCT  ACGAGTCTAC  GACGCTCTCT  AAACTTCTTA  TACAAAACAA
-  13  AACACACCC   -5

-   4  AAATATG
```

Figure 4

Promoter 07

```
-1118 GATCCGAAAA GTAGAGTTTC GTGGATCTGA TAATTGGAGA AGAGAGAACG
-1068 AGCTGAAACC CTAAATTCGG ATAAAGTCTG CAACTTCTGT TGTTTCGGTG
-1018 GCGAGAACAA AAATAATGAG AGGAAGAGGA AAATATCGTC GTTTTTGTCT
- 968 CACAGTCTCT TTAGCAGCTT TTCTTTAGAT ATTTATTTTA TTTTTTCCAT
- 918 GGATAGAGAG AGCTAGGCAT TCCGGTTATT TGGAGATTTT GGAATTTCAA
- 868 TTTTGCGGTT TGGTATTTTA TTTTATTTTA TCAATTTGAA CGAAACAGAG
- 818 CTTTGTTTTG GTTACGATGC GGTGGATTTT GGTTCGGTTT AGAGTGATAT
- 768 ATATTTGGTA CCAAATTAAA CCAAGATTCG TTTTCGGTAA AAACAAAATT
- 718 TGATTTTTAA GCATTTTTGG AAAAATTAGT GTTATATATA TGAGATTTCT
- 668 TAATCAAAAT CTCACTTTTA TCCGATTTAG TGGTAGTTCA TAAAGTGGTT
- 618 TCATGTATAT GATACCTGAA TAACCAACAT ATGTATTTTA AGAGACACTT
- 568 GGAATAATAA TTCTAAATAT CCTAACTACT CGTGTCCGTA TGTTTTGTCA
- 518 CGGTGAAACG TGAGAGGACT AGTTTTTGTC ACCCGTCCAT AACATTCTTA
- 468 GACATACATT ACTTTGGGAG TGAAAAACAT TAAGCTTATC TTTATCCATA
- 418 TATTGTCTTA CCATCAATAG ACAATATCCA ATGGACCGGT GACCTGCGTG
- 368 TATAAGTAAT TTTTCAAGAT GCTAAAACTT TTATGTATTT CAGAATTAAC
- 318 CTCCAAAAAC ATTTATTGAC ACACTACTAC TCTTTCCGTA TTGACTCTCA
- 268 ACTAGTCATT TCAAAATAAT TGACATGTCA GAACATGAGT TACACATGGT
- 218 TGCATATTGC AAGTAGACGC GGAAACTTGT CACTTCCTTT ACATTGAGT
- 168 TTCCAACACC TAATCACGAC AACAATCATA TAGCTCTCGC ATACAAACAA
- 118 ACATATGCAT GTATTCTTAC ACGTGAACTC CATGCAAGTC TCTTTTCTCA
-  68 CCTATAAATA CCAACCACAC CTTCACCACA TTCTTCACTC GAACCAAAAC
-  18 ATACACACAT AG -7

-   6 CAAAAAATG
```

Figure 5

Promoter 09

```
- 975  TCAGAAAGAG AAGTGAGCTA CCTGCAGTGT CCTCTGTTTT GTCGATGAAG
- 925  GATTTTTAGA TTGGTATGTG ATGAAGTACA ACGAGCTGAT GCCTGCGTTG
- 875  ATGGCTATCT TCACCAAAAG TCGTGTTTGT TATGAAGCAC AACGAGCTGG
- 825  TGCCTACGTT GATGGCTATA TTCACCAAAG GTCGTGTTTC ATAGATCAGA
- 775  AGGCACACCT ACAACAATGA GCAGTGCCAA GGTTTGTTCT TATTTTGTTG
- 725  TTGTCAGTTT TAGATTTCTA GATGAATCTT ATGATGTGAT AATGGAAAAA
- 675  CGAAAGAAAA GCTTTTGTTA AAGTATCTAT GAGTGATATC ATGATATGTC
- 625  AAAAATGTTG CATGGATACA TTGATTCTTT AGTACTTGTT ACGAGCTGCT
- 575  AAGAGAGTCG TGTCAAGTTC AATACTTTTC CTTGTCATTT AACATAATTG
- 525  CTTGTCTGTT TGGATTCTAT TGTGCGGAAG TTATGATTTA TATTTTCAGA
- 475  TTCATATTTT CAATTAGGAA GCTTAGTTG GAATCAAAGT GGATGACCCT
- 425  GATTGAGGAT TTTAATGATC GTTGTGAGAA CCTTTCTTGT AGTTAGTTGG
- 375  TGGATTGTAA AAAAATTATA TGTATTTAAC TCTTGATTGA GAGTCAGAAG
- 325  TTGGAAAAAT GAATTAAGAG GTTTTCGAAT AAGAGATCAC AGTTATAGTA
- 275  TAGTATTAAT TGGATATCAC AATCTATTCA TAATATTAGC TAGTTAGATA
- 225  AAATTGTGTT TGATCTTGGC AAGAGGTGTT AAAATAGTAT CATGTTGACA
- 175  TGTTGGTATG ACTATTAGTC GTAATTTAAG CTTATGTATA TTTCTTGTAA
- 125  GAAATGTTCA TGTATCATAA TAAATACAAG TGTATCGAGT TTTTGTATAT
-  75  ATAGAGGTCT ATGATTTGGG AAGAAGAACA CAACATAACT CACCACAAAC
-  25  ACAATCTAAT CCAAAAAATC AAAG -1

1  ATGAAT
```

Figure 6

Promoter 13

```
-1121 TGACACGCAA CAACCAAAGC CAAAAGGGTG CGTTACCATT AATTCAGGGA
-1071 AAGCGAAATA AACCCAAATC TCTCTTCTAA CGAAGTAACA ACTCACCCAC
-1021 TTCTCACATT GATTCACTCC TTTCCAGTTT TTACATATAG CCTTCGTTCA
- 971 TCAATCACCT TAAGCAAATT GCAATCACAA AAAAAAAAAA GTACAGTACT
- 921 TAGCAAAATT TTAAGTTTTT GTTATTTCCA CGGCAACTTA GCAAATATGC
- 871 ACCACATATT GACATTAGCT AATATACAAC ACATGTTTTT TTAGAAATGT
- 821 ACAAGCATTA ACAAATATCC AACACAAAAT GACATGATCG TAGATGATTA
- 771 AGATAATTCG ATCCTATAAA CTAATAGTTT CCAAAACTTC TGCTGACTTT
- 721 TCTCTCGACA GCGATGGTAA GAAGAAGGTA CAAAGTTTTG AAGCCCGAAT
- 671 ATAACAAAAG GACAGAAAGC TTTTAGTTTT CTAGATAAGA TCTTAGCTTT
- 621 GGTCACGTAA AAAAAATTAA AAGTGAATTG GTTAACAATA TAGGAGTACT
- 571 TTGTATCCAA AGGTCATTGC AATAAATAAA CACTTAAGTA CTCTGTAGTC
- 521 ACACATCTCT AGGAGCTTAA TATTGGATAA TCGCTTGTAG ACTTGTATTA
- 471 AAATATTTAG TAGGTCAAAT CCCTATCTTC TACAGTTTCT ACTCTCGTCC
- 421 GTACAGACTA CAGACACTAT GCTATAGTTT TGTGTTGAAT TCTACAAAGT
- 371 ACAAATTCTT CTTTCGGTGC AATAACAAA TAAACACAAT TCTCAAATTA
- 321 CATTTGTCTA AATTTTTATT TGATTCGGTA TAAATGTAAC GCTATGTTGG
- 271 GAATCATATG ATAAATCCAG ATTAAGACTT CTTATTTAAT TTATTTTTGT
- 221 ATATATAAAA TATAATATCC AACCATAAAG TTTTTTTACC GATCGATGAT
- 171 AATGTGAATC CAAATATTTT AACAGGATGA TAAATAATTG ATGTGGCTTT
- 121 TATAACCGCA GCAATTCTGG CGTGACTCTC TCCGCAGCAT TTATTTTTCT
-  71 CTCTATAAAT TAAAAACATT ACTTACTCTT TCTCTCTTCC ACTTAACTCA
-  21 TATCAACCTT CGCCGGA    -5

-   4 AATAATG
```

Figure 7

Promoter 14

```
-1056 ATCTCTGCAA ATCAAACCTT ATTATTAAGC TACATTTACA TAGTGTCCTT
-1006 ATAATTCTCA TGACATAGCA ACATTATTAA ACGACAACTT TCTAGCTTCA
- 956 TTTAAAATGG AAAATCACAT AACACTCACA TTAACTATAC TAACATAACA
- 906 CTCACATTAC CGACTAGCAT ATAAATGGAT ATTGATATAA CAATAATCCC
- 856 CCAAATTTAT GTCTATTTTG TTCATTATGC AAATGTCCCA AAATGATATA
- 806 TCTTGGAAAG TACTAACCGG AGACGAGGGT CGAGGTATAG AAGTGATTTG
- 756 GTCGAACCGA AATGAGGAAC CCGGGTTTGG ACACCAGGAG CATTTTGGTA
- 706 ATCATCCAAA TCAGGGTCAT AGTACAACAT CATTCGATCG CTGAAGCACC
- 656 TGGTGAAGGG AGACAATAAC ACTGCTGCAT CGAACCATAG CCTAAACCAT
- 606 CCACCACTCT TCTTATGAAT CGGATATAAC CAGCTGCTAC ACCAGACACT
- 556 ACTTGGCTTG TATTCTCTGT CCAGCCGTAC CTCTAGCTGG TTACCTCCGT
- 506 TTCCTGGAAC CAGAATCAAA GGGTACACGT TGCTACCCAC AGCTTGACAC
- 456 ATCGAGGTCA TCGTCACCAC AACGAGTATC GCTATGACTA CCGAATAATG
- 406 TGAAGATATT TTTTTCATTT TCGTTCTAAG AAACAGACTC TCATGGTCAT
- 356 GGATCTATGC AGAAAGCTGG AGATTTGAAG AAAAAGGTCC ATTGAATTTG
- 306 AAAAACAGAG TAGTATCTTA AAACGTAAGG CTTAAGATAA GTAGTATATG
- 256 GTGGATATGG AACCCGCGTA ATCATCTAGA GGCTCTACAA ATATTTATTT
- 206 TGTATTTCCT TCTTATTTTG TATTTGCCTA CGTGGCATTA TACAACGTAT
- 156 TTAACTTGAA ACCAGATTTA TGGCCCAATG GGTCGGGTCG ACCCGACCGA
- 106 TTTTAAACTG CGCTCCTAAC TAAAAAAAAG TCAAACCCCT TGAAAAACC
-  56 TAAAAACGCA ATTTGCTTCG TCGTCTCTCA TCTCTTTCTC TTTCTCCG -9

-   8 TCGCCACCATG
```

Figure 8

Promoter 15-2

```
-1074 GTAAGTCGTT CTCTAATCTT CCATGCCAAT TTGCTCGGTT AAAACCAGAC
-1024 TGGTTGGACT GAAAAATCGG TTTTAATTAA TTGAGTTGTG CTTATGAGGT
- 974 CTATTGGTTT ATTTTTAAAA TCCTTTGTAG ATTAGGAGAG TACCAACAAG
- 924 AGCGAAAGAC ATCACTAAAC ACGAAGAGTG AAAGTGGAAA AAGAGAACTA
- 874 TCAAGACTTG ACTCGAAGAC CGGATTGTAC CCGGATGATT CGAAACAGGG
- 824 CGGTGCTGGT GCTGGTGCTG GTGGTTGGCT TTCTTGTTGT CTCTGTTTTT
- 774 CGGTGAAAAA TTGAGGTTAT TACTCTTTGT CATGTCAATT ATTTAGGTCA
- 724 TAGCTGTCCA AGAGACGCGA GACATTAGAC AAGGTAATTA CCGATTGTAT
- 674 CCTATATATT CCTATGTAAC GAAATTCAGA TACTACGTAA TCTTAATGTG
- 624 TCGATGGAAT GAAAAAATAA AGTATTCTGT AAATATTTTC TATATATTAT
- 574 TTAGCATATA TACGCTTTAT AAATTATAAA TTTGGTCCCT CCCAAATACA
- 524 TGAAAACAAT GTAGTGATAA AAAAAAAACA AATTCTGTAT ATATGCTATT
- 474 TTTATAACAT AACAAGCATT TTTCTTAGTC GGTTAAAATT TCAAGTGTTT
- 424 AATACTTTTA TATAATTATG AACGTAAGTT ATAATCTATG TTTTTTTTGG
- 374 TCAGTCCATT ATTGATTATT CCATTCACAC TATATGCAAC CTATATTCTT
- 324 CCTATGAAAC TTTTGATCGT GTGTTAAATA ATAATACAAA TTTGATTTCA
- 274 TCTAATAGGT GGGTGGGGAC TCTCTAATTA CGTTCTTTGA CATCTACTCA
- 224 TCAACATTTG GCTAATCTTT CTAAGGAAT TCCATCTACC GGTCATTTTT
- 174 GTTTAAATGC TCTCTTGTAA CTAAAGTCC GTACCAAACT TGTGTAATTT
- 124 CATTAAACAT TAATTATTTA GTCCATTCCA TGTCAAATAT GACTTCTATG
-  74 CTCTTGTCCT ATAAATTTTA AAGCAATGAG GATTCACCAA GTATACATGC
-  24 ATAACAAATT AAGAGCGAG -6

-  5 CAATAATG
```

Figure 9

Promoter 16

```
-1044  GTGAGAAAAT TCATGAGCAC TCTTAGAAAT GTAAATAGTT TGATTTGAAG
- 994  AAATGTGGTT TTTAAGAAGA TAATTGCAAA ACTCAGAAAG GATTTCACAA
- 944  AAAACAATTC GTGAAATCTT TCCTGAATTT CGTAAAATCC TTTCTAAATT
- 894  TTAGAAAATT ATTATTTGAA TGATTTTACG AAATTTCGGA AGAATCTAT
- 844  AAAATTCAGG AAAGATATCA TAAAATTTAT GAAGAGTTAT ACACAACAAA
- 794  AAGAAATTTT TGAATTTCAT GAATCCTTC GTAATTGCTT ACATTCCTTC
- 744  CTAAATTTTG TAAAATTCTT CCTGGATTTT CTTTTGCGAG AAAATAGGGG
- 694  CATATATTTT TTACGGGAAA TTTTTTGACG AAAACTTATT TTGGCGGAAA
- 644  AAATTGTCAG GAATTTTTGG TAATGAATAT GTGTATTTTT TTAATTGTTA
- 594  ATTTTAATAA TAAAATAAAA TAGTTATCTG AATGTTATTT ATGTCAAAAA
- 544  AAAATATGAA TGCTATTTTT GTCTTAAAAA CTTAAAATTG TACTATTTGA
- 494  AGGAATTTCA TTTTATTTTA TTAATGTGAT TAGATTTATA ATTAAATATA
- 444  ATTAAATGAT TGTAAATACT AACTTAAATT CTTATTTATA AACATAAAGT
- 394  AATATTTAAT TTTCTTTAAT TAAAAATACA TATTTTATTT TCATAATTTA
- 344  TTTTGCTTTT TTTTTTTTTT AGTTTGATT TATTTTTAAA CATATAATAT
- 294  GAGTATATGA CTATATGACA TAGCATATTG GTTTATTTTG ATTAGATAGA
- 244  AAAAGAGACG GGTGAATAAA AGGGTTTAAT ACTATGGTGA ACCCAAGTAT
- 194  ATATCGTCCA TAACAAAAAC ACTATATAAT TGAGGTTTGT AGATTGTGCA
- 144  AACACGTGTG GGCATATCAG CTTGTAGGAT TGCCACATAC ATTATCATGA
-  94  GAAGCTTCCA CCAGAATAAA GCAAAACAAA AAACTCCGAA AGCGGAGAGA
-  44  ACAAGGAAAA CTGAAAAACC ATTGTGAAGT ATAGTCCTTG ATGC -1

1  ATGGATT
```

Figure 10

Promoter 17

```
-1141 CAAACGAGGC TCCAAATTCA TATTCGGCCT GCATACTTTT GCCCTGGCCC
-1091 GGTTTTTTTT TTTCTTTTTT TCGGTGTTTC ATAATACATC AGCTTCCATA
-1041 ACTGGAGCAA CCGTTATAGA AAGACATGTA TAAGAACCCC AAAAAAACAG
- 991 GTACGTCAAA AGAGGAAATT CTCATAACAT ACACAATATG CTCCTAATCA
- 941 GCCATCGTGT TGTGCTGATC TCCTAGGTGA CATTATGTAT ATCTGTTTGA
- 891 TATTTCTTTA ACACAACATG TTATCAGTTA CCCATCAAAA CGTAGTCAGC
- 841 TTGAGGTCTT CCAAAAAAAT CCACACTAGA CCTTCCTTCA TCACTTCAAC
- 791 AGACTTCAAA CTTCTATCCC AAAAGGAAAA AACTAAATAA GTTGAAAGGA
- 741 ATGGTCGAAG GCATGGGGAG ACACCTAATA CGGCAGCTAG ACTAATCCGG
- 691 TGGATTGATA AGCAAACTCG AAACACTCTT TCCTCTATCA GATTATTGGG
- 641 GGATAGGAGA TATGACAAAA GACTGCAAAT GTGGTTTGCT TCTAGAAGTT
- 591 AAGAGCTTCC GGGATTTGT TTTTTATTTT TTCAGTGTTG TAACAAATTT
- 541 AAATTCTGTC GCACTTGTCG TAACAACGAT ATTTTTTCTT TGAATATAAT
- 491 TTAACATTAA ATTAAAAGA AAAACTAAAT AAATTATTTT GAAGTTAATA
- 441 TATTATGTTA TTATCTTTGG TTTGCAATAA ATAGATCGAG TCAAGGTCGT
- 391 TATATGACCA TTGTTTAGTT ACGACGCTAC TTCATACTTG GAATCTAAGG
- 341 AGAAAAAATG TAACATAGTT CTCAGTACTT AATCACATAG TTCTCAGTTC
- 291 TTAATCACTT TATTGTTAAA ACTTTTCATC GAATAATTAA TGATTTGATC
- 241 TCCAATCTCA ATTAATTATA TATTTCTAAA GCCAAAAGAG ATAATGAAAG
- 191 GAGAGGTGGT AGAAAGAAAA CGTTAATGTA TCAAACTCTA ATAAAAGAAA
- 141 CTGCGTGTAT AGACACGAAG GCTCCGATCT TTTGCATGTC TCGCACGTGT
-  91 CGTCCTCTTT CTTCCTACTT AACACATATA TGCATGCACC CTTCTTAGAA
-  41 AAGTAGCAAA ACATTGTGAA TCATCGGAGA GAGTGGGAAA C -1

1 ATGGAGA
```

Figure 11

Promoter 19

```
-1293 CACCAAGCCT ATACAAACAT AATTTAACGC CGCCTAGTTT TGTTTATTCT
-1243 GCACGTAACA TATAAAGCTA ACAGATATGC GACAAAATAT CTATAAATTA
-1193 CATATATAAG TATATATAAT ATAAGAATGT TGGATGTATA TATTAGTAGT
-1143 TTAATCAATG AAAATATATC TTTATATCTT TATTAAAAAA ACTAAAAATG
-1093 TATCTTTATA TACATTTCGT AGTTTAAAAT CAAAATTCAA GATAGAGCGA
-1043 AAATGATTTT TTTTTTTTTA AATGAACCAA AAGTACAACA TTCCTACCTT
- 993 TATTTTTAAT AACTCGTTTA TATTCGCCAA TCAGACACAC ACATAGACTT
- 943 TTAAAATAGT AAAAGTAACT TAGCCGATTA TTTATGTAAA ATATTCGTAT
- 893 AAAATTTTTA TTAACAAATA TATTTGATTT CTCATCTTAT AACCTGTTTA
- 843 TTGATCAGAT TACACGAAAA AATAACTAAA CAGATAAATT TACTCGAACT
- 793 GCATACAATA GAGATGTATT TGTGCATGAG TGTAGCCCAA AAATGTGTAA
- 743 GGAAATAACA CCCATTGGTA GGCCGAGACA TGCCTGTACC ATGGCCGCTG
- 693 AAATAGTAGA AGAACCAAAT ACCTACCAAA GTACTCTTAA GCTAACGTTG
- 643 ACATGATTTA ATTAGATTAA CGATTGAGTA AACGACAAAT TAGCGCTTTC
- 593 GTTTTATATT AAAGACGCAC GATATTTAAA TGGCAACTAT ACATTAAAAT
- 543 TATATAAAAT ATATAACTAT AACCAATTTG ATAAATGAGA AAAATGTACG
- 493 ATATGTCGTA CCACTCCATC CTGACTATGA CTTATGGAGG AAGTCAATGC
- 443 TTATCAACTA CTTGCTTATC AATATCCTAT TTATCACTAT CAGTTTTTCT
- 393 CTTTTCTATA CATATATTAT TTCCTATAGA TCATGTTGGT CATAATGTAA
- 343 TCAACTTAAA ATTTAAGATC TACTAGTTTG TGTTGAAGTA TAACTGTATA
- 293 AGCCTAAATT CGAACGTTAG TCTGACTTAA TAGTTAATTC CATTTTGTTT
- 243 TGGGTAAATG TTTCAGTTTC ACTGCTGTTT GGAAAATCTT TGGACAGATA
- 193 TTGAGATTGG GCTTATAATA TTTATTATTG GGCCTTAATT TAAGAGCCCT
- 143 TTTATAGGCA GATACAAAAA CGACGGCGTT TAACTCATCC GCTCAGCGAC
-  93 TTCCACATAG CCGTTAAAAC GATGATAATA AACCCAATCC GGTTCATCTC
-  43 CAACAGAAGA ACGTAATAAC TGATGCTTGT CTTCAAGTCA AC -2

-   1 CATGGAGT
```

Figure 12

Promoter 6 :

GATCTCTCCCGAAGAAG

CTAAACGAGTAAAGTTTAGCACGATTGAGACCACACTGACCCATAGCAGTCCAATGAGC
TACGGAAGGCCTAGGGCTTGAGGCTTGATGAGCGCGTGGTGGAATAGCGTTTGAATCTA
AAGTTCGGTTTGGTACGACTTGTAATATGAAATAATAATGTACAAAGAAGTTCTACGCT
TAAGGGAACTGTTTTGTTTTGAGCTTTGTATTAGGACGTCTAGTGTACAACAACGAACG
TCGTGTATAAGCGATCGTTGACTCTGCACATGTAACTCTTTCCTGAATAAAAAATCTTT
AAGTCTTTAATTTCTACATCTTTTAGGATTATATAAACGTTACTATATAAATAAAAAG
AAAAAAAAATCAGTTCACTAACATGCGAGACTTTGGGCTAAATATAGTGATTCCAAAGA
AAATGAGTTATAATATTAATTAATATAAAGCTCATTTTCTTTGGAATATCGTTATAAGA
ATATTTAACTTGGATATAACTGGGCTTACGCCATTTGCATCTCGAGGATTTTTTGTTT
TTGTTTTTGTTTTTTTAATACATTCTCGCACTTACACACTAAAAATCATAATGATCTTC
TTAATTCTTTAGCGGAACCACCAATTAATCTTTTTATTAAGAACTTTATTACTTATTTC
ACTTATTTGTGCATACGTGCATTATTTTGGCAGTAACAAATATCGCGTTATATATACTG
AAATCCGGACGCATTAATAATAGGGATATGATTATATGAACCACTATCTAGCTTTGGTA
GAAACCCAATTATAATCAAATAATTTACCATTATTGAATAAATTAGGCTATATAAGTTC
ATTAATAGATGCTATAGGTTTTTCTTACAAGGCACACATTTGATTGTTATTTCTTTCA
TATACACTGAATGTACATGTGTACACTTGGCATACATGGCAAGATTATGTGTTACAATA
TAGACTGTGCCATTGCCATGCAATGTGACTCCTGTGGCCATTTCTATCACAATGTGTCA
ATCTTGGAGTATCCGTTGTTTATCCTCTAATTTACTGATTAATTTATGAACATGTATAA
TTATTTATATCATATGATCTCGTAAGATATCTTAGCATTTTCCACCATATGTTATTAGT
AAATCATCTAGATGGATTGATGTAAATAGGAAAGTTAAATTAACACACCAAAAAGTAA
CTGATTAAAAGCATACAACTTAATATTCAGATTATGGTAACTAAATCAGTCTCATGCAA
ACTCCAAAAAATTATACGAGTCACAACTCTTGATTTTTTCCGGTTAAACAAAATACAT
ATTTTCATTTGTATGCAACCAGAATAAAACACTAACTATCTCCTTTAAATACCATTTTC
CCTACGAGTCTACGACGCTCTCTAAACTTCTTATACAAAACAAAACACACCC

AAATATG

```
Query:  1 ATTCCAAAGAAAATGAGTTATAATATTAATTAATATAA-AGCTCATTTTCTTTGGAAT 57
          |||||||||||||||||||| | || ||||||||||||| | | ||||||||||||||||
Sbjct: 57 ATTCCAAAGAAAATGAGCTTTA-TATTAATTAATATTATAACTCATTTTCTTTGGAAT  1
```

Figure 15

Promoter 14 :

```
CATCTCTGCAAATCAAACCTTATTATTAAGCTACATTTACATAGTGTCCTTATAATTCT
CATGACATAGCAACATTATTAAACGACAACTTTCTAGCTTCATTTAAAATGGAAAATCA
CATAACACTCACATTAACTATACTAACATAACACTCACATTACCGACTAGCATATAAAT
GGATATTGATATAACAATAATCCCCCAAATTTATGTCTATTTTGTTCATTATGCAAATG
TCCCAAAATGATATATCTTGGAAAGTACTAACCGGAGACGAGGGTCGAGGTATAGAAGT
GATTTGGTCGAACCGAAATGAGGAACCCGGGTTTGGACACCAGGAGCATTTTGGTAATC
ATCCAAATCAGGGTCATAGTACAACATCATTCGATCGCTGAAGCACCTGGTGAAGGGAG
ACAATAACACTGCTGCATCGAACCATAGCCTAAACCATCCACCACTCTTCTTATGAATC
GGATATAACCAGCTGCTACACCAGACACTACTTGGCTTGTATTCTCTGTCCAGCCGTAC
CTCTAGCTGGTTACCTCCGTTTCCTGGAACCAGAATCAAAGGGTACACGTTGCTACCCA
CAGCTTGACACATCGAGGTCATCGTCACCACAACGAGTATCGCTATGACTACCGAATAA
TGTGAAGATATTTTTTTCATTTTCGTTCTAAGAAACAGACTCTCATGGTCATGGATCTA
TGCAGAAAGCTGGAGATTTGAAGAAAAGGTCCATTGAATTTGAAAAACAGAGTAGTAT
CTTAAAACGTAAGGCTTAAGATAAGTAGTATATGGTGGATATGGAACCCGCGTAATCAT
CTAGAGGCTCTACAAATATTTATTTTGTATTTCCTTCTTATTTTGTATTTGCCTACGTG
GCATTATACAACGTATTTAACTTGAAACCAGATTTATGGCCCAATGGGTCGGGTCGACC
CGACCGATTTTAAACTGCGCTCCTAACTAAAAAAAAGTCAAAACCCTTTGAAAAACCTA
AAAACGCAATTTGCTTCGTCGTCTCTCATCTCTTTCTCTTTCTCCG

TCGCCACCATGTTTGAGTACCGGTGCAGCTC
```

```
Query:  1   AATGGGTCGGGTCGACCCGACCGATT  26
            ||| |||||||||||||||||||| |||
Sbjct:  26  AATCGGTCGGGTCGACCCGACCCATT  1
```

Figure 16

Promoter 16 :

AGGGACTAGGAACTTAAGAAAAACAAAGTCATCAAAAAAACAAAAAAAAAGTT

GTGAGAAAATTCATGAGCACTCTTAGAAATGTAAATAGTTTGATTTGAAGAAATGTGGT
TTTTAAGAAGATAATTGCAAAACTCAGAAAGGATTTCACAAAAAACAATTCGTGAAATC
TTTCCTGAATTTCGTAAAATCCTTTCTAAATTTTAGAAAATTATTATTTGAATGATTTT
ACGAAATTTCGGAAAGAATCTATAAAATTCAGGAAAGATATCATAAAATTTATGAAGAG
TTATACACAACAAAAGAAATTTTTGAATTTCATGAAATCCTTCGTAATTGCTTACATT
CCTTCCTAAATTTTGTAAAATTCTTCCTGGATTTTCTTTTGCGAGAAAATAGGGGCATA
TATTTTTTACGGGAAATTTTTTGACGAAAACTTATTTTGGCGGAAAAAATTGTCAGGAA
TTTTTGGTAATGAATATGTGTATTTTTTAATTGTTAATTTTAATAATAAAATAAAATA
GTTATCTGAATGTTATTTATGTCAAAAAAAAATATGAATGCTATTTTGTCTTAAAAAC
TTAAAATTGTACTATTTGAAGGAATTTCATTTTATTTTATTAATGTGATTAGATTTATA
ATTAAATATAATTAAATGATTGTAAATACTAACTTAAATTCTTATTTATAAACATAAAG
TAATATTTAATTTTCTTTAATTAAAAATACATATTTTATTTTCATAATTTATTTTGCTT
TTTTTTTTTTTTAGTTTTGATTTATTTTTAAACATATAATATGAGTATATGACTATATG
ACATAGCATATTGGTTTATTTTGATTAGATAGAAAAGAGACGGGTGAATAAAAGGGTT
TAATACTATGGTGAACCCAAGTATATATCGTCCATAACAAAAACACTATATAATTGAGG
TTTGTAGATTGTGCAAACACGTGTGGGCATATCAGCTTGTAGGATTGCCACATACATTA
TCATGAAGCTTCCACCAGAATAAAGCAAAACAAAAAACTCCGAAAGCGGAGAGAACA
AGGAAAACTGAAAAACCATTGTGAAGTATAGTCCTTGATGC

ATGGATTCAATCAACAAGATCATCAACTTCTTGTTTCCTCTCT

```
Query:   1  TGAAATCTTTCCTGAATTTCGTAAAATCCTTTCTAAATTTTAGAAAATTATTATTTGAAT  60
            ||| ||||||||||||||||  || | || || | ||||||  ||||| |||    |||
Sbjct: 109  TGATATCTTTCCTGAATTTTATAGATTCTTTCCGAAATTTCGTAAAATCATTCAAATAAT  50

Query:  61  GATTTTACGAAATTTCGGAAAGAATCTATAAAATTCAGGAAAGATATCA  109
            ||||||   ||||||  | || || | ||  ||||||||||||||| |||
Sbjct:  49  AATTTTCTAAAATTTAGAAAGGATTTTACGAAATTCAGGAAAGATTTCA  1
```

Figure 17

Table 2. Selected Seed-Specific Genes

The selected ESTs and their predicted protein sequences were blasted against protein and DNA sequence databases of NCBI, to identify a possible function of each gene and its corresponding Arabidopsis genome sequence.

| ID | Description based on BLAST search of EST | Expression Ratio | Clone ID | Accession Number of Genomic Clone | BLAST Alignment of EST to Genomic Sequence | |
|---|---|---|---|---|---|---|
| 1 | 12S Cruciferin | 49.9 | M30C01 | AL021749 | 13---283<br>65745---66103 | |
| 2 | 12S seed storage protein | 78.8 | M29F06 | AB005239 | 191---399<br>15999---15804 | |
| 3 | 2S SEED STORAGE PROTEIN 3 PRECURSOR | 41.5 | M09C04 | AL035680 | 8---369<br>32165---32525 | |
| 4 | vicilin precursor | 19.1 | M60B08 | AB022223 | 17---400<br>2559---2943 | |
| 5 | similarity to vicilin (7S globulin) | 17.3 | M51A09 | Z99708 | 15---328<br>69093---69460 | 327---399<br>69490---69563 |
| 6 | 12S seed storage protein | 23.4 | M19H03 | AC003027 | 34---220<br>67515---67329 | 218---400<br>67229---67048 |
| 7 | 2S SEED STORAGE PROTEIN 1 PRECURSOR | 60.0 | M52E11 | AL035680 | 22---380<br>27709---28066 | |
| 8 | Unknown gene Laccase-like (diphenol oxidase) | 11.6 | M18A04 | AB017064 | 24---150<br>66806---66680 | 148---371<br>66193---65973 |
| 9 | Unknown protein Arabidopsis | 37.2 | M42C12 | AC000375 | 16---399<br>8408---8025 | |
| 10 | unknown protein | 29.7 | M20H04 | AC004392 | 25---390<br>90414---90780 | |
| 11 | Putative pyruvate kinase | 69.2 | M36D01 | AB009055 | 32---374<br>68629---68966 | |
| 12 | pyruvate dehydrogenase E1 alpha subunit | 27.5 | M15B07 | AC007323 | 3---373<br>48490---48120 | |
| 13 | Similar to nucleoid DNA-binding protein, aspartic proteinase, and pepsinogen A precursor | 7.0 | M42A08 | AB026658 | 28---393<br>68590---68226 | |
| 14 | A large hypothetical protein | 8.6 | M40D09 | AC004557 | 18---393<br>82725---82350 | |
| 15 | germin-like protein (oxalate oxidase), similar to auxin-binding protein, plant only | 42.1 | M31F10 | AB010694 | 13---400<br>18058---17673 | |
| 16 | Similar to 11beta-hydroxysteroid dehydrogenase, oxidoreductase | 39.3 | M13A03 | AB023037 | 9---201<br>52852---52660<br>395---426<br>52096---52065 | 199---388<br>52589---52400 |

Figure 18a

| ID | Description based on BLAST search of EST | Expression Ratio | Clone ID | Accession Number of Genomic Clone | BLAST Alignment of EST to Genomic Sequence | |
|---|---|---|---|---|---|---|
| 17 | putative seed storage protein (vicilin-like) | 19.0 | M32C09 | AC006587 | 23---161<br>14510---14372<br>342---400<br>14033---13975 | 158---341<br>14289---14106 |
| 18 | Lipoxygenase-like protein | 16.8 | M30E03 | AB022215 | 21---99<br>47943---48021 | 96---308<br>48768---48978 |
| 19 | Unknown gene, some similarity to selenium-binding protein-like gene | 31.8 | M55E09 | AC002387 | 26---90<br>73712---73648<br>245---400<br>73308---73153 | 89---244<br>72555---73400 |
| 20 | Cytochrome P450-like protein | 25.4 | M32E09 | AB007648 | 21---394<br>16931---16559 | |

Figure 18b

Table 3. Primers for the PCR amplification of 12 promoter regions

| name | sequence | position | REs | T(°C) | Length 1 | Length2 |
|---|---|---|---|---|---|---|
| 1R | CACT GGATCC TTTTTGTTTGTTGTGTGAGAGATG (SEQ ID NO: 31) | best+3 | Bam | 48 | 23 | 32 |
| 1F | CACT GAATTC ACAAACATACACTCAAAATC (SEQ ID NO: 32) | best | Eco | 48 | 21 | 30 |
| 3R | CACT GGATCC GTTTTGCTATTTGTGTATGTTTC (SEQ ID NO: 33) | best+0 | Bam | 48 | 24 | 34 |
| 3F | CACT GAATTC AAGAGTGTAAAACGTAC (SEQ ID NO: 34) | best | Eco | 48 | 18 | 27 |
| 4R2 | CACT GGATCC C TTGTTGTTTGTTGATGTGTT (SEQ ID NO: 35) | best+5 | Bam | 48 | 22 | 31 |
| 4F2 | CACT GAATT C CATTGTTTACACGTC (SEQ ID NO: 36) | best | Eco | 48 | 16 | 25 |
| 6R | CACT GGATCC GGGTGTGTTTGTTTGTATAAG (SEQ ID NO: 37) | best+4 | Bam | 52 | 23 | 33 |
| 6F | CACT GAATT C TAAACGAGTAAAGTTTAGCAC (SEQ ID NO: 38) | best | Eco | 52 | 22 | 31 |
| 7R | CACT GGATC C TATGTGTGTATGTTTTGGTTC (SEQ ID NO: 39) | best+6 | Bam | 52 | 22 | 31 |

Figure 19a

| name | sequence | position | REs | T(°C) | Length 1 | Length2 |
|---|---|---|---|---|---|---|
| 7F | CACT GAATTC GATCCGAAAAGTAGAGTTTC (SEQ ID NO: 40) | best | Eco | 52 | 20 | 30 |
| 9R2 | CACT GGATC C TTTTGATTTTTGGATTAGATTGTGTTTGTGGT (SEQ ID NO: 41) | nb+0 | Bam | 52 | 34 | 43 |
| 9F | CACT GAAT TC AGAAAGAGAAGTGAGC (SEQ ID NO: 42) | best | Eco | 52 | 18 | 26 |
| 13R | CACT GGA TCC GGCGAAGGTTGATATGA (SEQ ID NO: 43) | best+4 | Bam | 60 | 20 | 27 |
| 13F | CACT CAAT TG ACACGCAACAACCAAAGC (SEQ ID NO: 44) | best | Mfe | 60 | 20 | 28 |
| 14R | CACT GGATC C GGAGAAAGAGAAAGAGAT (SEQ ID NO: 45) | best+8 | Bam | 52 | 19 | 28 |
| 14F | CACT GAATT C ATCTCTGCAAATCAAACC (SEQ ID NO: 46) | best | Eco | 52 | 19 | 28 |
| 15R | CACT GGATC C TCGCTCTTAATTTGTTATGC (SEQ ID NO: 47) | best+5 | Bam | 52 | 21 | 30 |
| 15F | CACT CAATT G TAAGTCGTTCTCTAATCTTC (SEQ ID NO: 48) | best | Mfe | 52 | 21 | 30 |
| 16R | CACT GGATCC GCATCAAGGACTATACTTCAC (SEQ ID NO: 49) | best+0 | Bam | 56 | 21 | 31 |

Figure 19b

| name | sequence | position | REs | T(°C) | Length 1 | Length2 |
|---|---|---|---|---|---|---|
| 16F | CACT GAATTC GTGAGAAAATTCATGAGCACTC (SEQ ID NO: 50) | best | Eco | 56 | 22 | 32 |
| 17R | CACT GGATCC GTTCCCACTCTCTCC (SEQ ID NO: 51) | best+0 | Bam | 56 | 16 | 26 |
| 17F | CACT GAATT C AAACGAGGCTCCAAATTC (SEQ ID NO: 52) | best | Eco | 56 | 19 | 28 |
| 19R | CACT GGATCC GTTGACTTGAAGACAAGC (SEQ ID NO: 53) | best+1 | Bam | 52 | 18 | 28 |
| 19F | CACT GAATT C ACCAAGCCTATACAAAC (SEQ ID NO: 54) | best | Eco | 52 | 18 | 27 |

Position: Distance from the best position ( for reverse primers, it is ATG )

REs : Restriction enzyme sites included

T(°C): Annealing tempeture

Length 1: Length of the sequences exist in genomic sequences

Length 2: Full length

Figure 19c

PLANT SEED SPECIFIC PROMOTERS

This application is a continuation of, and claims priority to, U.S. patent application Ser. No. 11/488,274, filed Jul. 18, 2006, which issued as U.S. Pat. No. 7,405,345 on Jul. 29, 2008, and which is a continuation of, and claims priority to, U.S. patent application Ser. No. 09/998,059, filed Nov. 30, 2001, which issued as U.S. Pat. No. 7,081,565 on Jul. 25, 2006, and which claims priority under 35 U.S.C. 119(e) to U.S. provisional patent application Ser. No. 60/250,401, filed on Dec. 1, 2000.

This invention was made in part during work partially supported by the United States National Science Foundation grant no. DCB94-06466. The United States government may have certain rights in the invention.

FIELD OF THE INVENTION

The present invention relates to novel seed specific promoter regions. The present invention further provides methods of producing proteins and other products of interest and methods of controlling expression of nucleic acid sequences of interest using the seed specific promoter regions.

BACKGROUND OF THE INVENTION

The major economic and food value of most agricultural plant products resides in their seeds, and seeds have long been the major resources of proteins, carbohydrates, and oils. Centuries of agricultural research have been directed to improving the qualitative and quantitative traits associated with seed products; classical breeding techniques have resulted in the development of new varieties with desirable traits not observed in the source populations from which the new varieties are developed. However, despite recent rapid progress, these techniques are limited to recombining genetic information which is already present in the source population, and to the very slow modification of this information by naturally occurring mutations. Furthermore, these classical methods may also result in undesirable traits arising as a consequence of selecting for a particular desirable trait. For example, it was impossible to increase the oleic acid content of rapeseed oil above 80% without obtaining undesired agronomic properties such as reduced cold tolerance; it was hypothesized that the observed reduction in cold tolerance was due to the lack of unsaturated fatty acids in the membranes of these plants (Kinney, Current Opinion in Biotechnology, 5:144-151 (1994); Miquel et al., Plant Physiology, 106:421-427 (1994)). Thus, the characteristic of high oleic acid, which is desirable when present in the seed oil (which consists primarily of storage lipids, or triacylglycerols), is undesirable when present in the membrane lipids (which consist primarily of glycerolipids).

The application of the newer techniques of genetic engineering promises to revolutionize plant agriculture. It is envisioned that traditional seed products can be tailored to the end market, as for example, seed oils produced with specific fatty acid profiles. Thus, it has been possible to produce a rapeseed line with 88% oleic acid in the triacylglycerol fraction of the seed oil, by transferring an antisense gene to a fatty acid desaturase, FAD2, to the rapeseed; this desirable characteristic was limited to the seed oils, and therefore did not affect the fatty acids of the membrane lipids of the rest of the plant, by putting the antisense gene under control of the napin seed-specific promoter (Hitz et al., Kader, J.-C. and Mazliak, P., Eds. (Kluwer, Dordecht, Netherlands), p. 534 (1995)). It is also envisioned that seeds can be used produce non-traditional products, such as edible vaccines. However, for these applications as well, it is preferable to utilize seed specific promoters, to limit the presence of such non-traditional products to the seed, and to avoid their presence in other parts of the plant.

Only a few seed-specific promoters have been cloned and studied in detail; these include promoters for seed storage protein genes, such as a phaseolin promoter (U.S. Pat. No. 5,504,200) and a napin promoter (U.S. Pat. No. 5,608,152). Storage proteins are usually present in large amounts, making it relatively easy to isolate storage protein genes and the gene promoters. Even so, the number of available seed specific promoters is still limited. Furthermore, most of these promoters suffer from several drawbacks; they have a limited period of time during seed development in which they are active, and they may be expressed in other tissues as well. For example, storage protein gene promoters are expressed mainly in the mid to late embryo development stage (Chen et al., Dev. Genet., 10(2): 112-122 (1989); Keddie et al., Plant Mol. Biol., 19(3):443-53 (1992); Sjodahl et al., Planta., 197(2):264-71 (1995); Reidt et al., Plant J., 21(5):401-8 (2000)), and also may have activity in other tissues, such as pollen, stamen and/or anthers (as, for example, the phaseolin promoter, as reported by Ahm, V, et al. Plant Phys 109:1151-1158 (1995)).

Therefore, it would be desirable to have additional seed-specific promoters for use in modifying seed products. It would also be desirable to have seed-specific promoters which are more tightly expressed only in seed tissue. It would also be desirable to have seed-specific promoters which are active during different phases of seed development, and which are active to different degrees during seed development It would also be desirable to have a method by which such seed-specific promoters can be identified.

SUMMARY OF THE INVENTION

It is an object of the present invention to provide novel seed-specific promoters. It is a further object of the present invention to provide seed-specific promoters which are more tightly expressed seed tissue. It is yet a further object of the present invention to provide methods by which additional seed-specific promoters can be identified. It is yet a further object of the present invention to provide methods by which expression of genes of interest can be controlled by using novel seed-specific promoters, and methods by which production of proteins and other products of interest can be limited to seed tissue.

These and other objects are met by the present invention. In some embodiments the present invention provides an isolated DNA molecule comprising a plant promoter region, wherein the promoter region is a seed-specific promoter region and is selected from the group consisting of SEQ ID NOS: 1, 2, 3, 4, 5, 6, 7, 8, 9, 10, 11, and 12 (as shown in FIG. 1-12); preferably, the promoter region is selected from the group consisting of SEQ ID NOS: 1, 2, 3, 4, 10, and 12.

In other embodiments, the present invention provides an isolated DNA molecule comprising a plant promoter region which hybridizes under low stringency to a sequence selected from the group consisting of SEQ ID NOS: 1, 2, 3, 4, 5, 6, 7, 8, 9, 10, 11, and 12 (as shown in FIGS. 1-12) and which is effective as a seed-specific promoter. In yet other embodiments, the present invention provides an isolated DNA molecule comprising a plant promoter region which hybridizes under medium stringency to a sequence selected from the group consisting of SEQ ID NOS: 1, 2, 3, 4, 5, 6, 7, 8, 9, 10, 11, and 12 (as shown in FIGS. 1-12) and which is effective as a seed-specific promoter. In some further embodiments, the present invention provides an isolated DNA molecule comprising a plant promoter region which hybridizes under high stringency to a sequence selected from the group consisting of SEQ ID NOS: 1, 2, 3, 4, 5, 6, 7, 8, 9, 10, 11, and 12 (as shown in FIGS. 1-12) and which is effective as a seed-specific promoter.

In certain embodiments, the present invention provides an isolated DNA molecule comprising a plant promoter region which is a fragment of one of SEQ ID NOS: 1, 2, 3, 4, 5, 6, 7, 8, 9, 10, 11, and 12 (as shown in FIGS. 1-12) and which is effective as a seed-specific promoter. In other embodiments, the present invention provides an isolated DNA molecule comprising a plant promoter region which is a modification of one of SEQ ID NOS: 1, 2, 3, 4, 5, 6, 7, 8, 9, 10, 11, and 12 (as shown in FIGS. 1-12), and which is effective as a seed-specific promoter.

In other embodiments, the present invention provides an isolated DNA molecule comprising: a) a plant promoter region, wherein the promoter region is any of the promoter regions of the present invention described above; and b) a heterologous gene operably linked to the promoter region. Preferably, the promoter region is selected from the group consisting of SEQ ID NOS: 1, 2, 3, 4, 5, 6, 7, 8, 9, 10, 11, and 12 (as shown in FIGS. 1-12), and more preferably, the promoter region is selected from the group consisting of SEQ ID NOS: 1, 2, 3, 4, 10, and 12. In certain embodiments, the DNA molecule further comprises a 3' non-translated DNA sequence which functions in plant cells to cause the addition of polyadenylated ribonucleotides to the 3' end of an mRNA sequence transcribed from the heterologous gene (in other words, a termination sequence).

In certain embodiments, the present invention provides an expression vector comprising a DNA molecule, wherein the DNA molecule comprises: a) a plant promoter region, wherein the promoter region is any of the promoter regions of the present invention described above; and b) a heterologous gene operably linked to the promoter region. Preferably, the promoter region is selected from the group consisting of SEQ ID NOS: 1, 2, 3, 4, 5, 6, 7, 8, 9, 10, 11, and 12 (as shown in FIGS. 1-12); more preferably, the promoter region is selected from the group consisting of SEQ ID NOS: 1, 2, 3, 4, 10, and 12.

In some embodiments, the present invention provides a transgenic plant cell comprising a DNA molecule, wherein the DNA molecule comprise: a) a plant promoter region, wherein the promoter region is any of the seed-specific promoter regions of the present invention as described above; and b) a heterologous gene operably linked to the promoter region. In other embodiments, the present invention provides a transgenic plant comprising a DNA molecule, wherein the DNA molecule comprises: a) a plant promoter region, wherein the promoter region is any of the promoter regions of the present invention as described above and b) a heterologous gene operably linked to the promoter region. In other embodiments, the present invention provides a transgenic seed comprising a DNA molecule, wherein the DNA molecule comprises: a) a plant promoter region, wherein the promoter region is any of the promoter regions of the present invention as described above; and b) a heterologous gene operably linked to the promoter region. In any of these embodiments, the promoter region preferably selected from the group consisting of SEQ ID NOS: 1, 2, 3, 4, 5, 6, 7, 8, 9, 10, 11, and 12 (as shown in FIGS. 1-12); more preferably, the promoter region is selected from the group consisting of SEQ ID NOS: 1, 2, 3, 4, 10, and 12.

In some embodiments, the present invention provides a method for identifying a seed-specific promoter, comprising: a) providing sequences for a set of ESTs, wherein the ESTs are expressed in developing plant seed tissue; b) analyzing the ESTs by micro array analysis to determine which ESTs are preferentially expressed in developing plant seed tissues; c) selecting at least one EST which is preferentially expressed in developing plant seed tissues; d) identifying a genome sequence which corresponds to the at least one EST; e) analyzing a flanking sequence of the genome sequence to identify a seed-specific promoter region. In particular embodiments, the method further comprises f) characterizing the effectiveness of the identified promoter region to specifically express a gene in a transgenic plant seed tissue.

In certain embodiments, the present invention provides a method for identifying a seed-specific promoter, comprising: a) providing at least a partial genomic sequence of a plant; b) analyzing the sequence for regions which are homologous to at least one nucleic acid sequence selected from the group consisting of SEQ ID NOS: 1, 2, 3, 4, 5, 6, 7, 8, 9, 10, 11, and 12 (as shown in FIGS. 1-12), to identify a seed-specific promoter. In particular embodiments, the method further comprises c) characterizing the effectiveness of the identified promoter region to specifically express a gene in a transgenic plant seed tissue.

In other embodiments, the present invention provides a method for identifying a seed-specific promoter, comprising: a) providing at least a partial first genomic sequence of a first plant, and b) analyzing the first genomic sequence for regions which are homologous to regions of a second genome sequence of a second plant, wherein the plant is *Arabidopsis* and wherein the regions are selected from the group of regions consisting of 65,745-6,103; 32,165-32,525; 2559-243, 67,515-7,329; 67,229-67,048; 27,709-28,066; 8408-8025; 68,590-68,226; 82,725-82,350; 18,058-17,673; 52,852-52,660; 52,589-52,400; 52,096-52,065; 14,510-14,37; 14,289-14,106; 14,033-13,975; 73,712-73,648; 72,555-73,400; and 73,308-73,153; c) identifying at least a first region from the first plant genomic sequence with homology to at least a second region of the second plant genomic sequence; and d) identifying a 5' flanking sequence to the first region to identify a seed-specific promoter. In particular embodiments, the method further comprises e) characterizing the effectiveness of the identified promoter region to specifically express a gene in a transgenic plant seed tissue. In particular embodiments, the present invention provides the isolated DNA molecule identified in step d) above.

In other embodiments, the present invention provides an isolated DNA molecule comprising: a) a seed-specific promoter region identified according to any of the methods of the present invention as described above; and b) a heterologous gene. In some embodiments, the isolated DNA molecule further comprises a 3' non-translated DNA sequence which functions in plant cells to cause the addition of polyadenylated ribonucleotides to the 3' end of an mRNA sequence transcribed from the heterologous gene (in other words, a termination sequence). In other embodiments, the present invention provides expression vectors comprising the DNA molecule comprising: a) a seed-specific promoter region identified according to any of the methods of the present invention as described above; and b) a heterologous gene. In particular embodiments, the present invention provides transgenic plant cells comprising the DNA molecule comprising: a) a seed-specific promoter region identified according to any of the methods of the present invention as described above; and b) a heterologous gene. In other embodiments, the present invention provides transgenic plants comprising the DNA molecule comprising: a) a seed-specific promoter region identified according to any of the methods of the present invention as described above; and b) a heterologous gene. In certain embodiments, the present invention provides transgenic plant seeds, comprising the DNA molecule comprising: a) a seed-specific promoter region identified according to any of the methods of the present invention as described above; and b) a heterologous gene.

In other embodiments, the present invention provides methods of producing a product of interest in a plant seed, comprising: a) providing a transgenic plant comprising a nucleic acid sequence encoding the product of interest operably linked to a promoter region, where the promoter region is any of the seed-specific promoter regions of the present invention as described above or identified by any of the methods of the present invention as described above; and b) growing the plant under conditions such that the product is produced in a seed of the plant. Preferably, the promoter region is selected from the group consisting of SEQ ID NOS: 1, 2, 3, 4, 5, 6, 7, 8, 9, 10, 11, and 12 (as shown in FIGS. 1-12); more preferably, the promoter region is selected from the group consisting of SEQ ID NOS: 1, 2, 3, 4, 10, and 12.

In some embodiments, the present invention provides methods of producing a protein of interest in a plant seed, comprising: a) providing a transgenic plant comprising a nucleic acid sequence encoding the protein of interest operably linked to a promoter region, where the promoter region is any of the seed-specific promoter regions of the present invention as described above or identified by any of the methods of the present invention as described above; and b) growing the plant under conditions such that the protein is produced in seeds of the plant. Preferably, the promoter region is selected from the group consisting of SEQ ID NOS: 1, 2, 3, 4, 5, 6, 7, 8, 9, 10, 11, and 12 (as shown in FIGS. 1-12); more preferably, the promoter region is selected from the group consisting of SEQ ID NOS: 1, 2, 3, 4, 10, and 12.

In particular embodiments, the present invention provides methods of controlling expression of a nucleic acid sequence of interest in a plant, comprising: a) providing a transgenic plant comprising a nucleic acid sequence encoding the product of interest operably linked to a promoter region, where the promoter region is any of the seed-specific promoter regions of the present invention as described above or identified by any of the methods of the present invention as described above; and b) growing the plant under conditions such that the nucleic acid sequence is expressed in a seed of the plant. Preferably, the promoter region is selected from the group consisting of SEQ ID NOS: 1, 2, 3, 4, 5, 6, 7, 8, 9, 10, 11, and 12 (as shown in FIGS. 1-12); more preferably, the promoter region is selected from the group consisting of SEQ ID NOS: 1, 2, 3, 4, 10, and 12.

DESCRIPTION OF THE FIGURES

FIG. 1 shows the nucleic acid sequence of promoter region P1 of gene 1 (SEQ ID NO: 1).

FIG. 2 shows the nucleic acid sequence of promoter region P3 of gene 3 (SEQ ID NO: 2).

FIG. 3 shows the nucleic acid sequence of promoter region P4 of gene 4 (SEQ ID NO: 3).

FIG. 4 shows the nucleic acid sequence of promoter region P6 of gene 6 (SEQ ID NO: 4).

FIG. 5 shows the nucleic acid sequence of promoter region P7 of gene 7 (SEQ ID NO: 5).

FIG. 6 shows the nucleic acid sequence of promoter region P9 of gene 9 (SEQ ID NO: 6).

FIG. 7 shows the nucleic acid sequence of promoter region P13 of gene 13 (SEQ ID NO: 7).

FIG. 8 shows the nucleic acid sequence of promoter region P14 of gene 14 (SEQ ID NO: 8).

FIG. 9 shows the nucleic acid sequence of promoter region P15 of gene 15 (SEQ ID NO: 9).

FIG. 10 shows the nucleic acid sequence of promoter region P16 of gene 16 (SEQ ID NO: 10).

FIG. 11 shows the nucleic acid sequence of promoter region P17 of gene 17 (SEQ ID NO: 11).

FIG. 12 shows the nucleic acid sequence of promoter region P19 of gene 19 (SEQ ID NO: 12).

FIG. 15 shows the nucleic acid sequence of the promoter region P6 of gene 6 (SEQ ID NO: 25), with an inverted repeat indicated by underlining (SEQ ID NO: 26). The BLAST result of the sequence (SEQ ID NO: 26) blasted against its reverse complementary sequence (SEQ ID NO: 61) is also shown.

FIG. 16 shows the nucleic acid sequence of the promoter region P14 of gene 14 (SEQ ID NO: 27), with an inverted repeat indicated by underlining (SEQ ID NO: 28). The BLAST result of the sequence (SEQ ID NO: 28) blasted against its reverse complementary sequence (SEQ ID NO: 62) is also shown.

FIG. 17 shows the nucleic acid sequence of the promoter region P16 of gene 16 (SEQ ID NO: 29), with an inverted repeat indicated by underlining (SEQ ID NO: 30). The BLAST result of the sequence (SEQ ID NO: 30) blasted against its reverse complementary sequence (SEQ ID NO: 63) is also shown.

FIGS. 18A and 18B show Table 2, "Selected Seed-Specific Genes." The selected ESTs and their predicted protein sequences were blasted against protein and DNA sequence databases of NCBI, to identify a possible function of each gene and its corresponding *Arabidopsis* genome sequence.

FIGS. 19A, 19B, and 19C show Table 3, "Primers for PCR Amplification of 12 Promoter Regions." Provided in Table 3 is the name, sequence, position, REs, T(° C.), Length 1, and Length 2. Position is the distance from the best position (for reverse primers, it is ATG). REs is the included restriction enzyme site. T(° C.) is the annealing temperature. Length 1 is the length of the sequences existing in the genomic sequences. Length 2 is the full length.

DEFINITIONS

Figure 13:
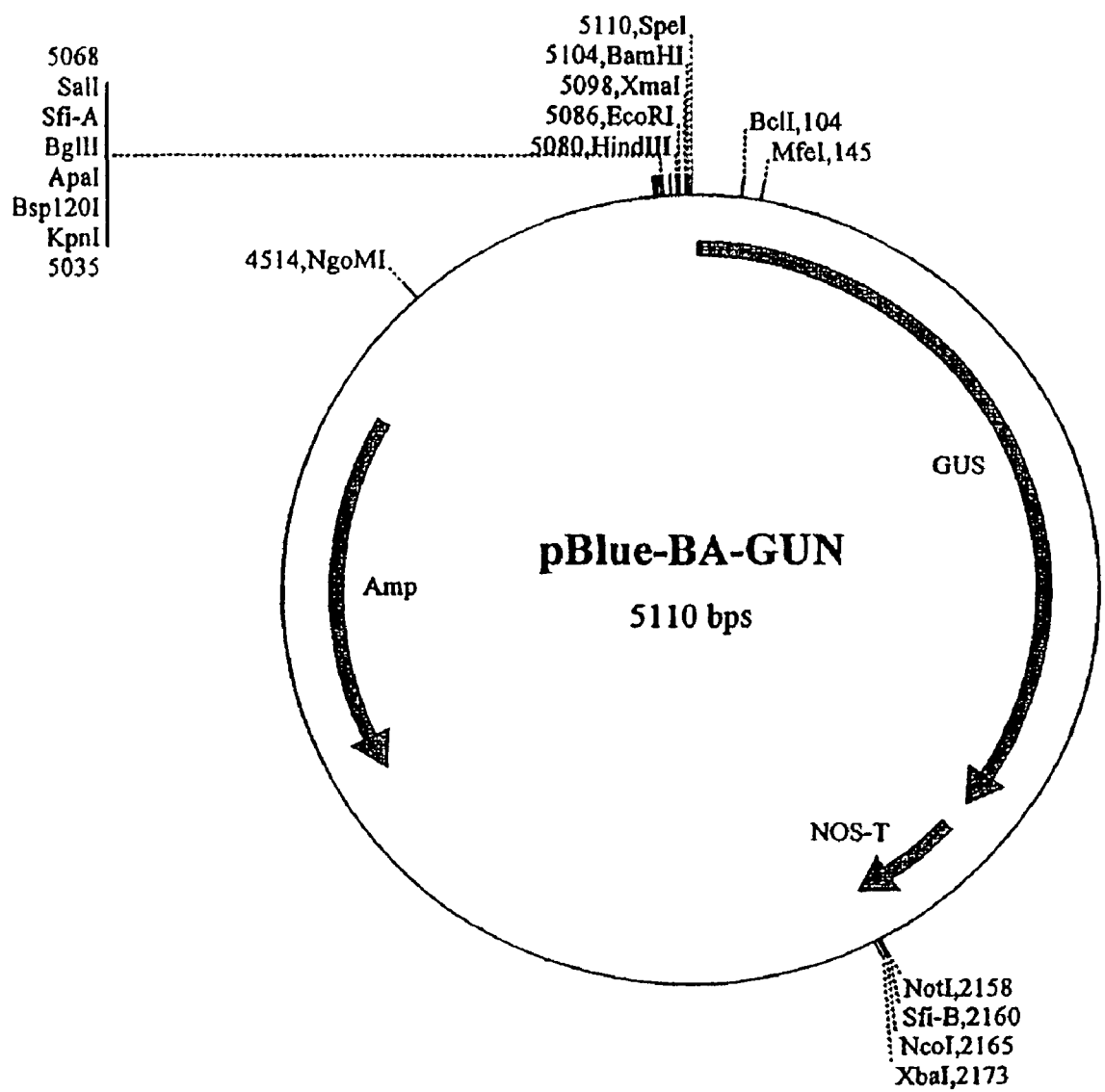
FIG. 13 shows the map of the vector pBlue-BA-GUN.

To facilitate an understanding of the present invention, a number of terms and phrases as used herein are defined below:

The term "plant" is used in it broadest sense. It includes, but is not limited to, any species of woody, ornamental or decorative, crop or cereal, fruit or vegetable plant, and photosynthetic green algae (for example, *Chlamydomonas reinhardtii*). It also refers to a plurality of plant cells which are largely differentiated into a structure that is present at any stage of a plant's development. Such structures include, but are not limited to, a fruit, shoot, stem, leaf, flower petal, etc.

The term "plant tissue" includes differentiated and undifferentiated tissues of plants including those present in roots, shoots, leaves, pollen, seeds and tumors, as well as cells in culture (for example, single cells, protoplasts, embryos, callus, etc.). Plant tissue may be in planta, in organ culture, tissue culture, or cell culture. The term "plant part" as used herein refers to a plant structure or a plant tissue. The term "seed" as used herein includes all tissues which result from the development of a fertilized plant egg; thus, it includes a matured ovule containing an embryo and stored nutrients, as well as the integument or integuments differentiated as the protective seed coat, or testa. The nutrients in seed tissues may be stored in the endosperm or in the body of the embryo, notably in the cotyledons, or both.

The term "crop" or "crop plant" is used in its broadest sense. The term includes, but is not limited to, any species of plant or algae edible by humans or used as a feed for animals or used, or consumed by humans, or any plant or algae used in industry or commerce.

The term "oil-producing species" refers to plant species which produce and store triacylglycerol in specific organs, primarily in seeds. Such species include but are not limited to soybean (*Glycine max*), rapeseed and canola (including *Brassica napus* and *B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The group also includes non-agronomic species which are useful in developing appropriate expression vectors such as tobacco, rapid cycling *Brassica* species, and *Arabidopsis thaliana*, and wild species which may be a source of unique fatty acids.

The term plant cell "compartments or organelles" is used in its broadest sense. The term includes but is not limited to, the endoplasmic reticulum, Golgi apparatus, trans Golgi network, plastids, sarcoplasmic reticulum, glyoxysomes, mitochondrial, chloroplast, and nuclear membranes, and the like.

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein.

The term "portion" or "fragment" when used in reference to a protein (as in "a portion of a given protein") refers to fragments of that protein. The fragments may range in size from four amino acid residues to the entire amino sequence minus one amino acid.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences includes those obtained from the same or from different species of organisms.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferrably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (for example, 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (for example, replacement of a glycine with a tryptophan). Similar minor variations may also include amino acid deletions or insertions in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "gene" refers to a nucleic acid (for example, DNA or RNA) sequence that comprises coding sequences necessary for the production of an RNA, or a polypeptide or its precursor. A functional polypeptide can be encoded by a full length coding sequence or by any portion of the coding sequence as long as the desired activity or functional properties (for example, enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

The term "heterologous" when used in reference to a gene refers to a gene that is not in its natural environment (in other words, has been altered by the hand of man). For example, a heterologous gene includes a gene from one species introduced into another species. A heterologous gene also includes a gene native to an organism that has been altered in some way (for example, mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (for example, genes expressed in loci where the gene is not normally expressed).

The term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The term "nucleotide sequence of interest" or "nucleic acid sequence of interest" refers to any nucleotide sequence (for example, RNA or DNA), the manipulation of which may be deemed desirable for any reason (for example, treat disease, confer improved qualities, etc.), by one of ordinary skill in the art. Such nucleotide sequences include, but are not limited to, coding sequences of structural genes (for example, reporter genes, selection marker genes, oncogenes, drug resistance genes, growth factors, etc.), and non-coding regulatory sequences which do not encode an mRNA or protein product (for example, promoter sequence, polyadenylation sequence, termination sequence, enhancer sequence, etc.).

The term "structural" when used in reference to a gene or to a nucleotide or nucleic acid sequence refers to a gene or a nucleotide or nucleic acid sequence whose ultimate expression product is a protein (such as an enzyme or a structural protein), an rRNA, an sRNA, a tRNA, etc.

The term "fragment" or "portion" when used in reference to a an oligonucleotide sequence or nucleic acid sequence refers to a length of the sequence which is less than the entire length is it occurs naturally (for example, as a DNA, RNA, or cDNA molecule). The fragments may range in size from a few nucleotides to the entire nucleic sequence minus one nucleotide. Thus, "a nucleotide comprising at least a portion of a gene" may comprise fragments of the gene or the entire gene The term "an oligonucleotide having a nucleotide sequence encoding a gene" or "a nucleic acid sequence encoding" a specified gene product refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (in other words, the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (in other words, a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (in other words, identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (in other words, the hybridization) of a sequence which is completely homologous to a target under conditions of low stringency. This is not to say that conditions of low stringency are such that non-specific binding is permitted; low stringency conditions require that the binding of two sequences to one another be a specific (in other words, selective) interaction. The absence of non-specific binding may be tested by the use of a second target which lacks even a partial degree of complementarity (for example, less than about 30% identity); in the absence of non-specific binding the probe will not hybridize to the second non-complementary target.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (in other words, a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (in other words, gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math 2: 482 (1981)) by the homology alignment algorithm of Needleman and Wunsch (Needleman and Wunsch, J. Mol. Biol. 48:443 (1970)), by the search for similarity method of Pearson and Lipman (Pearson and Lipman, Proc. Natl. Acad. Sci. (U.S.A.) 85:2444 (1988)), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (in other words, resulting in the highest percentage of homology over the comparison window) generated by the various methods is selected. The term "sequence identity" means that two polynucleotide sequences are identical (in other words, on a nucleotide-by-nucleotide basis) over the window of comparison. The term "percentage of sequence identity" is calculated by comparing two optimally aligned sequences over the window of comparison, determining the number of positions at which the identical nucleic acid base (for example, A, T, C, G, U, or I) occurs in both sequences to yield the number of matched positions, dividing the number of matched positions by the total number of positions in the window of comparison (in other words, the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

The term "substantially homologous" when used in reference to a double-stranded nucleic acid sequence such as a cDNA or genomic clone refers to any probe that can hybridize to either or both strands of the double-stranded nucleic acid sequence under conditions of low to high stringency as described below.

The term "substantially homologous" when used in reference to a single-stranded nucleic acid sequence refers to any probe that can hybridize (in other words, it is the complement of) the single-stranded nucleic acid sequence under conditions of low to high stringency as described below.

The term "hybridization" refers to the pairing of complementary nucleic acids. Hybridization and the strength of hybridization (in other words, the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41$ (% G+C), when a nucleic acid is in aqueous solution at 1 M NaCl (See for example, Anderson and Young, Quantitative Filter Hybridization, in *Nucleic Acid Hybridization* (1985)). Other references include more sophisticated computations that take structural as well as sequence characteristics into account for the calculation of $T_m$.

The term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent (50×Denhardt's contains per 500 ml: 5 g Ficoll (Type 400, Pharmacia), 5 g BSA (Fraction V; Sigma)) and 100 μg/ml denatured salmon sperm DNA followed by washing in a solution comprising 5×SSPE, 0.1% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 1.0×SSPE, 1.0% SDS at 42° C. when a probe of about 500 nucleotides in length is employed.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (for example, the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (for example, increasing the temperature of the hybridization and/or wash steps, the use of formamide in the hybridization solution, etc.).

"Amplification" is a special case of nucleic acid replication involving template specificity. It is to be contrasted with non-specific template replication (in other words, replication that is template-dependent but not dependent on a specific template). Template specificity is here distinguished from fidelity of replication (in other words, synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q-replicase, MDV-1 RNA is the specific template for the replicase (Kacian et al., Proc. Natl. Acad. Sci. USA, 69:3038 (1972)). Other nucleic acid will not be replicated by this amplification enzyme. Similarly, in the case of T7 RNA polymerase, this amplification enzyme has a stringent specificity for its own promoters (Chamberlin et al., Nature, 228:227 (1970)). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 (1989)). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press (1989)).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (in other words, in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "probe" refers to an oligonucleotide (in other words, a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (for example, ELISA, as well as enzyme-based histochemical assays), fluorescent, radioactive, and luminescent systems. It is not intended that the present invention be limited to any particular detection system or label.

The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (in other words, denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (for example, hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

The term "gene expression" refers to the process of converting genetic information encoded in a gene into RNA (for example, mRNA, rRNA, tRNA, or snRNA) through "transcription" of the gene (in other words, via the enzymatic action of an RNA polymerase), and into protein, through "translation" of mRNA. Gene expression can be regulated at many stages in the process. "Up-regulation" or "activation" refers to regulation that increases the production of gene expression products (in other words, RNA or protein), while "down-regulation" or "repression" refers to regulation that decrease production. Molecules (for example, transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" refer to a DNA sequence that is located at the 5' end (in other words precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer, and is typically between about 500 bp and 4 kb in length, and is preferably about 1 to 1.5 kb in length. A promoter region controls or regulates transcription of a gene to which it is operably linked, either naturally or by recombinant nucleic acid technology. A promoter region may include smaller sequences which are effective to control or regulate transcription. One skilled in the art can determine such smaller sequences by creating fragments of decreasing size from a promoter region, and operably linking such fragments to a reporter gene, and determining expression of such constructs in transgenic tissue, as described further herein.

Promoters may be tissue specific or cell specific. The term "tissue specific" as it applies to a promoter refers to a promoter that is capable of directing selective expression of a nucleotide sequence of interest to a specific type of tissue (for example, seeds) in the relative absence of expression of the same nucleotide sequence of interest in a different type of tissue (for example, leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (for example, detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, for example, immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (for example, peroxidase conjugated) secondary antibody which is specific for the primary antibody is allowed to bind to the sectioned tissue and specific binding detected (for example, with avidin/biotin) by microscopy.

A promoter is "effective" as a tissue specific or cell type promoter when expression in the presence of the promoter is greater in the tissue or cell type than expression in the presence of the promoter in other tissues or cell types. Preferably, the greater level of expression is at least about two-fold greater; more preferably, it is at least about four-fold greater; and most preferably, it is at least about ten-told greater. An effective promoter may comprise all of the promoter region, or a modification or fragment of a promoter region, or a motif of a promoter region.

A "seed-specific promoter" is a promoter which controls or regulates expression of a gene to which it is operably linked in a seed or seed tissue; such expression may occur in developing seed tissue only, at differing times or levels, or in mature seed tissue, or in both. Preferably, expression of the gene in seed tissue is greater than in non-seed tissue when under control of a seed-specific promoter. Preferably, the greater level of expression is at least about two-fold greater; more preferably, it is at least about four-fold greater; and most preferably, it is at least about ten-fold greater.

A gene which is preferentially expressed in seeds or seed tissue is expressed at a higher level than it is in non-seed tissue. Preferably, expression of the gene in seed tissue is greater than in non-seed tissue. Preferably, the greater level of expression is at least about two-fold greater; more preferably, it is at least about four-fold greater; and most preferably, it is at least about ten-fold greater Promoters may be constitutive or inducible. The term "constitutive" when made in reference to a promoter means that the promoter is capable of directing transcription of an operably linked nucleic acid sequence in the absence of a stimulus (for example, heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see for example, U.S. Pat. No. 5,352,605, incorporated herein by reference), mannopine synthase, octopine synthase (ocs), superpromoter (see for example, WO 95/14098), and ubi3 (see for example, Garbarino and Belknap, Plant Mol. Biol. 24:119-127 (1994)) promoters. Such promoters have been used successfully to direct the expression of heterologous nucleic acid sequences in transformed plant tissue.

In contrast, an "inducible" promoter is one which is capable of directing a level of transcription of an operably linked nucleic acid sequence in the presence of a stimulus (for example, heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (in other words, molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (for example, the first and second genes can be from the same species, or from different species).

The term "naturally linked" or "naturally located" when used in reference to the relative positions of nucleic acid sequences means that the nucleic acid sequences exist in nature in the relative positions.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual,* 2nd ed., Cold Spring Harbor Laboratory Press, New York (1989) pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook, supra, at 16.6-16.7).

The term "termination signal" or "termination sequence" refers to a 3' non-translated DNA sequence which functions in plant cells to cause the addition of polyadenylated ribonucleotides to the 3' end of an mRNA sequence transcribed from a gene; the gene may be an endogenous or native gene, or it may be a heterologous gene. The termination sequence may be endogenous or heterologous to the gene.

The term "vector" refers to nucleic acid molecules that transfer DNA segment(s) from one cell to another. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (in other words, particle bombardment) and the like.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 (1973)), has been modified by several groups to optimize conditions for particular types of cells. The art is well aware of these numerous modifications.

The terms "infecting" and "infection" when used with a bacterium refer to co-incubation of a target biological sample, (for example, cell, tissue, etc.) with the bacterium under conditions such that nucleic acid sequences contained within the bacterium are introduced into one or more cells of the target biological sample.

The term "*Agrobacterium*" refers to a soil-borne, Gram-negative, rod-shaped phytopathogenic bacterium which causes crown gall. The term "*Agrobacterium*" includes, but is not limited to, the strains *Agrobacterium tumefaciens*, (which typically causes crown gall in infected plants), and *Agrobacterium rhizogens* (which causes hairy root disease in infected host plants). Infection of a plant cell with *Agrobacterium* generally results in the production of opines (for example, nopaline, agropine, octopine etc.) by the infected cell. Thus, *Agrobacterium* strains which cause production of nopaline (for example, strain LBA4301, C58, A208, GV3101) are referred to as "nopaline-type" *Agrobacteria; Agrobacterium* strains which cause production of octopine (for example, strain LBA4404, Ach5, B6) are referred to as "octopine-type" *Agrobacteria*; and *Agrobacterium* strains which cause production of agropine (for example, strain EHA105, EHA101, A281) are referred to as "agropine-type" *Agrobacteria*.

The terms "bombarding, "bombardment," and "biolistic bombardment" refer to the process of accelerating particles towards a target biological sample (for example, cell, tissue, etc.) to effect wounding of the cell membrane of a cell in the target biological sample and/or entry of the particles into the target biological sample. Methods for biolistic bombardment are known in the art (for example, U.S. Pat. No. 5,584,807, the contents of which are incorporated herein by reference), and are commercially available (for example, the helium gas-driven microprojectile accelerator (PDS-1000/He, BioRad).

The term "microwounding" when made in reference to plant tissue refers to the introduction of microscopic wounds in that tissue. Microwounding may be achieved by, for example, particle bombardment as described herein.

The term "transgene" refers to a foreign gene that is placed into an organism by the process of transfection. The term "foreign gene" refers to any nucleic acid (for example, gene sequence) that is introduced into the genome of an organism by experimental manipulations and may include gene sequences found in that organism so long as the introduced gene does not reside in the same location as does the naturally-occurring gene.

The term "transgenic" when used in reference to a plant or fruit or seed (in other words, a "transgenic plant" or "transgenic fruit" or a "transgenic seed") refers to a plant or fruit or seed that contains at least one heterologous or foreign gene in one or more of its cells. The term "transgenic plant material" refers broadly to a plant, a plant structure, a plant tissue, a plant seed or a plant cell that contains at least one heterologous gene in one or more of its cells.

The term "host cell" refers to any cell capable of replicating and/or transcribing and/or translating a heterologous gene. Thus, a "host cell" refers to any eukaryotic or prokaryotic cell (for example, bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "selectable marker" refers to a gene which encodes an enzyme having an activity that confers resistance to an antibiotic or drug upon the cell in which the selectable marker is expressed, or which confers expression of a trait which can be detected (for example., luminescence or fluorescence). Selectable markers may be "positive" or "negative." Examples of positive selectable markers include the neomycin phosphotransferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, luciferase (See for example, deWet et al., Mol. Cell. Biol. 7:725 (1987) and U.S. Pat. Nos. 6,074, 859; 5,976,796; 5,674,713; and 5,618,682; all of which are incorporated herein by reference), green fluorescent protein (for example, GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

The term "wild-type" when made in reference to a nucleic acid sequence refers to a nucleic acid sequence which has the characteristics of the sequence isolated from a naturally occurring source. The term "wild-type" when made in reference to a gene product refers to a gene product which has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is that which is most frequently observed in a population and is thus arbitrarily designated the "normal" or "wild-type" form of the gene. In contrast, the term "modified" or "mutant" when made in reference to a nucleic acid sequence (such as a regulatory sequence or a sequence encoding a gene) or to a gene product refers, respectively, to a nucleic acid sequence or to a gene product which displays modifications in sequence and/or functional properties (in other words, altered characteristics) when compared to the wild-type gene or gene product. Modifications include additions or deletions of the units making up the nucleic acid sequence or gene product (a unit is, for example, a nucleotide), or substitutions of at least one of the units. It is noted that naturally-occurring mutants can be isolated; these are identified by the fact that they have altered characteristics when compared to the wild-type nucleic acid sequence or gene product.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, in other words, at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "overexpression" refers to the production of a gene product in transgenic organisms that exceeds levels of production in normal or non-transformed organisms. The term "cosuppression" refers to the expression of a foreign gene which has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. (1989) *Molecular Cloning: A Laboratory Manual* (Cold Spring Harbor Press, NY), pp 9.31-9.58).

The term "Northern blot analysis" and "Northern blot" and "Northern" refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. (1989) supra, pp 7.39-7.52).

The terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabelled antibodies.

The term "antigenic determinant" refers to that portion of an antigen that makes contact with a particular antibody (in other words, an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (in other words, the "immunogen" used to elicit the immune response) for binding to an antibody.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (for example, a gene) is found on the host cell chromosome in proximity to neighboring genes; RNA sequences, such as a specific mRNA sequence encoding a specific protein, are found in the cell as a mixture with numerous other mRNA s which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (in other words, the oligonucleotide may single-stranded), but may contain both the sense and antisense strands (in other words, the oligonucleotide may be double-stranded).

The term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

GENERAL DESCRIPTION OF THE INVENTION

The present invention relates to novel seed specific promoter regions. The present invention further comprises methods of producing proteins and other products of interest and methods of controlling expression of nucleic acid sequences of interest using the seed specific promoter regions.

I. Seed-Specific Promoter Regions

In some embodiments, the present invention provides compositions comprising novel seed specific promoter regions from *Arabidopsis thaliana*. In some embodiments, the present invention provides the nucleic acid sequences of the seed-specific promoter regions P1, P3, P4, P6, P7, P9, P13, P14, P15, P16, P17, and P19 (SEQ ID NOS: 1-12, as shown in FIGS. 1-12), and their functional equivalents. The discovery of these promoter is described below. In other embodiments, the present invention provides sequences that hybridize to the seed-specific promoter regions P1, P3, P4, P6, P7, P9, P13, P14, P15, P16, P17, and P19 (for example, under conditions of low to high stringency). Such sequences are characterized for functional equivalence using the methods described below and exemplified in Example 3, Sections D-F. In other embodiments, the present invention provides nucleic acid sequences of plant promoter regions naturally located upstream to structural DNA sequences which are identified as homologous to the genes naturally under control of promoter regions P1, P3, P4, P6, P7, P9, P13, P14, P15, P16, P17, and P19. In yet other embodiments, the present invention provides fragments or modifications of seed-specific promoter regions P1, P3, P4, P6, P7, P9, P13, P14, P15, P16, P17, and P19; these sequences are characterized for functional equivalence using the methods described below and exemplified in Example 3, Sections D-F.

The discovery of the seed-specific promoter regions is a result of a genome wide analysis of gene expression in developing seeds of *Arabidopsis thaliana*. This discovery process can be divided into several stages; the first is the isolation and analysis of expressed sequence tags (ESTs) and their associated cDNAs from developing seeds. The next stage is a microarray analysis of a selected subset of the ESTs; this analysis is used to broadly analyze the expression of several thousand genes during seed development, to identify tissue-specific expression patterns, and to identify certain genes for further analysis. The next stage is to select a second EST subset within the initial subset, where the second subset comprises ESTs which are identified as highly expressed and seed-specific. In stage three, genome sequences which match the ESTs noted above are identified from the *Arabidopsis* genome. The flanking sequences of these genes are analyzed by software programs, such as GeneScan, GeneStart, and Genefinder (which are publicly available gene prediction programs accessible through the site arabidopsis.org/geneid.html) to predict the associated promoter regions. Next, a subset of the gene promoter regions is identified and characterized. Identification is based generally on: a) comparison to protein sequences, if available; b) high probability of ATG prediction; and c) high probability of gene prediction, and characterized. Characterization includes determining the effectiveness of each promoter region to control expression of a reporter gene in transgenic seed tissue. Characterization also includes determining the effectiveness of fragments or modifications to a promoter region to control expression of a reporter gene in transgenic seed tissue. Additional seed-specific promoter regions are provided by identifying promoter regions naturally located upstream to structural DNA sequences which are identified as homologous to the genes naturally under control of promoter regions P1, P3, P4, P6, P7, P9, P13, P14, P15, P16, P17, and P19.

The resulting promoter regions of the present invention are of general utility for producing seed specific products. It is understood that the method of discovering seed specific promoters, outlined above and described below in detail for *Arabidopsis thaliana*, can be applied to discover additional seed-specific and tissue-specific promoter regions from *Arabidopsis thaliana*, as well as to discover seed-specific promoter regions from other plants.

A. EST Isolation and Analysis

The first stage in the discovery of seed-specific promoter regions is the isolation and analysis of expressed sequence tags (ESTs) and their associated cDNAs from developing seeds; an exemplary procedure is described in Example 1. A cDNA library is constructed from developing seeds by harvesting immature seeds at a selected number of time points during development; typically these points are a certain number of days after flowering (DAF). RNA is extracted from the seed tissue, and a cDNA library prepared by well known methods. The cDNA library is amplified at least once to reach an appropriate titre. Selected cDNA clones are then sequences, and the sequences are then used for similarity searches against GenBank, the contigs analyzed, and a database developed.

1. Single Pass Sequencing of 10,565 cDNAs from Developing Seeds

Although over 45,000 *Arabidopsis* ESTs have already been deposited in dbEST (release 030300) (Boguski et al., Nat. Genet., 4:332-333 (1993)), it is believed that these are not representative of genes specifically expressed in developing seeds, because siliques but not isolated developing seeds had previously been used as source of the cDNAs. In order to obtain seed-specific promoter regions, a single-pass sequencing of cDNAs was derived exclusively from developing *Arabidopsis* seeds, where the developing seeds were harvested from 5-13 days after flowering as described in Example 1.

The cDNAs were sequenced in two different data sets. From data set I, 4643 clones (51%) were sequenced and analyzed with BLASTX. From data set II, 5922 clones (32%) were sequenced and analyzed. The average read lengths after trimming were 393 bp for clones from data set 1 and 259 bp for clones from data set II. Taken together, 10,565 clones were analyzed at the level of BLASTX searches, which is equivalent to 38% of the clones on the filters. These clones provide the basis for the classification of ESTs and the expression analysis. A total of 11,860 sequences were generated and kept in a FASTA file (complete raw data set), which include 1,133 sequence runs from the 3' ends of selected clones, a small number of repeats, and clones for which only poor sequence is available. The raw data as well as annotations were deposited in a database of the present invention according to clone identifiers (derived from the clone location in microtitre plates).

2. Classification of ESTs According to Predicted Function

To obtain qualitative information about the ESTs, each sequence was translated into all six reading frames and the translation products were searched (BLASTX) against the non-redundant protein database of GenBank. The top scoring hits were automatically extracted and manually annotated according to the description of the sequence(s) returned by BLASTX. It must be emphasized that this procedure provides only tentative clues towards the function of the encoded proteins, due to the fact that relatively few of the descriptions associated with GenBank entries have been currently verified by wet-lab experiments (Boguski, Science, 286:453-455 (1999)). Furthermore, two classes of the clones, identified as possessing "non significant homology" (NSH) or "unidentified function" (UF), represent approximately 40% of the clones. Based upon further analysis, it is believed that approximately 24% of the clones in the seed database of the present invention encode novel proteins 3. The Number of Novel ESTs and of Genes Represented in the Seed EST Set To evaluate the effectiveness of isolating and sequencing cDNAs from developing seeds to provide seed-specific novel ESTs not present in the current public data base, the entire 5' sequence data set of the present invention was compared against the *Arabidopsis* set in dbEST. Of the 10,485 BLASTN results returned, 6,360 (60.9%) showed BLASTN scores (high scoring segment pairs, HSP) of less than 50. Based on these scores it is estimated that approximately 60% of the ESTs of the present invention are not represented in the public *Arabidopsis* EST set, and therefore many of these probably correspond to genes specifically expressed in developing seeds of *Arabidopsis*.

Because multiple ESTs can be derived from a single gene, cluster analysis was conducted to assemble individual sequences in the database into contigs in order to estimate the number of genes giving rise to the ESTs. Of the 11,860 sequences in the raw sequencing file, 7577 (64%) assembled into 1,570 contigs and 4,283 (36%) remained as singletons. Thus, the maximal number of unique cDNAs represented in the entire data set is 5,829. To estimate how many genes are represented in the data set which may be specifically expressed in developing seeds, the number of contigs and singletons represented by the 6,360 ESTs not represented in the public data set was determined. These were 742 contigs and 2270 singletons representing a maximal number of 3012 genes. Thus, based on this analysis, up to 50% of all genes represented by the data set of the present invention are thought to be specifically expressed in seeds, subject to two caveats. First, although in most cases each contig represents one gene, sometimes more than one contig of non-overlapping sequences exist per gene resulting in an overestimation. Second, sometimes closely related gene families cannot be resolved into individual contigs resulting in an underestimation.

4. Mapping ESTs onto the *Arabidopsis* Genome

One step towards determining the exact number of genes represented by ESTs is to map all the ESTs and contig consensus sequences of the present invention onto the *Arabidopsis* genome. For this purpose, a search (BLASTN) of all sequences in the raw sequence file as well as all contig consensus sequences against an *Arabidopsis* genomic sequence subset of all sequences longer than 10 kb was conducted. This genomic sequence subset should primarily contain sequenced BACs, PACs and P1 clones from the "*Arabidopsis* Genome Initiative (AGI)". In the past, this information could only be obtained by direct PCR mapping approaches (Agyare et al., Genome Res., 7:1-9 (1997)) due to the absence of large scale genomic sequence information. Of the 1570 contigs of the present invention, 1,237 (79%) matched (HSP >50) 316 large genomic clones, equivalent to about 4 contigs per genomic clone, and 333 contigs (21%) matched with 1 contig per clone.

5. Abundance of ESTs Derived from Specific Genes

The number of sequences assembled in the contigs gives an indication of the degree of expression of the respective gene in developing seeds. As predicted by the initial classification of individual ESTs, the largest contigs encode seed storage proteins. In agreement with the high demands for protein synthesis in developing seeds, some of the larger contigs can be found for elongation factors involved in. ESTs for proteins possibly involved in storage protein body formation such as vacuolar processing enzyme (Kinoshita et al., Plant Mol. Biol., 29:81-89 (1995)) or proteases in general are highly abundant. Similarly, genes encoding enzymes involved in protein folding such as protein disulfide isomerase genes are highly expressed in seeds (Boston et al., Plant Mol. Biol., 32:191-222 (1996)). Developing embryos of *Arabidopsis* are green. Thus, it is not surprising that ESTs encoding chlorophyll binding proteins are present in high numbers. The most highly abundant enzyme-encoding ESTs are those for S-adenosylmethionine decarboxylase.

Among the largest contigs are 20 for which the consensus sequence either did not have a match in GenBank or which are similar to proteins of unknown function. These provide a pool of novel proteins with a function that is believed to be of special relevance for developing seeds. An obvious class of ESTs which is not represented in this list of largest contigs are those with similarity to transcription factor genes, although the entire data set contains a considerable number of such ESTs (169, 1.6%). Clearly, regulatory genes are not as highly expressed as storage protein genes or genes essential for the biosynthesis of other storage compounds. These observations confirm that the observed abundance of ESTs in each contig or class is in agreement with common knowledge about the biology of plant cells and of developing seeds in particular.

B. Microarray Analysis of a Developing Seed EST Subset

The next stage in the discovery of seed-specific promoter regions is a microarray analysis of a selected subset of the ESTs; this analysis is used to broadly analyze the expression of several thousand genes during seed development, to identify tissue-specific expression patterns, and to identify certain genes for further analysis.

1. Microarray Fabrication

For microarray fabrication, a subset of 2,715 clones was selected from the 5,800 sequences of data set I. These sequences were selected after contig analysis and were selected to avoid redundancy. Nevertheless, some of these ESTs were very similar and are likely to represent the same gene. The number of unique genes represented on the arrays is therefore slightly less than 2,715. A collection of 60 control DNAs was generated. The inserts of the three clone collections were amplified by PCR with vector specific primers. PCR samples which yielded less than 0.2 mg/mL DNA or showed several DNA fragments were re-amplified or replaced with alternative clones. The PCR products were arrayed on and bound to polylysine coated microscope slides. To increase the reliability of the detected signals, each PCR sample was spotted twice in two subarrays resulting in a total array of 7680 data points. The identity of 37 randomly chosen DNA samples was confirmed by re-sequencing their PCR products used for microarray printing and comparing the obtained sequence results with the corresponding EST sequences in the database of the present invention. In all 37 cases, the sequences of the PCR samples matched their original EST sequence. This sequence confirmation increases the confidence in the identity of the DNA elements on the microarrays and makes it unlikely that major errors in the selection of clones or sample plates occurred during sample preparation.

2. Quality Control

To evaluate the reliability of the hybridization experiments, the microarrays contained several control elements. To detect the sensitivity limit and to have an additional control for balancing the intensities of the two channels, nine non-related human cDNA fragments were arrayed on the slides The corresponding in vitro transcribed poly(A)$^+$ RNA species were added to 1.0 μg of the plant tissue mRNA samples as internal standards in decreasing concentrations from 1.0 ng (1:1.0× 10$^{-3}$) to 0.01 ng (1:1.0×10$^{-5}$). The lowest control RNA levels of 7.5×10$^4$ and 1.0×10$^{-5}$ gave in most experiments fluorescence signal intensities (FSI units) higher than two times the local background. Similar detection limits of 1.0×10$^{-5}$ (Ruan et al., Plant J., 15:821-833 (1998)) and 5.0×10$^{-5}$ (Schena et al., Proc. Nat. Acad. Sci. U.S.A., 93:10614-10619 (1996)) were detected by other groups. According to mRNA quantifications from Okamuro et al., The Biochemistry of Plants, 15:1-82 (1989), this detection limit corresponds to approximately 1-2 mRNA copies per cell.

Many Arabidopsis genes belong to gene families, and therefore cross-hybridizations between different members of gene families are an issue in cDNA based microarray experiments. Estimates of the extent of gene families in Arabidopsis range from 15 to 50% and over half of 64 proteins served for lipid metabolism were found to be members of gene families (Mehkedov et al. 2000). To estimate the extent of possible cross-hybridizations between related genes, the threshold of cross-hybridization was detected in each experiment with several specificity controls. These controls included synthetic gene fragments and heterologous sequences from other plant species, which have decreasing sequence identities of 100-60% to three moderately expressed Arabidopsis genes. First, 365 bp synthetic fragments of the Arabidopsis FAD2 gene in three different forms of identical length and constant GC content of 48%, but decreasing nucleotide identities of 100%, 90% and 80%, were synthesized and arrayed. The 100% fragment gave comparably strong signals (generally within 80-90%) to a 1.1 kbp PCR fragment from FAD2, indicating that a target length of 365 bp is sufficient for efficient probe binding in this technique. The 90% identity fragment gave approximately 50% weaker signals compared to the 100% form, whereas the 80% form showed almost no detectable signals, suggesting a cross-hybridization threshold under the conditions of these experiments between 80-90% identity. Cross-reactions with other Arabidopsis transcripts are unlikely, because there are no known Arabidopsis genes which are closely related (>60%) to FAD2 (Okuley et al., J. Plant Cell, 6:147-158 (1994)). The synthetic gene fragments were designed with evenly spaced mismatches. Two other specificity control sets consisted of four ferredoxin sequences and three acyl-ACP-desaturase sequences from other organisms. These contain more variable similarity clusters to the Arabidopsis sequences than the synthetic FAD2 fragments, and showed cross-hybridization thresholds between 60-70%. Based on these experiments, it is clear that some closely related gene family members will not be discriminated. However, with complete availability of the Arabidopsis genome it is possible to assess the approximate extent of potential cross-hybridization. For example, most of the seven known Arabidopsis ACP genes are less than 70% identical and unlikely to cross-hybridize, whereas four of the five members of the stearoyl-ACP desaturase family are >80% identical (Mehkedov et al, 2000). Additional controls, as described in Example 2, monitored for non-specific hybridization, carry-over during printing and for mRNA integrity/probe length.

3. Microarray Hybridizations

To monitor seed-specific gene expressions, mRNA samples from seeds, leaves and roots of Arabidopsis were isolated, and reverse transcribed with oligo-dT primers into first strand cDNA fluorescent probes, as described in Example 2. The mRNA isolated from seeds was the reference to which the samples from leaves and roots were compared. Each tissue comparison was performed at least twice, using in most cases independently isolated RNA samples as starting material. For repeated experiments, the probe pairs contained the fluorochromes Cy3 and Cy5 in opposite orientation. Results of repeated experiments were only used for further analyses if the ratios of all data points on the array showed a correlation coefficient close to one. To eliminate highly variable and therefore less reliable expression data, data was used for further analysis only if at least two experiments showed the same trend of expression. Averaging ratios across experiments was considered a less stringent strategy, because it neglects the variability between measurements (DeRisi et al., Science, 278:680-686 (1997)). This is particularly true when low tissue mass (as with developing Arabidopsis seeds) is a limitation for the number of feasible experiments. For the experiments described here, over 20 hours of dissection of developing seeds from siliques was required to harvest material for a single fluorescent probe.

The data was analysed as a scatter plot of the data for seed vs leaf. It is clear from this representation that the majority of genes analyzed fall near the X-axis and have less than a two fold difference in signal intensity between the leaf and seed probes. Thus, although the microarray was based on a set of ESTs primarily derived from sequencing of a seed cDNA library, the overall expression pattern clearly indicates that a large proportion of seed expressed genes are also expressed in other tissues. These data support the general conclusion based on hybridization analysis of RNA complexity that 60-77% (the majority) of plant genes do not have strong tissue-specific expression (Okamura and Goldberg, 1989; Kamalay et al., Cell, 19:935-946 (1980)). Expression analyses with smaller and non-seed specific arrays from *Arabidopsis* detected comparable amounts of tissue specific (Ruan et al., Plant J., 15:821-833 (1998)) or differentially expressed genes (Desprez et al., Plant J., 14:643-652 (1998); Kehoe et al., Trends Plant Sci., 4:38-41 (1999); Richmond et al., Curr. Opin. Plant Biol., 3:108-116 (2000)).

Nevertheless, the microarrays reveal that a substantial number of genes can be considered seed-specific. In the seed versus leaf co-hybridizations, approximately 30% of the spotted cDNAs showed more than 2 fold stronger signals in seeds, and approximately 12% were expressed more than 10 fold higher in seeds than in leaves (Table 1). In the corresponding seed versus root experiments, similar comparisons yielded 33% and 13% of the genes, respectively. If both tissue comparisons are combined, 25% of genes showed more than 2 fold and 10% more than 10 fold stronger signals in seeds than in leaves or roots. One factor should be noted which influences these numbers. The reliability of the signals used to calculate these ratios was ensured by including only those values which showed fluorescent intensity levels in at least one channel above three times the local background. This high signal to noise ratio and the stringent limit for the ratios of more than two fold in each experiment of both tissue comparisons selects preferentially for genes which are moderate to strongly expressed in seeds and only to a very low extent in the other tissues. This sorting based on high confidence values tends to disregard weakly expressed genes, which generally do not reach a high and stable enough signal to background ratio in several experiments to appear in this list.

TABLE 1

Number of Genes with Seed-specific Expression Patterns

| Expression Ratio[a] | seed/leaf | seed/root | seed/leaf & root |
|---|---|---|---|
| ≧2 | 804 (30%)[b] | 899 (33%) | 688 (25%) |
| ≧4 | 555 (21%) | 615 (23%) | 478 (18%) |
| ≧10 | 325 (12%) | 348 (13%) | 264 (10%) |

[a]Ratio categories. Genes in these categories showed in at least two duplicate experiments ratios above the given thresholds.
[b]Percentage based on 2700 ESTs.

4. Characteristics of the Seed-Expressed Set

The tissue-expression ratios for a number of well-characterized genes and the variability observed in replicated experiments was examined. The set of highly seed-specifically expressed sequences (ratio≧4) contains several seed storage proteins, and a number of other genes which are well known to be predominantly seed expressed. These include oleosins (Abell et al., Plant Cell, 9:1481-1493 (1997)), fatty acid elongase (FAE1) (James et al., Plant Cell, 7:309-319 (1995)), lipoxygenase (Fauconnier et al., Grasas Y Aceites, 46:6-10 (1995)), and other genes. Similarly, the arrays of the present invention included a number of genes involved in photosynthesis and carbon fixation, such as chlorophyll a/b binding protein and the small subunit of RuBisCo. These and other related photosynthetic genes were found to be expressed preferentially in leaves. Thus, the overall reliability of the microarrays was confirmed by obtaining the expected preferential seed or leaf expression patterns for dozens of well-characterized genes.

As described above, the seed-expressed ESTs were classified according to their putative function. Microarray analysis of groups of clones from several categories results in several observations. Only storage proteins stand out as a class with a high proportion of seed-specific sequences. As observed for the overall set of 2600 genes, only a minority of the clones in all other clone categories are seed-specific. Although oil is the major storage reserve in *Arabidopsis* seeds, lipid-biosynthesis related genes were in general only slightly more highly expressed in seeds. Of the 113 genes included on the microarrays which are related to lipid biosynthesis, only 10 were found to occur in the subset with ≧10-fold higher seed vs leaf or root signals. These numbers reflect the fact that lipid biosynthesis is essential for growth of all tissues, and can be considered a "housekeeping" function. The 10 lipid related genes with high seed to leaf/root expression ratios include oleosin, FAE1, and lipases.

Approximately 28 cDNAs with homology to transcription factors, kinases, phosphatases and proteins involved in development were highly seed-specific (ratio≧4). Most of these represent genes which have not previously been characterized at the level of tissue-specific expression. Over 110 cDNAs of the ≧4-fold subset (more than 23%) show no significant homology to known sequences (BLAST score <100) or fall in the category of proteins with unidentified function. Since the sequences of most structural genes are known, it is likely that these sets of new and unidentified seed-specific sequences contain many additional regulatory genes.

5. Identification of New Strong Seed-Specific Promoter Regions

Because EST abundance is in most cases related to mRNA abundance, the sequencing of >10,000 ESTs from a seed cDNA library has provided a set of data which can be used to identify highly expressed genes, as described previously. Microarray data provides additional information on tissue-specificity of gene expression. By combining these two types of data, it is possible to identify genes which are both strongly expressed, and expressed with high tissue-specificity. Of course, many seed storage proteins and other genes are well known to fall into this category. A number of additional such candidates, which have both high EST abundance and high seed-specificity based on microarrays, were identified. Many of these highly expressed genes encode proteins of unidentified function.

Previously, only a handful of genes have been available for analysis of promoters; these included primarily seed storage protein or other genes with highly abundant transcripts. The set of genes of the present invention includes a much wider range of examples, including genes with different expression timing and levels.

The promoter regions of the present invention are identified from such genes, isolated, and characterized, as described below.

C. Identification, Isolation and Characterization of Seed-Specific Promoter Regions The next stage in the discovery of seed-specific promoter regions is to select a subset from an initial set of ESTs which are identified as highly expressed and seed-specific and which are genome sequences. Whether an EST sequence is a genome sequence is determined by comparing the EST sequence to the *Arabidopsis* genome by BLASTN searches. The flanking sequences of these genes is analyzed by programs such as GeneScan, GeneStart, and Genefinder to predict the associated promoter regions. Next, a subset of the gene promoter regions is identified, and characterized. Characterization includes determining the effectiveness of each promoter region to control expression of a reporter gene in transgenic seed tissue. Characterization also includes determining the effectiveness of fragments or modifications to a promoter region to control expression of a reporter gene in transgenic seed tissue. Additional seed-specific promoter regions are provided by identifying promoter regions naturally located upstream to a structural DNA sequence which hybridizes to a cDNA probe derived from the second subset of genomic ESTs which are identified as highly expressed and seed-specific, and which comprise naturally occurring effective promoter regions.

1. Identification of Seed-Specific Promoter Regions

From consideration of EST abundance and microarray signals, an initial set of about 30 genes were identified as highly expressed and seed specific, and for which genomic sequence data was available from GenBank. For every such gene, a sequence of about 20 kb, including the gene and flanking regions in both directions, were analyzed by gene identification programs. Such programs include, but are not limited to, GeneScan, GeneStart, and Genefinder, and are used to determine the positions of the ATG start codons. In cases where regions of the genomic sequence have been previously annotated, the results obtained from Genescan were always similar to the previous annotated results. As a result of the gene prediction analysis, certain genes were regarded as undesirable for one of several reasons. These reasons included, for example, that the predicted protein was larger than expected or that the ATG was predicted by the software with low probability. Ultimately, the predicted results of 20 out of the initially selected 30 genes were considered acceptable, and their upstream sequences used to identify seed-specific promoter regions; these genes are listed in Table 2 (as shown in FIG. 18).

By definition, the regions approximately 1 kb upstream of the ATC start codons of each of these 20 genes were considered to be promoter regions; these regions were then selected for subsequent PCR amplification. In some cases, PCR failed to yield a single band, or cloning of the PCR product was unsuccessful. Therefore, a set of 12 promoter region sequences were amplified and further considered; these promoter regions were obtained from genes 1, 3, 4, 6, 7, 9, 13, 14, 15, 16, 17 and 19, and are referred to as P1, P3, P4, P6, P7, P9, P13, P14, P15, P16, P17 and P19, respectively.

Characterization of the selected promoter regions includes determining the effectiveness of each promoter region to control expression of a reporter gene in transgenic seed tissue, as described below.

2. Identification of Promoter Modifications and Fragments

Once seed-specific promoter regions have been identified and characterized, it is then possible to identify fragments within the promoter region. For example, bioinformatics analysis of several hundred such promoters utilizing approaches similar to those described by Hughes et al., J. J. Mol. Biol., 296:1205-1214 (2000); Tavazoie et al., Nat. Genet., 22:81-285 (1999); or Zhang et al., Comput. Chem., 23:233-250 (1999), offer new insights on cis activation sequences responsible for control of seed expression. Moreover, these promoters can be used to clone their corresponding trans acting elements using yeast one-hybrid screenings or similar approaches.

The present invention further provides variant or modified sequences of the promoter sequences and 5'-upstream regulatory sequences described herein, where said variant sequences maintain the characteristic property of controlling or regulating seed-specific gene expression. For example, sequence variants include sequences with one or more nucleotide additions, deletions, or substitution. Such changes include those in sequences that do not directly interact with a polymerase or transcriptional regulatory factors (for example, deletions to reduce the overall size of the construct without altering regulatory function) as well as changes within functional portions of the regulatory sequences. For example, in some embodiments of the present invention, sequence changes are made within a promoter sequence or enhancer or repressor sequence to alter the binding of the associated polymerase or transcription factor. In some embodiments, such changes are applied to increase or decrease the transcription of the associated gene. In some embodiments, changes are made to alter the ability of a transcription factor to bind to an enhancer sequence. Such changes allow, for example, the ability to alter the responsiveness of gene transcription to intracellular or extracellular signals (for example, hormonal signals). Likewise, changes can be made to make gene transcription responsive to a particular signal. For example, a promoter or enhancer sequence can be altered such that the new sequence is generated that is similar or identical to a consensus sequence or a sequence associated with a different gene, cell, or organism. In some embodiments, such changes allow the promoter and 5'-upstream regulatory region to be used effectively in across species. One skilled in the art can readily test an altered sequence to determine if it has the desired function. For example, the altered sequence can be connected to a reporter gene to determine the effect of the altered sequence compared to the unaltered sequence, using methods well known in the art.

Fragments of the promoters of the present invention may be generated from the isolated genomic regions by exonuclease III-mediated deletion. This is accomplished by digesting appropriately prepared DNA with exonuclease III (exoIII) and removing aliquots at increasing intervals of time during the digestion. The resulting successively smaller fragments of DNA may be sequenced to determine the exact endpoint of the deletions. There are several commercially available systems which use exonuclease III (exoIII) to create such a deletion series, for example Promega Biotech, "Erase-A-Base" system. Alternatively, PCR primers can be defined to allow direct amplification of the promoter regions of the present invention, or parts thereof such as promoters and 5' transcribed but untranslated regions. Any and all deletion fragments which comprise a contiguous portion of the nucleotide sequences set forth in any of SEQ ID NOS: 1-12 and which retain the capacity to direct seed-specific expression are contemplated by the present invention.

Motifs of the promoter regions of the present invention are discovered by further analysis of the promoter region sequences. In one method, the sequences are compared by sequence alignments to determine areas of high similarity. In another method, the sequences are evaluated for the presence of regions with particular functions or known structures, such as binding sites or stem-loop structures. Such motifs, which retain or affect in any way the capacity to direct seed-specific expression are also contemplated by the present invention. In some embodiments, promoters which comprise these motifs are also seed-specific promoters. In other embodiments, nucleic acid sequences which comprise these motifs are seed-specific promoters.

For example, in promoters P6, P14, and P16, there is an inverted-repeat sequence (indicated by highlight in FIGS. 15-17). The BLAST result of these sequences blasted against their reverse complementary sequences are also shown in the FIGS. 15-17. These particular inverted-repeat sequences do not appear to have been studied before. These motifs also differ from those previously reported, in that they do not have an interval between two repeats, as has been reported for transposon, virus, and chloroplast DNA, and some DNA genomic fragments.

3. Characterization of Promoter Regions

Confirmation that a seed-specific promoter region is effective and directs seed-specific expression, and the effect of modifications or fragments of such a promoter on seed-specific expression, is accomplished by construction of transcriptional and/or translational fusions of specific promoter sequences with the coding sequences of a heterologous gene, transfer of the chimeric gene into an appropriate host, and detection of the expression of the heterologous gene in seed tissue or developing seed tissue, but not in non-seed tissue. The assay used to detect expression depends upon the nature of the heterologous sequence. For example, reporter genes, exemplified by chloramphenicol acetyl transferase and β-glucuronidase (GUS), are commonly used to assess transcriptional and translational competence of chimeric constructions. Standard assays are available to sensitively detect the reporter enzyme in a transgenic organism.

The β-glucuronidase (GUS) gene is useful as a reporter of promoter activity in transgenic plants because of the high stability of the enzyme in plant cells, the lack of intrinsic β-glucuronidase activity in higher plants and availability of a quantitative fluorimetric assay and a histochemical localization technique. Standard procedures for biochemical and histochemical detection of GUS activity in plant tissues have been established Jefferson et al. (1987) EMBO J. 6: 3901-3907). Biochemical assays are performed by mixing plant tissue lysates with 4-methylumbelliferyl-β-D-glucuronide, a fluorimetric substrate for GUS, incubating one hour at 37° C., and then measuring the fluorescence of the resulting 4-methyl-umbelliferone. Histochemical localization for GUS activity is determined by incubating plant tissue samples in 5-bromo-4-chloro-3-indolyl-glucuronide (X-Gluc) for about 18 hours at 37° C. and observing the staining pattern of X-Gluc. The construction of such chimeric genes allows definition of specific regulatory sequences and demonstrates that these sequences can direct expression of heterologous genes in a seed-specific manner.

Constructs are prepared generally as described below; they are then used to transform plants, also as generally described below. One such GUS construct is described in Example 3; this construct is used to transform *Arabidopsis* plants (as described below) for the following characterization studies.

The strength of the promoter regions of the present invention are determined by first confirming that the promoter regions result in GUS expression in developing seed. Next, seed tissue is collected from developing seed at least two different time points during development (such as 6 and 16 days after pollination, or DAP), and GUS activity quantitated. GUS activity under control of a seed-specific promoter region is compared to expression of GUS in wild type seeds, as well as expression of GUS under control of Napin, Phaseolin, and 35S promoters, such as is described in Example 3. Each construct is assayed in several different transformants, and in preferably at least 10-20 different transformants. The strength of the promoter regions are determined by the expression of GUS under control of the promoter regions of the present invention relative to its expression under the control promoters.

The tissue specificity of the promoter regions of the present invention is determined by examining GUS expression in different tissues. The tissues to be examined include but are not limited to young seedlings, roots, floral tissue, vascular tissue, maturing leaf tissue, and siliques; the presence of GUS is measured and its localization determined by histochemical staining. Seed-specificity of a particular promoter region is evaluated by observed GUS expression ratios between silique and the other tissues. A ratio of greater than one indicates that the promoter is seed-specific; preferably, the ratio is greater than about two; more preferably, the ratio is greater than about four; and even more preferably the ratio is greater than about ten.

The expression of GUS is also determined in different embryo stages. For this purpose, developing embryo tissue is collected at 3, 6, 9, 12, 15, and 18 DAP, and the location and amount of GUS expression determined by histochemical staining. Thus, both the timing and the level of expression of the promoter regions of the present invention are determined by the period during which GUS expression is observed, and by the amount of GUS activity observed.

Additional factors which may affect the levels of expression of a heterologous gene under control of a seed-specific promoter include copy number, or the number of copies of the heterologous gene transfected into a transgenic plant, and position effect, or the effect of the chromosomal location of the inserted heterologous gene in a transgenic plant. In the experiments described in the Examples, it appears that copy number was not correlated to the level of gene expression, but that the insertion position might affect the level of gene expression.

Of the promoters of the present invention, six promoters resulted in GUS levels in transgenic plants which were easily detected; these six promoters are P1, P3, P4, P6, P16, and P17. However, GUS activity for the remaining six promoters, P7, P9, P13, P14, P15, and P19, were very low or undetectable in the initial set of transgenic plants. It is not possible to rule out insertional position effects as resulting in these low levels of GUS activities. It is also possible that these promoters may require additional sequences beyond the predicted TATA box and start codon. Thus, identification of useful and effective seed-specific promoters cannot be predicted reliably from sequence information alone, and preferably requires experimental confirmation.

4. Identification of Additional Promoter Regions

It is contemplated that the sequences described herein can be utilized to identify and isolate additional seed-specific genes and their associated promoters, preferably from other species of plants.

Accordingly, in some embodiments, the present invention provides methods by which genomic sequences' under control of the promoter regions of the present invention (as for example, genes 1-20 as described in Table 2, as shown in FIG. 18) are used to identify additional homologous genomic sequences, preferably from other plants; the promoter regions of these homologous genomic sequences are then identified and isolated as described previously. Thus, in some aspects of the present invention, an at least partial genomic sequence of a plant is analyzed for sequences which are homologous to the *Arabidopsis* sequences which are identified as being specifically expressed in seeds (for example, those *Arabidopsis* sequences listed in Table 2, as shown in FIG. 18). For example, BLAST searches (Altshul et al., Nucleic Acids Res. 25:3389-3402 (1997)) may be utilized to search for nucleic acids having homology (for example, greater than 60%, 70%, 80%, or 90%) to the *Arabidopsis* sequences identified as expressed seed-specifically. Once homologous seed-specific genetic sequences are identified and isolated, they can be used to isolate promoter sequences as described above.

In other aspects of the present invention, it is contemplated that the promoter regions of the present invention (for example, promoter regions P1, P3, P4, P6, P7, P9, P13, P14, P15, P16, P17, and P19, as shown in FIGS. 1-12), may be utilized to search computer databases for homologous promoter sequences from other species, as described above.

In yet other aspects of the present invention, additional seed-specific promoter regions are provided by identifying promoter regions naturally located upstream to a structural DNA sequence which hybridizes to a cDNA probe derived from the second subset of genomic ESTs which are identified as highly expressed and seed-specific, and which comprise naturally occurring effective promoter regions. These promoter regions are then isolated and characterized as described above.

II. Utilization of Promoters to Control Expression of Nucleic Acid Sequences of Interest The present invention further comprises methods of controlling expression of nucleic acid sequences of interest using seed specific promoter regions of the present invention.

A. Nucleic Acid Sequences of Interest

In some embodiments, the compositions and methods of the present invention are used to control or direct nucleic acid sequence expression in plant seed tissue. Although such sequences are referred to as "genes" under this section, it is understood that these sequences refer to the coding section of the gene which is expressed as an RNA product, but that these sequences do not necessarily include the promoter region, although other regulatory regions may be included. In certain embodiments the endogenous promoter region is not included; in others, it may be. The methods are not limited to the control of any particular gene. Indeed, a variety of genes are contemplated for control, including, but not limited to those, described below.

In some embodiments, the gene of interest is an endogenous plant gene. The methods of the present invention are not limited to any particular plant. Indeed, a variety of plants are contemplated, including, but not limited to angiosperms, gymnosperms, monocotyledons, and dicotyledons. Specific plants contemplated include, but are not limited to, wheat, barley, maize, rye, rice, soybean, hemp, triticale, apricots, oranges, quince, melon, plum, cherry, peach, nectarine, strawberry, grape, raspberry, blackberry, pineapple, papaya, mango, banana, grapefruits, apples, pears, avocados, walnuts, almonds, filberts, pecans, carrots, lettuce, zucchini, tomatoes, beans, peas, cabbage, chicory, onion, garlic, pepper, squash, pumpkin, celery, turnips, radish, spinach, cauliflower, potatoes, sweet potatoes, broccoli, eggplant, cucumber, asparagus, poplar, pine, sequoia, cedar, oak, tobacco, clover, lotus, jojoba, rapeseed, sunflower, sorghum, sugarcane, sugar beet, safflower, *arabidopsis*, alfalfa, and cotton.

In some embodiments, the compositions and methods of the present invention are used to control or direct the expression of a gene involved in a metabolic pathway of a plant cell (for example, genes responsible for the synthesis or metabolism of peptides, proteins, fatty acids, lipids, waxes, oils, starches, sugars, carbohydrates, flavors, odors, fragrances, toxins, carotenoid pigments, hormones, cell wall polymers, gene regulatory molecules, flavonoids, storage proteins, phenolic acids, coumarins, alkaloids, quinones, lignins, glucosinolates, tannins, aliphatic amines, celluloses, polysaccharides, glycoproteins and glycolipids), in resistance or susceptibility of a plant to diseases (for example, to viral infection), in a visible phenotype (for example, flower color intensity, color hue and color pattern); or cell differentiation. For example, specific genes contemplated include, but are not limited to, those described in U.S. Pat. Nos. 5,107,065; 5,283,184; and 5,034,323; each of which is herein incorporated by reference.

In other embodiments, the compositions and methods of the present invention are used to alter the expression of a plant gene whose function is unknown in order to elucidate its function. Sense and antisense fragments of the gene are introduced to the plant. The plant is then examined for phenotypic changes (for example, metabolic or visible).

B. Methods of Transforming Plants

1. Vectors

Nucleic acid sequences of interest intended for expression in plants are first assembled in expression cassettes comprising a promoter (for example, the promoter regions of the present invention). Methods which are well known to those skilled in the art may be used to construct expression vectors containing nucleic acid sequences of interest and appropriate transcriptional and translational control elements. These methods include in vitro recombinant DNA techniques, synthetic techniques, and in vivo genetic recombination. Such techniques are widely described in the art (See for example, Sambrook. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y., both of which are herein incorporated by reference).

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters of the present invention. Transcriptional terminators are responsible for the termination of transcription beyond the transcript and its correct polyadenylation. Appropriate transcriptional terminators and those which are known to function in plants include, but are not limited to, the CaMV 35S terminator, the tml terminator, the pea rbcS E9 terminator, and the nopaline and octopine synthase terminator (See for example, Odell et al., Nature 313:810 (1985); Rosenberg et al., Gene, 56:125 (1987); Guerineau et al., Mol. Gen. Genet., 262:141 (1991); Proudfoot, Cell, 64:671 (1991); Sanfacon et al., Genes Dev., 5:141; Mogen et al., Plant Cell, 2:1261 (1990); Munroe et al., Gene, 91:151 (1990); Ballas et al., Nucleic Acids Res. 17:7891 (1989); Joshi et al., Nucleic Acid Res., 15:9627 (1987)).

In addition, in some embodiments, constructs for expression of a nucleic acid sequence of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells (Callis et al., Genes Develop. 1: 1183 (1987)). Intron sequences have been routinely incorporated into plant transformation vectors, typically within the non-translated leader.

In some embodiments of the present invention, the construct for expression of the nucleic acid sequence of interest also includes a regulator such as a nuclear localization signal (Kalderon et al., Cell 39:499 (1984); Lassner et al., Plant Molecular Biology 17:229 (1991)), a plant translational consensus sequence (Joshi, Nucleic Acids Research 15:6643 (1987)), an intron (Luehrsen and Walbot, Mol. Gen. Genet. 225:81 (1991)), and the like, operably linked to the nucleic acid sequence of interest.

In preparing the construct comprising the nucleic acid sequence of interest, various DNA fragments can be manipulated, so as to provide for the DNA sequences in the desired orientation (for example, sense or antisense) orientation and, as appropriate, in the desired reading frame. For example, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (for example, transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra, Gene 19: 259 (1982); Bevan et al., Nature 304:184 (1983)), the bar gene which confers resistance to the herbicide phosphinothricin (White et al., Nucl Acids Res. 18:1062 (1990); Spencer et al., Theor. Appl. Genet. 79: 625 (1990)), the hph gene which confers resistance to the antibiotic hygromycin (Blochlinger and Diggelmann, Mol. Cell. Biol. 4:2929 (1984)), and the dhfr gene, which confers resistance to methotrexate (Bourouis et al., EMBO J., 2:1099 (1983)).

In some embodiments of the present invention, transformation is carried out using *Agrobacterium tumefaciens* mediated methods. Many vectors are available for transformation using *Agrobacterium tumefaciens*. These typically carry at least one T-DNA border sequence and include vectors such as pBIN19 (Bevan, Nucl. Acids Res., 12:8711 (1984)). An additional vector useful for *Agrobacterium*-mediated transformation is the binary vector pCIB10 (Rothstein et al., Gene 53:153 (1987)) which contains a gene encoding kanamycin resistance for selection in plants, T-DNA right and left border sequences and incorporates sequences from the wide host-range plasmid pRK252 allowing it to replicate in both *E. coli* and *Agrobacterium*. Various derivatives of pCIB10 have been constructed which incorporate the gene for hygromycin B phosphotransferase (See for example, Gritz et al., Gene, 25: 179 (1983)). These derivatives enable selection of transgenic plant cells on hygromycin only (pCIB743), or hygromycin and kanamycin (pCIB715, pCIB717).

In some embodiments of the present invention, the nucleic acid sequence of interest is introduced directly into a plant. One vector useful for direct gene transfer techniques in combination with selection by the herbicide Basta (or phosphinothricin) is a modified version of the plasmid pCIB246, with the CaMV 35S promoter replaced by a promoter region of the present invention (for example, SEQ ID NOs: X) in operational fusion to the *E. coli* GUS gene and the CaMV 35S transcriptional terminator and is described in WO 93/07278, which is herein incorporated by reference. In some embodiments of the present invention, this vector is modified to include a promoter of the present invention (for example, SEQ ID NOs: X) operatively linked to two nucleic acid sequences of interest. The gene providing resistance to phosphinothricin is the bar gene from *Streptomyces hygroscopicus* (Thompson et al., EMBO J., 6:2519 (1987)).

2. Transformation Techniques

Once the nucleic acid sequences have been operatively linked to a promoter of the present invention and inserted into a suitable vector for the particular transformation technique utilized (for example, one of the vectors described above), the recombinant DNA described above can be introduced into a plant cell in a number of art-recognized ways. Those skilled in the art will appreciate that the choice of method depends upon the type of plant targeted for transformation. In some embodiments, the vector is maintained episomally. In other embodiments, the vector is integrated into the genome.

In some embodiments, vectors useful in the practice of the present invention are microinjected directly into plant cells by use of micropipettes to mechanically transfer the recombinant DNA (Crossway, Mol. Gen. Genet, 202:179 (1985)). In still other embodiments, the vector is transferred into the plant cell by using polyethylene glycol (Krens et al., Nature, 296:72 (1982); Crossway et al., BioTechniques, 4:320 (1986)); fusion of protoplasts with other entities, either mini-cells, cells, lysosomes or other fusible lipid-surfaced bodies (Fraley et al., Proc. Natl. Acad. Sci., USA, 79:1859 (1982)); protoplast transformation (EP 0 292 435; herein incorporated by reference); direct gene transfer (Paszkowski et al., EMBO J., 3:2717 (1984); Hayashimoto et al., Plant Physiol. 93:857 (1990)).

In other embodiments, the vector may also be introduced into the plant cells by electroporation. (Fromm, et al., Pro. Natl Acad. Sci. USA 82:5824, 1985; Riggs et al., Proc. Natl. Acad. Sci. USA 83:5602 (1986)). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In still further embodiments, the vector is introduced through ballistic particle acceleration using devices (for example, available from Agracetus, Inc., Madison, Wis. and Dupont, Inc., Wilmington, Del.). (See for example, U.S. Pat. No. 4,945,050; herein incorporated by reference; and McCabe et al., Biotechnology 6:923 (1988)). See also, Weissinger et al., Annual Rev. Genet. 22:421 (1988); Sanford et al., Particulate Science and Technology, 5:27 (1987) (onion); Svab et al., Proc. Natl. Acad. Sci. USA, 87:8526 (1990) (tobacco chloroplast); Christou et al., Plant Physiol., 87:671 (1988) (soybean); McCabe et al., Bio/Technology 6:923 (1988) (soybean); Klein et al., Proc. Natl. Acad. Sci. USA, 85:4305 (1988) (maize); Klein et al., Bio/Technology, 6:559 (1988) (maize); Klein et al., Plant Physiol., 91:4404 (1988) (maize); Fromm et al., Bio/Technology, 8:833 (1990); and Gordon-Kamm et al., Plant Cell, 2:603 (1990) (maize); Koziel et al., Biotechnology, 11:194 (1993) (maize); Hill et al., Euphytica, 85:119 (1995) and Koziel et al., Annals of the New York Academy of Sciences 792:164 (1996); Shimamoto et al., Nature 338: 274 (1989) (rice); Christou et al., Biotechnology, 9:957 (1991) (rice); Datta et al., Bio/Technology 8:736 (1990) (rice); European Patent Application EP 0 332 581, herein incorporated by reference (orchard grass and other Pooideae); Vasil et al., Biotechnology, 11: 1553 (1993) (wheat); Weeks et al., Plant Physiol., 102: 1077 (1993) (wheat); Wan et al., Plant Physiol. 104: 37 (1994) (barley); Knudsen and Muller, Planta, 185:330 (1991) (barley); Umbeck et al., Bio/Technology 5: 263 (1987) (cotton); Casas et al., Proc. Natl. Acad. Sci. USA 90:11212 (1993) (sorghum); Somers et al., Bio/Technology 10:1589 (1992) (oat); Torbert et al., Plant Cell Reports, 14:635 (1995) (oat); Weeks et al., Plant Physiol., 102:1077 (1993) (wheat); and Chang et al., WO 94/13822 (wheat).

In addition to direct transformation, in some embodiments, the vectors comprising the nucleic acid sequences of interest and a promoter of the present invention are transferred using Agrobacterium-mediated transformation (Hinchee et al., Biotechnology, 6:915 (1988); Ishida et al., Nature Biotechnology 14:745 (1996)). Agrobacterium is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (for example, nucleic acid sequences operatively linked to a promoter of the present invention), can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome (Schell, Science, 237: 1176 (1987)). Species which are susceptible infection by *Agrobacterium* may be transformed in vitro.

3. Regeneration

After determination of the presence and expression of the desired gene products, whole plants are regenerated. Plant regeneration from cultured protoplasts is described in Evans et al., Handbook of Plant Cell Cultures, Vol. 1: (MacMillan Publishing Co. New York, 1983); and Vasil L. R. (ed.), Cell Culture and Somatic Cell Genetics of Plants, Acad. Press, Orlando, Vol. I. 1984, and Vol. III, 1986. It is known that many plants can be regenerated from cultured cells or tissues, including both monocots and dicots, and including for example, crop plants, ornamentals and other horticultural plants, shrubs, and trees. Means for regeneration vary from species to species of plants, but generally a suspension of transformed protoplasts is first provided. Callus tissue is formed and shoots may be induced from callus and subsequently rooted.

Alternatively, embryo formation can be induced from the protoplast suspension. These embryos germinate and form mature plants. The culture media will generally contain various amino acids and hormones, such as auxin and cytokinins. Shoots and roots normally develop simultaneously. Efficient regeneration will depend on the medium, on the genotype, and on the history of the culture. The reproducibility of regeneration depends on the control of these variables.

III. Methods of Production of Gene Products of Interest

The present invention further comprises methods of producing products of nucleic acid sequences of interest by using promoter regions of the present invention.

A. Production in Plants

In some embodiments, the present invention provides methods of producing one or more gene products of interest using a promoter region of the present invention. In some embodiments, a promoter region of the present invention (for example, promoters regions P1, P3, P4, P6, P7, P9, P13, P14, P15, P16, P17, and P18, SEQ ID NOS: 1-12 as shown in FIGS. 1-12)) is used to express two gene products of interest (for example, two subunits of a multi-subunit protein or two members of a metabolic pathway) from the same promoter construct. In other embodiments, a sequence that hybridizes to a promoter regions of the present invention is utilized. In yet other embodiments, a sequence containing a fragment or modification of a promoter region of the present invention is utilized. In still other embodiments, an isolated promoter region naturally occurring upstream from a plant gene sequence which is homologous to at least one of the *Arabidopsis* sequences listed in Table 2 (shown in FIG. 18) is utilized. One skilled in the art will recognize, in view of the present disclosure, that the expression vectors comprising a promoter of the present invention and one or more nucleic acid sequences of interest may contain additional regulatory and enhancer elements specific to the host cell utilized for expression (for example, those described above or below).

In some embodiments, one or more gene products of interest are expressed in regenerated plants (for example, in seed tissue to elicit a specific metabolic response). In other embodiments, polypeptides of interest are expressed in plants for use in food stuffs (for example, to increase the nutritional value or to express a pharmaceutical compound). In still further embodiments, one or more polypeptides of interest are expressed in cell culture (for example, plant, bacterial, or eukaryotic cells) for the purpose of purifying the polypeptides of interest from the cell culture.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements may be utilized. For example, for expression mediated by plant viruses, viral promoters or leader sequences may be included in the vector.

In some preferred embodiments, the 5' leader sequence is included in the expression cassette construct. Such leader sequences can act to enhance translation. Translation leaders are known in the art and include: picornavirus leaders, for example, EMCV leader (Encephalomyocarditis 5' non-coding region; Elroy-Stein et al., PNAS, 86:6126 (1989)); potyvirus leaders, for example, TEV leader (Tobacco Etch Virus; Niepel and Gallie, J. Virol., 73:9080 (1999)) MDMV leader (Maize Dwarf Mosaic Virus; Virology, 154:9 (1986)), and human immunoglobulin heavy-chain binding protein (BiP; Macejak and Samow, Nature 353:90 (1991)); untranslated leader from the coat protein mRNA of alfalfa mosaic virus (AMV RNA 4; Jobling and Gebrke, Nature, 325:622 (1987)); tobacco mosaic virus leader (TMV; Gallie et al., Molecular-Biology of RNA, pages 237-256 (1989)); and maize chlorotic mottle virus leader (MCMV; Lommel et al., Virology 91:382 (1991); Della-Cioppa et al., Plant Physiology 84:965 (1987)).

In some embodiments, one or more polypeptides of interest are expressed in plants using stable transformation, as described above. In other embodiments, plant vectors are created using a recombinant plant virus containing a recombinant plant viral nucleic acid, as described in PCT publication WO 96/40867 which is herein incorporated by reference. Subsequently, the recombinant plant viral nucleic acid which contains one or more nucleic acid sequences encoding polypeptides of interest are transcribed or expressed in the infected tissues of the plant host and the polypeptides are recovered from the plant, as described in WO 99/36516, which is herein incorporated by reference.

In this embodiment, recombinant plant viral nucleic acids which contain a promoter region of the present invention linked to at least one nucleic acid sequence of interest are utilized. The recombinant plant viral nucleic acids have substantial sequence homology to plant viral nucleotide sequences and may be derived from an RNA, DNA, cDNA or a chemically synthesized RNA or DNA. A partial listing of suitable viruses is described below.

The first step in producing recombinant plant viral nucleic acids according to this particular embodiment is to modify the nucleotide sequences of the plant viral nucleotide sequence by known techniques such that a promoter region of the present invention (for example, P1, P3, P4, P6, P7, P9, P13, P14, P15, P16, P17 and P19, SEQ ID NOS: 1-12, as shown in FIGS. 1-12) is inserted into the plant viral nucleic acid without destroying the biological function of the plant viral nucleic acid. The native coat protein coding sequence may be deleted in some embodiments, placed under the control of a non-native subgenomic promoter in other embodiments, or retained in a further embodiment. If it is deleted or otherwise inactivated, a non-native coat protein gene is inserted under control of one of the non-native subgenomic promoters, or optionally under control of the native coat protein gene subgenomic promoter. The non-native coat protein is capable of encapsidating the recombinant plant viral nucleic acid to produce a recombinant plant virus. Thus, the recombinant plant viral nucleic acid contains a coat protein coding sequence, which may be native or a normative coat protein coding sequence, under control of one of the native or non-native subgenomic promoters. The coat protein is involved in the systemic infection of the plant host.

Some of the viruses suitable for use in the present invention include, but are not limited to viruses from the tobamovirus group such as Tobacco Mosaic virus (TMV), Ribgrass Mosaic Virus (RGM), Cowpea Mosaic virus (CMV), Alfalfa Mosaic virus (AMV), Cucumber Green Mottle Mosaic virus watermelon strain (CGMMV-W) and Oat Mosaic virus (OMV) and viruses from the brome mosaic virus group such as Brome Mosaic virus (BMV), broad bean mottle virus and cowpea chlorotic mottle virus. Additional suitable viruses include Rice Necrosis virus (RNV), and geminiviruses such as tomato golden mosaic virus (TGMV), Cassava latent virus (CLV) and maize streak virus (MSV).

Other embodiments of plant vectors used for the expression of sequences encoding polypeptides include, for example, a promoter region of the present invention used in combination with the omega leader sequence from TMV (Takamatsu, EMBO J. 6:307 (1987)). These constructs can be introduced into plant cells by any suitable methods, including, but not limited to those described above.

B. Confirmation of Product Presence

Host cells which contain a nucleic acid sequence of interest may be identified by a variety of procedures known to those of skill in the art. These procedures include, but are not limited to, enzyme assay, DNA-DNA or DNA-RNA hybridizations and protein bioassay or immunoassay techniques which include membrane, solution, or chip based technologies for the detection and/or quantitation of nucleic acid or protein.

The presence of nucleic acid sequences of interest can be detected by DNA-DNA or DNA-RNA hybridization or amplification using probes or portions or fragments of polynucleotides encoding the polypeptide. Nucleic acid amplification based assays involve the use of oligonucleotides or oligomers based on the sequences of interest to detect transformants containing DNA or RNA encoding the polypeptide.

A variety of protocols for detecting and measuring the expression of a polypeptide using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on the polypeptide is preferred, but a competitive binding assay may be employed. These and other assays are described, among other places, in Hampton et al., 1990; Serological Methods, a Laboratory Manual, APS Press, St Paul, Minn.; and Maddox et al., J. Exp. Med., 158:1211 (1983)).

A wide variety of labels and conjugation techniques are known by those skilled in the art and may be used in various nucleic acid and amino acid assays. Means for producing labeled hybridization or PCR probes for detecting sequences related to polynucleotides encoding a polypeptide of interest include oligonucleotide labeling, nick translation, end-labeling or PCR amplification using a labeled nucleotide. Alternatively, the sequences encoding the polypeptide, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits from Pharmacia & Upjohn (Kalamazoo, Mich.), Promega Corporation (Madison, Wis.) and U.S. Biochemical Corp. (Cleveland, Ohio). Suitable reporter molecules or labels, which may be used, include radionucleotides, enzymes, fluorescent, chemiluminescent, or chromogenic agents as well as substrates, cofactors, inhibitors, magnetic particles, and the like.

C. Recovery of Expressed Products

In some embodiments of the present invention, it is desirable to recover expressed proteins from seed tissue. Plants transformed with nucleotide sequences encoding one or more polypeptides of interest may be cultivated under conditions suitable for high expression and subsequent recovery of the protein from seeds. The protein produced by a recombinant cell may be secreted or contained intracellularly depending on the sequence and/or the vector used. As will be understood by those of skill in the art, expression vectors containing polynucleotides which encode the polypeptide(s) of interest may be designed to contain signal sequences which direct secretion of the polypeptide into a particular cell compartment, such as a vacuole or a plastid.

In other embodiments of the present invention, other recombinant constructions may be used to join sequences encoding a polypeptide to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (available from Invitrogen, San Diego, Calif.) between the purification domain and the polypeptide of interest may be used to facilitate purification. One such expression vector provides for expression of a fusion protein containing the polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath et al., Prot. Exp. Purif., 3:263 (1992) while the enterokinase cleavage site provides a means for purifying the polypeptide from the fusion protein. A discussion of vectors which contain fusion proteins is provided in Kroll et al., DNA Cell Biol., 12:441 (1993)).

D. Increasing or Decreasing Gene Expression

It is contemplated that promoter regions of the present invention may be utilized to either increase or decrease the level of expression of nucleic acid sequences of interest in transfected cells as compared to the levels in wild-type cells. Accordingly, in some embodiments, expression in plants by the methods described above leads to the overexpression of nucleic acid sequences of interest in transgenic plants, plant tissues, or plant cells.

In other embodiments of the present invention, the promoter regions of the present invention are utilized to decrease the level of expression of nucleic acid sequences of interest in transgenic plants, plant tissues, or plant cells as compared to wild-type plants, plant tissues, or plant cells. One method of reducing expression utilizes expression of antisense transcripts. Antisense RNA has been used to inhibit plant target genes in a tissue-specific manner (for example, van der Krol et al., Biotechniques 6:958-976 (1988)). Antisense inhibition has been shown using the entire cDNA sequence as well as a partial cDNA sequence (for example, Sheehy et al., Proc. Natl. Acad. Sci. USA 85:8805-8809 (1988); Cannon et al., Plant Mol. Biol. 15:39-47 (1990)). There is also evidence that 3' non-coding sequence fragment and 5' coding sequence fragments, containing as few as 41 base-pairs of a 1.87 kb cDNA, can play important roles in antisense inhibition (Ch'ng et al., Proc. Natl. Acad. Sci. USA 86:10006-10010 (1989)).

Accordingly, in some embodiments, promoter regions of the present invention (for example, P1, P3, P4, P6, P7, P9, P13, P16, P17, and P19, SEQ ID NOS: 1-12, as shown in FIGS. 1-12, and modifications and fragments thereof) are operably linked to nucleic acid sequences of interest which are oriented in a vector and expressed so as to produce antisense transcripts. To accomplish this, a nucleic acid segment from the desired gene is cloned and operably linked to a promoter region of the present invention such that the antisense strand of RNA will be transcribed. The expression cassette is then transformed into plants and the antisense strand of RNA is produced. The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

Furthermore, for antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of the target gene or genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *Solanum nodiflorum* mottle virus and subterranean clover mottle virus. The design and use of target RNA-specific ribozymes is described in Haseloff, et al., Nature 334:585-591 (1988).

Another method of reducing expression of nucleic acid sequences of interest utilizes the phenomenon of cosuppression or gene silencing (See for example, U.S. Pat. No. 6,063,947, incorporated herein by reference). The phenomenon of cosuppression has also been used to inhibit plant target genes in a tissue-specific manner. Cosuppression of an endogenous gene using a full-length cDNA sequence as well as a partial cDNA sequence (730 bp of a 1770 bp cDNA) are known (for example, Napoli et al., Plant Cell 2:279-289 (1990); van der Krol et al., Plant Cell 2:291-299 (1990); Smith et al., Mol. Gen. Genetics 224:477-481 (1990)). Accordingly, in some embodiments the promoter regions of the present invention are operably linked to nucleic acid sequences of interest which are expressed in another species of plant to effect cosuppression of a homologous gene.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For cosuppression, the introduced sequence in the expression cassette, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); I or L (liters); ml (milliliters); µl (microliters); cm (centimeters); mm (millimeters); µm (micrometers); nm (nanometers); ° C. (degrees Centigrade); Sigma (Sigma Chemical Co., St. Louis, Mo.).

In the following Examples, *Arabidopsis thaliana* (L.) ecotype Columbia (Col-0) plants were used for all of the procedures, from generating cDNA libraries to isolating genomic DNA to plant transformation.

Example 1

Developing Seed EST Isolation and Analysis

A. Library Preparation and Screening

To construct the *Arabidopsis* developing seed cDNA library, immature seeds of *Arabidopsis thaliana* ecotyope Col-2 were collected 5-13 days after flowering (DAF). RNA was extracted according to Hall et al. (Hall et al., Proc. Natl. Acad. Sci. U.S.A., 75:3196-3200 (1978)) from 1 g of seed tissue and a directional cDNA library was commercially prepared from polyA+ mRNA in the lambda ZAP II vector (Stratagene, La Jolla, Calif.) using oligo-(dT) as primer for cDNA synthesis. The primary library was amplified once to yield an initial titre of $1.9 \times 10^{10}$ pfu/ml and was used for all subsequent experiments. Based on 48 randomly selected clones the average insert size was estimated to be 1.9 kb, as determined by gel electrophoresis of PCR amplified inserts. Following the excision of phagemids according to the manufacturers instructions, bacterial colonies were arrayed onto nylon membranes at a density of 36 clones $cm^{-2}$ by Genome Systems, Inc (St. Louis). Data were generated in two stages corresponding to a first set with 9,136 cDNA clones and a second set containing 18,432 clones.

B. Sequence Analysis

The first set of cDNAs (data set I) was sequenced at MSU from the 5' ends using the SK primer for pBluescript II, or from the 3' ends using the M13-21 primer. The second set of cDNAs (data set H) was sequenced by Incyte Pharmaceuticals, Inc. (Palo Alto, Calif.) from the 5' ends using the Bluescript T3 primer. Chromatograms from the data set I were processed in batches using Sequecher v.3.0 (Gene Codes Corp., Ann Arbor, Mich.). The 5' and 3' ambiguous sequences were trimmed. Vector sequences were removed as part of this process. Sequences that were less than 150 bp long or had >4% ambiguity were not processed. Chromatograms from data set II were processed in bulk using PHRED (Phil Green and Brent Ewing, University of Washington, Seattle, Wash.). Sequences that were less than 225 bp or >4% ambiguous were not further processed. At this time 95% of the sequences have been deposited at GenBank. The remaining 5% (exclusively derived from data set A) will be available in GenBank by March, 2001.

C. Database Searches

For data set I, sequences were exported to plain (ASCII) text files that were used for similarity searches against GenBank using BLASTX version 1.4.11 (Altschul et al., J. Mol. Biol., 215:403-410 (1990)). Sequences were first reformatted with the GCG (Wisconsin Package Version 9.1, Genetics Computer Group (GCG), Madison, Wisc.) program REFORMAT, and the searches were done in batches using shell or PERL scripts that used GCG NETBLAST for each sequence. For data set II, the FASTA file produced by PHRED/PHD2FASTA was processed by PERL scripts to do BLASTX searches with default parameters. PERL scripts were used to assess the level of ambiguity in the DNA sequences (FASTA files) and estimate quality of the sequences based on the .qual files produced by PHRED/PHD2FASTA. The BLASTX searches were done over a period of 12 month from Sep. 2, 1998 to Sep. 21, 1999 using the most recent releases of GenBank. A subset was periodically retested (see below). The output from BLASTX was processed with PERL scripts to extract the top scoring hit from each result file. The following information for the top scoring entry in each result file was retained: gene identifier, description, BLAST score, probability, percent identity, alignment length, and reading frame. These results were compiled in text files. Each result was manually interpreted and categorized according to predicted biochemical function. BLASTN searches were done against a subset of dbBEST containing only *Arabidopsis* sequences using a FASTA file with all raw sequences. Standalone BLASTN version 2.0.9 running under linux 5.2 was used for this analysis.

D. Contig Analysis

Contig analysis was performed with PHRAP (Phil Green, University of Washington, Seattle, Wash.). Chromatograms from both data sets were processed with PHRED/PHD2FASTA, CROSS_MATCH (to mask vector sequence), and PHRAP (minmatch 12, minscore 20). The PHRAP command-line argument "trim_start 30" was used to trim the first 30 bp from each sequence. The .ace output file from PHRAP was processed with a PERL script to obtain the list of ESTs in each contig. Contigs were manually screened and corrected in cases where obviously unrelated sequences were clustered together.

E. Database

All data were imported into a Microsoft Access 97 relational database. The database was built around unique clone identifiers which refer to clone locations in microtiter plates.

Example 2

Microarray Analysis of ESTs from Developing Seeds

A. Amplification of cDNAs

The plasmids of 2715 selected cDNA clones were collected from data set I. The inserts of the cDNAs were amplified by PCR in a 96-well format using primer pairs specific for the vector ends (for inserts in pBluescript SK-: T7, 5'-GTAATACGACTCACTATAGGGC (SEQ ID NO: 55), and 5' extended M13 reverse, 5'-ACAGGAAACAGCTATGACCATG (SEQ ID NO: 56); for inserts in pZipLox1: M13 forward, 5'-CCCAGTCACGACGTTGTAAAACG (SEQ ID NO: 57) and M13 reverse, 5'-AGCGGATAACAATTTCACACAGG (SEQ ID NO: 58). PCR reactions of 100 µL volume contained 0.4 µM of each primer, 0.2 µM of each desoxynucleotide, 10 mM Tris, 50 mM KCl, 3.0 mM $MgCl_2$, 3 U Taq DNA polymerase (Promega, Madison) and ~10 ng plasmid template. The reactions were run on a Perkin Elmer 9700 Thermoblock using an amplification program of 3 min denaturation at 94° C., 5 precycles of 30 s at 94° C., 30 s at 64° C., 2 min at 72° C., followed by 30 cycles of 30 s at 94° C., 30 s at 60° C., 2 min at 72° C. and terminated by 7 min extension at 72° C. The PCR products were precipitated by adding 200 μL ethanol (95%) and 10 μL sodium acetate (3M, pH 5.2) and centrifugation at 3200 g and 4° C. for 60 min. After washing with 80% ethanol, the DNA was resuspended in 20 μL 3×SSC. The yield and purity of the PCR products was analyzed by agarose gel electrophoresis. PCR samples showing by agarose gel analysis concentrations less than 0.2 μg/μL and/or double bands were repeated. If possible, alternative clones from the cDNA clone collection were used to repeat the PCR experiments. To reduce the cross-contamination risk in the 96-well format, failed PCRs were not removed from the sample set, and as a result the number of PCR samples for printing increased by approximately 20%.

B. Preparation of the cDNA Microarrays

Microscope slides (Gold Seal, No. 3010) were cleaned for 2 h in alkaline washing solution (25 g NaOH in 100 mL $H_2O$, 150 mL 95% ethanol), washed in distilled water (five times 5 min) and then coated for 1 h in 250 mL coating solution (25 mL poly-L-lysine, Sigma, St. Louis, 25 mL sterile filtered PBS, 200 mL $H_2O$). After coating, the slides were rinsed with water, dried by centrifugation (5 min at 600 rpm) and by subjecting them 10 min to 45° C. in a vacuum oven. After coating, the slides were cured in a slide box for at least two weeks.

PCR samples were arrayed in duplicates from 384-well plates with a center to center spacing of 260 μm onto poly-L-lysine coated slides using a printing device (GeneMachines, San Carlos) with 16 titanium pins (TeleChem, Sunnyvale). The resulting arrays contained 7680 elements with a size of 18×36 mm. After printing, the arrays were rehydrated over a water bath (50-60° C.) for 15 s, snap-dried for 5 s on a heating block (80° C.) and UV crosslinked with a UV 1800 Stratalinker (Stratagene, La Jolla) at 65 mJ of energy. After crosslinking, the remaining functional groups of the surface were blocked for 15 min in blocking solution (4.28 g succinic anhydride, Aldrich, Milwaukee, dissolved in 239.3 mL 1,2-methyl-pyrrolidinone, Aldrich, and 10.71 mL 1 M boric acid, pH 8.0 with NaOH). Directly after blocking, the bound DNA was denatured for 2 min in distilled water at 95° C., rinsed with 95% ethanol at room temperature and finally dried by centrifugation (5 min at 600 rpm).

To monitor the detection sensitivity limit, the inserts of nine human cDNA clones (IMAGE IDs 1593326, 1420858, 1484059, 978938, 1593605, 1020153, 1592600, 1576490, 204625) were amplified by PCR and arrayed at four different locations of the slide. The corresponding mRNA species in vitro transcribed from these human clones were added as internal standards to 1 μg of the plant mRNA samples before probe synthesis at levels from $1.0 \times 10^{-3}$ ng to $1.0 \times 10^{-5}$ ng.

To evaluate the hybridizations specificity, a 365 bp long PCR fragment from a FAD2 cDNA clone (L26296) and two synthetic fragments with 90% and 80% sequence identity to the FAD2 fragment were arrayed adjacent to each other. The related fragments were synthesized by PCR using 4 overlapping 110mer primers into which the required nucleotide exchanges were introduced (Dillon et al., Biotechniques, 9:298-300 (1990); De Rocher et al., Plant Physiol., 117:1445-1461 (1998)). The resulting three fragments were of equal length and constant GC content. Two additional specificity control sets with more variable similarity clusters in their sequence, were spotted as well. These sets contained ferredoxin cDNA sequences from *Arabidopsis*, *Anabaena* (M14737), *Thunbergia*, *Glycine max*, *Impatiens* (supplied from D. Schultz) and for ACP-desaturases from *Arabidopsis* (M40E01), *Geranium* (140344 & AF020203), *Coriandrum sativum* (M93115). Unspecific background hybridizations were monitored with PCR products from twelve human cDNAs (IMAGE IDs: h29512, h00641, t91128, 680973, 237257, 280523, 136643, 204716, 60027, 756944, 29328, IB187) arrayed in several copies at various locations of the array. To analyze the efficiency of the probe synthesis, the 5', central and 3' regions of two cDNA clones were spotted separately (FAD2, L26296 and a clone for the E1 subunit of the pyruvate dehydrogenase, M20C09). Constant signal intensities of these spots indicated that the probe synthesis by reverse transcription resulted in sufficient amounts of long products. The amount of rRNA contaminations in the hybridization probes were measured with DNA sequences coding for 25S rRNA and 18S rRNA from *Arabidopsis*. Unspecific probe binding mediated by the poly(A) tail of the cDNAs was detected with arrayed poly(A)$_{50}$ oligos. The washing efficiency of the spotting pins during the printing process was analyzed by arraying a sequence for RuBisCo SSU (118D13T7) and a negative control containing only 3×SSC after each other at several locations of the microarray. To localize the printing grid during the image analysis, the cDNA of a highly expressed translation elongation factor EF-1 alpha (M16D02) was arrayed at two edges of several subgrids.

C. Plant Material, RNA Extraction and Probe Synthesis

*Arabidopsis thaliana* ecotype Col-2 was grown in a growth chamber with 16 h light at 80-100 microeinsteins and temperatures of 22° C. day, 20° C. night. Developing seeds from each plant type were dissected from siliques at 8-11 days after flowering (DAF), and bulked. Leaf material was collected from the same plants of the same age. Total root tissue was collected from plants grown for 6 weeks in sealed tissue culture boxes containing 50 mL growth media (1× MS salts, 1×B vitamins and 0.5% agarose). *Brassica napus* (cv 212/86, line 18) was grown in a green house (Eccleston et al., Plant Cell, 10:613-622 (1998)). Seeds were collected from *B. napus* siliques 25-30 DAF and leaves were collected from the same plants of the same age.

Total RNA was extracted from 1.0 g plant tissue as described by Schultz et al., Plant Mol. Bio. Reptr., 12:310-316 (1994). The quality of each total RNA sample was confirmed in a reverse transcription (Superscript II, Boerhinger) test reaction in the presence of [$^{32}$P]dATP following manufacturer's instructions. The labeled single-stranded DNA products were separated by agarose gel electrophoresis. The gel was dried and then labeled products were visualized for 1 hour using autoradiography. Only RNA samples producing sufficient product in this test labeling were used for subsequent fluorescent probe synthesis. Poly(A)$^+$ RNA was isolated from 100 μg total RNA using OligotexÔ oligo(dT) beads (Qiagen, Valencia) following manufacturer's instructions. Preparation of fluorescent DNA probe was performed as follows: 1 μg poly(A)$^+$ RNA was mixed with 4 μg oligo (dT) primer, and 1 ng internal standard in a final volume of 26 μL. This mixture was incubated at 68° C. for 10 min, chilled on ice and then added to 24 μL of reaction mix with a final composition of 1× Superscript II buffer, 500 μM each of dATP, dTTP, dGTP, 200 μM dCTP, 60 μM Cy3 or Cy5-dCTP (Amersham Pharmacia, Piscataway), 10 mM DTT, 1 μL RNAsin (Boehringer, Mannheim), 3 μL Superscript II (600 U, Life Technologies, Rockville). The reaction was incubated at 42° C. for 60 min, then additional 360 U of Superscript II were added and incubation was continued at 42° C. for another 60 min. After addition of 10 μL of 1N NaOH, incubation was continued at 37° C. for 60 min. 1M Tris-HCl (25 μL, pH7.5) was then added and the reaction mix was diluted with 915 μL TE buffer, followed by extraction with first 1 vol of phenol:chloroform (1:1, v/v), and then 1 vol of chloroform: IAA (24:1, v/v). The labeled cDNA products were finally transferred to a Centricon 30 filtration column (Millipore, Bedford), washed twice with 2 mL TE buffer, and then concentrated to a final volume of 10 to 15 μL using a speed vac. Prior to this final concentration step, 1/100 of the labeled probe (approximately 2-4 μL) were removed to determine the quality of the labeling reaction by gel electrophoresis followed by analysis of the fluorescent signal from the separated products using a ScanArray® 3000 laser scanner (GSI Lumonics, Watertown).

D. Hybridization

Probe mixtures in a total volume of 24 μL were mixed with 6 μL blocking solution (10 μg/μL yeast tRNA, Sigma, 10 μg/μL oligo-dA, Pharmacia), 6.3 μL 20×SSC and 1.2 μL 10% SDS. The solution was denatured for 1 min at 100° C., cooled down to room temperature, and applied to the array. After covering the array with a 24×40 mm coverslip, the slide was placed in a humidified hybridization chamber (TeleChem). The hybridization was performed in a 64° C. water bath for ~16 h. After hybridization, the slides were washed in 1×SSC, 0.2% SDS for 5 min, then in 0.1×SSC, 0.2% SDS for 5 min, and finally in 0.1×SSC for 30 s. Following the last washing, the slides were immediately dried by centrifugation (5 min at 600 rpm).

E. Analysis and Quantitation

Hybridized microarrays were scanned sequentially for Cy3 and Cy5 labeled probes with a ScanArray® 3000 laser scanner at a resolution of 10 μm. In order to maximize the dynamic range of each scan without saturating the photomultiplier tube and to balance the signal intensities of the two channels approximately, laser power and PMT settings of the instrument were adjusted according to the Auto-Range and Auto-Balance features of the instrument. Signal quantitation was performed with the ScanAlyze 2.21 software written by Michael Eisen (available on the Internet). The two intensity values of duplicated DNA spots were averaged and used to calculate the intensity ratios between the two channels. Ratios below 1.0 were inverted and multiplied by −1 to aid their interpretation. Intensity values below three times their local background were deemed non-significant and excluded from further data analysis. Since subtraction of the local background from the intensity values often results in artificially high ratios, this operation was not performed for calculating the ratios. Normalization of the intensity values from the two channels was performed by stepwise exclusions of 5% of the highest and 5% of the lowest ratios and calculating for the remaining subsets the mean ratios. Usually, after excluding 15% of the highest and 15% of the lowest values, the calculated mean ratios reached a plateau, which showed only minor changes in the smaller subsets. The average value of the remaining 70% ratios was used to normalize the intensity ratios as close to 1.0 as possible. The accuracy of this filter method was evaluated by comparing it with the normalization factor calculated from the intensity ratios of the human mRNAs spiked into the labeling reaction. In general, the two methods resulted in relatively similar normalization factors. However, since external RNA controls disregard purity and integrity problems of the actual RNA samples, their use for normalization is more error prone than the filter method used for this study.

Example 3

Identification, Isolation and Characterization of Seed-Specific Promoter Regions A. Materials Genomic DNA which was used for PCR amplification was extracted from *Arabidopsis* leaves using the CTAB method (for example, as described by Stewart et al., Biotechniques: 14(5):748-50 (1993).

B. Data and Sequences Analysis

Individual EST sequences were compared using BLAST against *Arabidopsis* genomic sequences larger than 10 Kb using the TAIR server manually. After the positions of these EST sequences in the genome were determined, approximately 20 Kb flanking sequences of 30 genes were analyzed by Gene Identification Programs such as GenScan, GeneFinder and NetStart to determine the positions of ATG translation starts. The promoter regions were defined as those regions approximately 1 Kb upstream of ATG; these regions were then selected for PCR amplification.

C. Molecular Cloning and Vector Construction

Figure 14:
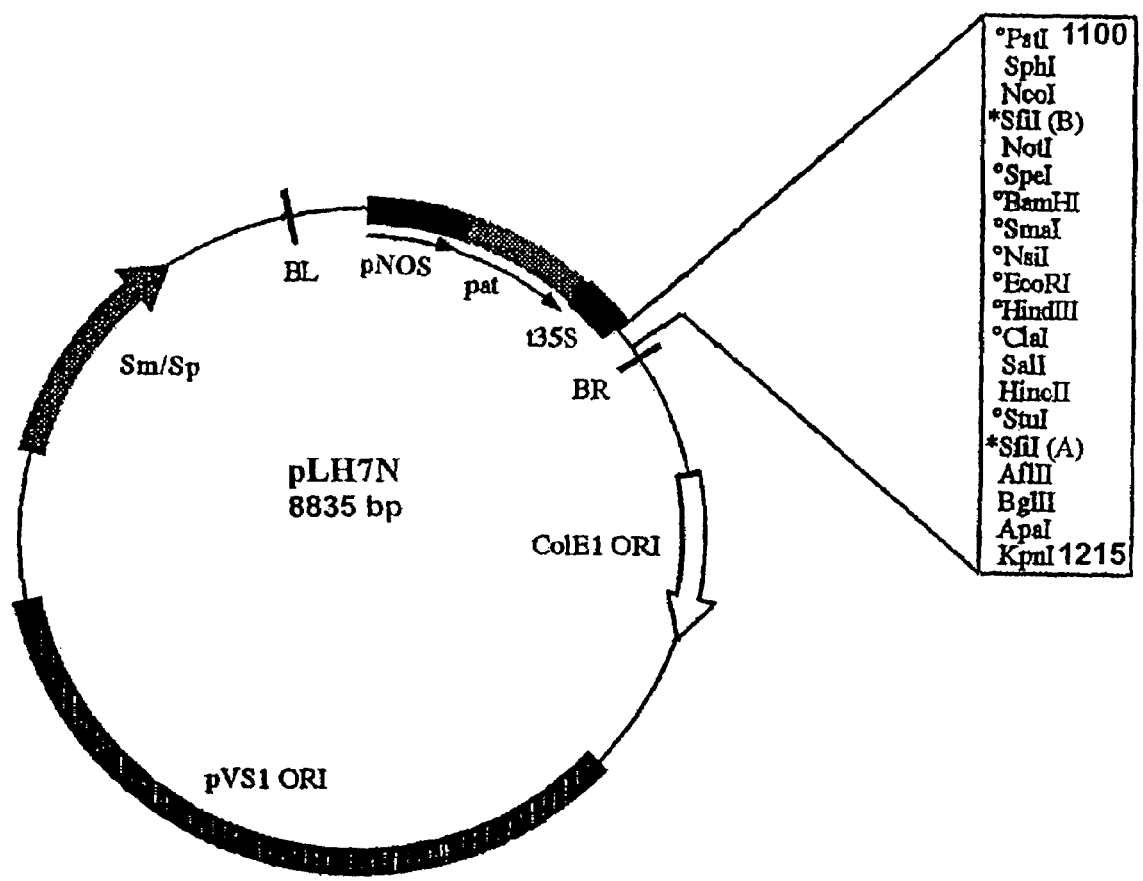
FIG. 14 shows the map of the vector pLH7N.

To construct a GUS expression vector with promoter regions of the present invention, restriction enzyme cutting site EcoR I, Mfe I and BamH I were added to the PCR forward and reverse primers to amplify the promoter regions (Table 3, as shown in FIG. 19). The PCR products were digested with EcoR I (or Mfe I) and BamH I and then inserted into the EcoR I-BamH I site of a promoterless β-glucuronidase (GUS) expression vector pBlue-BA-GUN. The Sfi-A to Sfi-B region were cut off from pBlue-BA-GUN (purchased from DNA-Cloning service, Hamburg, Germany) and then cloned into binary Ti-vector PLH7N (See FIG. 14).

Control vectors contained a GUS expression vector with either a napin or phaseolin promoter. For example, the promoter region of the napin (napA) gene in *Brassica napus* was amplified by using a forward primer CG aagctt TCT-TCATCGGTGATT (SEQ ID NO: 59) and reverse primer GGTCG gaattc GTGTATGTTTT (SEQ ID NO: 60). The PCR product was digested by Hind III and EcoR I, then inserted into SK+ vector and confirmed by sequencing. The napin promoter was cut by Hind III and BamH I and inserted into a GUS expression vector such that GUS is under control of the napin promoter region. In a similar fashion, a GUS expression vector under control of a phaseolin promoter region was constructed; the phaseolin promoter region is described in U.S. Pat. No. 5,504,200.

D. Plant Transformation and Selection

Plant transformation was performed by modification of the method of Clough et al., Plant J., 16:735-43 (1998). *Arabidopsis thaliana* plants were grown over long days in 50 cm2 square pots which were covered with a square of window mesh. When the first siliques were visible, the plants were then dipped by inverting the pots into the *Agrobacterium tumefaciens* (GV3101) suspension. The dipped plants were covered with plastic and brought back to the greenhouse. The plastic was removed after 2 to 3 days. Seeds were harvested after 3 weeks and germinated in soil. Transformants were selected by spraying phosphinothricin (PPT) at 100 mg/L 4 to 5 days after germination. Spraying was repeated two or three times to kill any possible pseudo-transformants.

E. Histochemical Localization of GUS Activities

The transgenic plants were assayed histochemically for GUS enzyme activity as follows. Freshly cut tissues, young seedlings, and embryos manually dissected from the seeds at different days after flowering (DAF) are immersed in a solution of 5-bromo-4-chloro-3-indolyl glucuronide (X-gluc), which contained buffer (50 mM $NaH_2PO_4$ buffer, pH 7.0), 10 mM $Na_2EDTA$, 0.1% Triton X-100, 0.5 mM $K3[Fe(CN)_6]$, 0.5 mM $K_4[Fe(CN)_6]$, 1.0 mg/mL 5-bromo-4-chloro-3-indolyl glucuronide (X-gluc) at 37° C. for 6 to 12 hr. After incubation, samples are rinsed in 50 mM $NaH_2PO_4$, pH 7.0, and cleared in two changes of 70% ethanol and one change of 95% ethanol to remove the chlorophyll. Unfixed whole plantlets, organs, or hand-cut sections are examined and photographed.

F. Quantitation of GUS Activities

For each construct, 8 DAF and 16 DAF embryos of several, and preferably 20, independent transgenic lines were collected for GUS assays. GUS activity was quantitated by using microplate reader system (SPECTRAmax GEMINI XS, from Molecular Devices). Seeds were homogenized using Kontes disposable pestles and microtubes in GUS extraction buffer (50 mM sodium phosphate pH 7.0, 20 mM DTT, 10 mM EDTA, 0.1% Sarkosyl, and 0.1% TritonX-100), and centrifuged 10 min in a 4° C. microcentrifuge. The supernatant from each sample was transferred to another tube and stored at −80° C. Plant extract (10 µl) was mixed with 40 µl assay buffer (GUS extraction buffer containing 1 mM methylumbelliferyl glucuronide (MUG)), and incubated at 37° C. for 0, 5, 10, 15 or 30 min. Then 150 µl 0.2 M $Na_2CO_3$ was added, and fluorescence of released methyl umbelliferone (MU) was measured using standard MU curves. GUS activity was expressed as pmol MU per milligram fresh weight per minute.

I. Identification of Effective Promoter Regions

Promoter regions are identified as effective seed-specific promoters if GUS activity in developing seed tissue is greater than GUS activity in other plant tissue. By greater, it is meant that the ratio of expression of GUS activity in developing seed tissue to that in other plant tissue is greater than one; preferably, this ratio is greater than about two; more preferably, this ratio is greater than about four; and even more preferably this ratio is greater than about ten (see, for example, Table 1). Preferably, effective seed-specific promoters are not expressed in other, non-seed tissues (in other words, the activity in other, non-seed tissue is no greater than background levels). Not all seed-specific promoters are active at the same time during seed development; some may be active throughout seed development, while others are active during a smaller period of seed development. Yet other seed-specific promoters are active to different levels during seed development.

Developing seeds were collected at 8 and 16 days after flowering for all constructs, and preliminary GUS analysis on these samples were used to rank the approximate strength of the promoters. For six promoters (P1, P3, P4, P6, P16 and P17), GUS activity was easily detected. However, these assays also indicated very low or no GUS activity for the remaining six of the twelve promoters initially identified (P7, P9, P13, P14, P15 and P19). This low activity may not be an indication that these promoters are ineffective, as it is possible that the low activity results from an incorrect prediction of the start codons of the genes, or that the selected promoter regions were not long enough to include enhancers or other regions needed for higher levels of expression.

Figure 20:
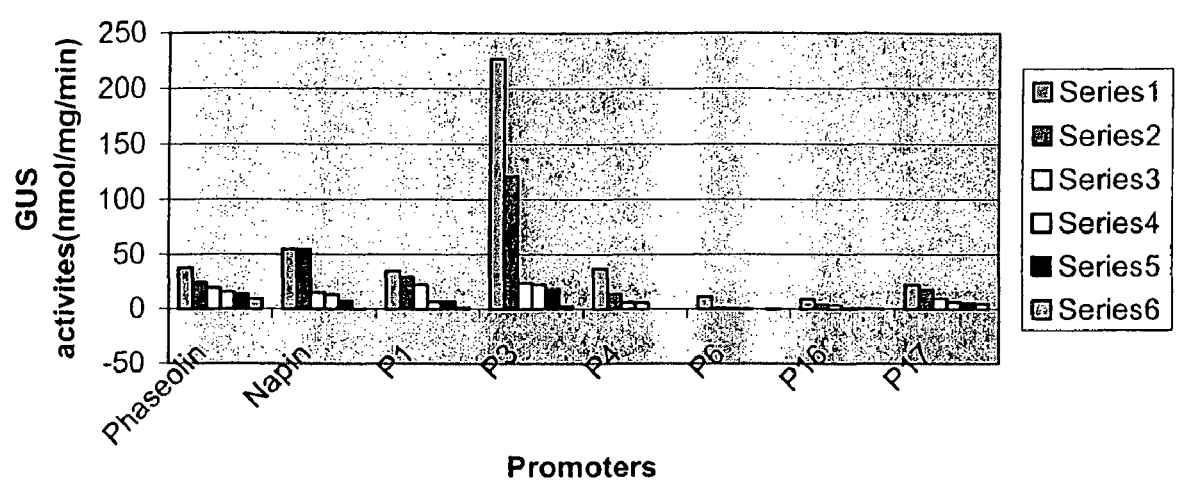
FIG. 20 shows a comparison of the GUS activities of different promoters. Seeds were harvested at 16 DAP. The extracts prepared from the harvested seeds were used for GUS and protein assays. For each promoter-GUS construct, six transgenic lines were selected for analysis. The results are listed in decreasing order of GUS activity.

Six independent transformants from each promoter construct of the six promoters resulting in highest GUS activity, P1, P3, P4, P6, P16 and P17, were selected for further quantitative analysis. The GUS activities of the six lines at 16 DAF are shown in order from high to low activity, and compared to the activities observed with the napin and phaseolin promoter controls, in FIG. 20. As can be seen from the results, the promoters P1, P3, P4 and P17 result in GUS activities which are comparable to those observed for the napin and phaseolin promoter controls. The promoter P3, which is annotated as the promoter of a storage protein gene (see Table 2 in FIG. 18), has stronger activity than the other promoters P1, P4, P6, P16 and P17 and than the napin or phaseolin controls.

J. Tissue-Specificity of Expression Pattern of Different Promoter Regions

Figure 21:
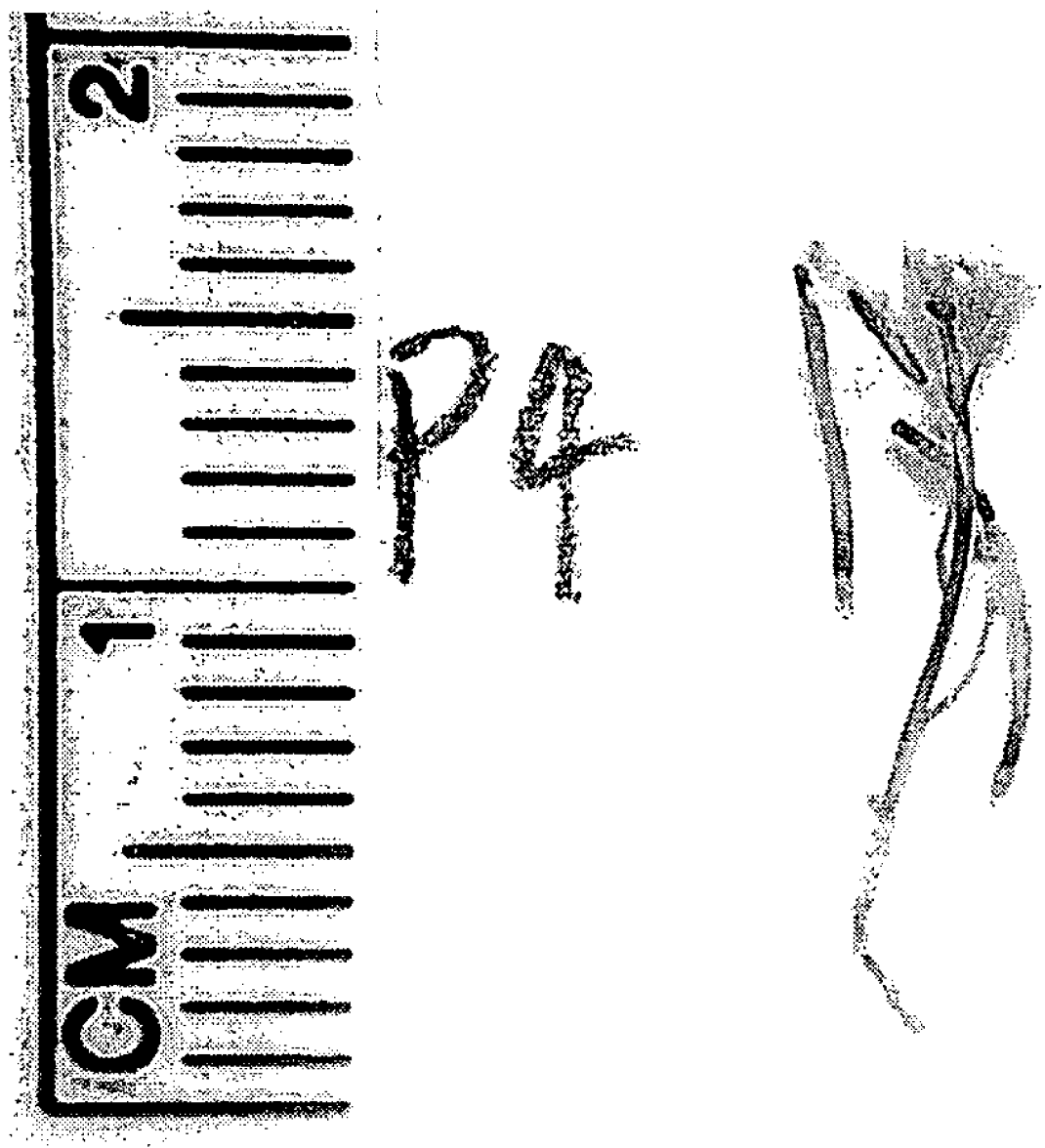
FIG. 21 shows the expression of GUS from the P4 construct in floral tissue.

The pattern of expression of the six best seed promoter constructs was examined by plants transformed with the promoter-GUS constructs, where the promoters were one of the six promoters P1, P3, P4, P6, P16 and P17, or a napin or phaseolin promoter. The localization of by GUS expression sites in the transgenic plants was determined by GUS histochemical staining of young seedlings, roots, primordial tissue, floral tissue, vascular tissue, maturing leaves, and siliques. All of the transgenic plants had GUS activities in the cotyledon and hypocotyl of young seedlings. This is thought to be caused by the residue of GUS in the seed. Interestingly, promoter P4 results in GUS activity in the floral tissues and young siliques (FIG. 21). In addition, GUS activity was detected in the anther and pollen tissues of plants transformed with the phaseolin construct.

K. Timing of GUS Expression During Seed Development.

Figure 22:
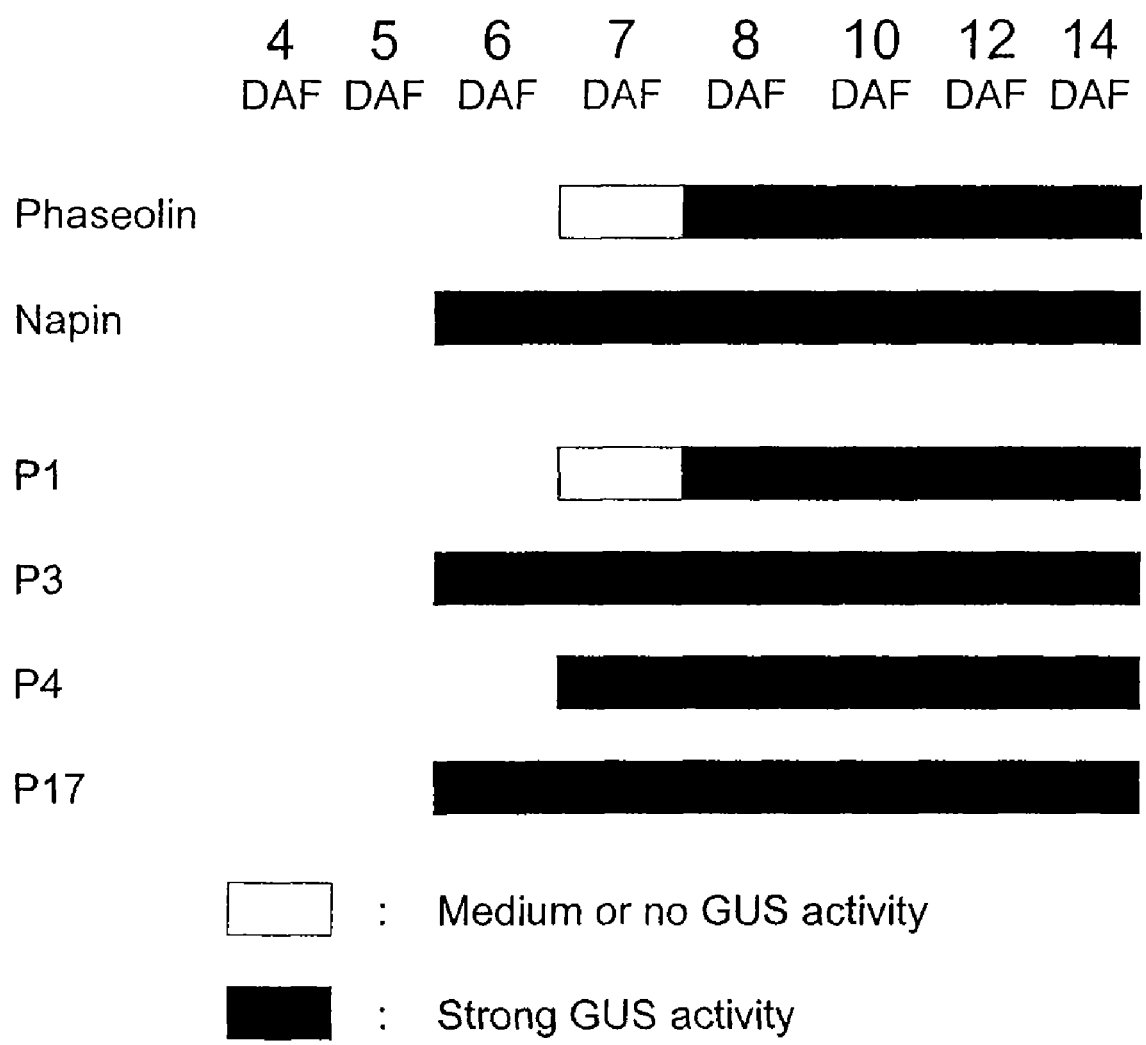
FIG. 22 shows the expression pattern of six promoters. Seeds at 4, 5, 6, 7, 8, 10, 12, 14 DAP were removed from siliques for GUS histochemical staining. The staining was done at 37° C. for 16 h

The timing of expression of the candidate promoters at different embryo stages was also examined. Embryos were collected for GUS histochemical staining analysis at 4, 5, 6, 7, 8, 9, 10, 12, 14 DAF. The GUS activities from the promoters P6 and P16 were not high enough for reliable observation, so they were excluded from this analysis. The GUS expression profiles are shown in FIG. 22. These expression profiles show that all the promoters start to express in mid or mid-late embryo stage. Moreover, the napin, P3, and P17 promoters result in GUS expression about 1 or 2 days earlier than do the phaseolin, P1, and P4 promoters.

L. Effects of Copy Number and Chromosomal Position on Promoter Activity

Two different aspects of plant transformation might affect the level of activity observed from the different promoters. These two aspects are artifacts of plant transformation, and include the copy number of a transgene in a plant, and the position of insertion of the transgene into the chromosome. Therefore, the effects of these different aspects were examined.

The effect of copy number on promoter activity was examined first. The correlation analysis of the copy number (data not shown) and GUS activity is shown in Table 3. For plants transformed with the control phaseolin-GUS constructs, the analyzed plants did not appear to possess multiple copies. For six of the promoters of the present invention P1, P3, P4, P6, P16, and P17, and the control promoter napin, copy number did not appear to have an obvious correlation with GUS activity (as evidenced by the observation that r0.05=0.754 (DF=5)), although for three promoters P1, P4 and P16, there appeared to be a slight positive correlation.

The effect of chromosomal position on promoter activity was then examined. This was measured by the ratio of standard deviation value of GUS activities to the mean value of GUS activities for every promoter, also as shown in Table 3.

The results indicate that for the promoters of the present invention, P3, P4, P6 and P16, the standard deviation values were higher than the mean values. For the other two promoters of the present invention, P1 and P17, and the two control promoters, the ratios were also equal to or higher than 0.50. This means that in different transgenic lines obtained with the same construct, the levels of GUS activities in the transformed plants varied considerably. This may be due to different chromosomal positions of the insertion of the T-DNA.

Taken together, these results suggest that in these experiments, position effect, rather than copy number, may play an important role in the levels of the observed activities for seed-specific promoters.

TABLE 3

Analysis the effect of copy number and insert position

| Promoter | Correlation coefficient | MEAN | STDEV | STDEV/Mean |
|---|---|---|---|---|
| Phaseolin | — | 20.13 | 10.03 | 0.50 |
| Napin | 0.16 | 24.40 | 24.20 | 0.99 |
| P1 | 0.62 | 16.93 | 13.78 | 0.81 |
| P3 | −0.26 | 69.35 | 88.08 | 1.27 |
| P4 | 0.67 | 10.48 | 14.01 | 1.34 |
| P6 | −0.24 | 2.21 | 4.48 | 2.03 |
| P16 | 0.71 | 3.18 | 3.24 | 1.02 |
| P17 | 0.03 | 11.38 | 7.28 | 0.64 | r 0.05 = 0.754
Correlation coefficient: correlation coefficient between GUS activity and copy number; MEAN: mean value of GUS activities; STDV: standard deviation value of GUS activities; '—': no correlation.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method of producing a product of interest in a plant seed, comprising:
   a) providing a transgenic plant comprising a nucleic acid sequence encoding the product of interest, said nucleic acid sequence operably linked to a promoter region comprising a seed-specific promoter, said promoter region selected from the group consisting of SEQ ID NOs:1 and 11 and variants thereof that are at least 95% identical to SEQ ID NOs:1 or 11; and
   b) growing the plant under conditions such that the product is produced in a seed of the plant.

2. A method of producing a protein of interest in a plant seed, comprising:
   a) providing a transgenic plant comprising a nucleic acid sequence encoding the protein of interest operably linked to a promoter region comprising a seed-specific promoter, said promoter region selected from the group consisting of SEQ ID NOs:1 and 11 and variants thereof that are at least 95% identical to SEQ ID NOs:1 or 11; and
   b) growing the plant under conditions such that the protein is produced in a seed of the plant.

3. A method of expressing a nucleic acid sequence of interest in a plant seed, comprising:
   a) providing a transgenic plant comprising said nucleic acid sequence operably linked to a promoter region comprising a seed-specific promoter, said promoter region selected from the group consisting of SEQ ID NOs: 1 and 11 and variants thereof that are at least 95% identical to SEQ ID NOs:1 or 11; and
   b) growing the plant under conditions such that the nucleic acid sequence is expressed in a seed of the plant.

4. An isolated DNA molecule comprising (A) a plant promoter region, said promoter region comprising a seed-specific promoter, said promoter region selected from the group consisting of SEQ ID NOs:1 and 11 and variants thereof that are at least 95% identical to SEQ ID NOs:1 or 11, and (B) a heterologous gene operably linked to the plant promoter.

5. The DNA molecule of claim 1, further comprising a termination sequence.

6. An expression vector, comprising the DNA molecule of claim 4.

7. A transgenic plant cell, comprising the DNA molecule of claim 4.

8. A transgenic plant, comprising the DNA molecule of claim 4.

9. A transgenic seed, comprising the DNA molecule of claim 4.

* * * * *

SEQUENCE LISTING

<160> NUMBER OF SEQ ID NOS: 63

<210> SEQ ID NO 1
<211> LENGTH: 1158
<212> TYPE: DNA
<213> ORGANISM: Arabidopsis thaliana

<400> SEQUENCE: 1

```
cacaaacata cactcaaaat ccagactcac atctactcaa ttatgcaact tcatcatgaa      60
aacatcaaaa acagtcaaag taacaaaatc aagtcagatt cagcacacaa agccagtaaa     120
gatagaaaat ttaacgaacg ctcatgctaa gctgcgcaaa atacttccta atcaaaacag     180
taacaacgag taattagcaa aatccgagca gaaaactctc acccacctcc gaaattcacg     240
tcttcactaa aattttcgaa aggaatcgat caataccaac ccattacaca aaatacataa     300
tcaaaatggc gagaatcgta cctggaaact ttgcttcaag tcgcagagag aggaaaagga     360
agatcgtgga gaaaggggtt tagggtttaa gctcagactt ctattggagt aaatgggacg     420
gtgtcacatt ttccgttttg gaaatgaact ttgggctcac gttatgggct attagatatt     480
tgatgggctt tctagtaaat acaatataag ttattgggct tagtttaaat aagcccatgt     540
tggaaatatt tgacacatgt cttggctact agtgctaaac atgcaaccga acagttgtcg     600
agacaagtcg cagcatatac aatggatcaa acacgcctag tgtcgccgcg tctcgctcat     660
gtgtcacctt gtttcctcgt tttttttaa tttttcataa gttcttttgt tttatcttca     720
atacaaattt ttggctgtat cttgcaaact cttcgatcat atcgccaata tacgtgaaca     780
ctggtgatct aatttgttgt gttaattgtt aaatttagat tctattctcc ggtttaaaag     840
tgaattatat gtatcatggt taaaacattg taagtaagat gataataaaa tgataaattt     900
agttgatgga taacgtgaag caaaaaatga gatagataca tttgattttg tcgtattttg     960
acatatgcgg agagtgagct acgcgcatga agatcaagag acacttgctc gagctcacag    1020
agtgacgtgt aaaaagctta gactgaagtc cccatgcaaa cctaatccta cgtggctcaa    1080
```

```
accacgagct cacttgacaa tatataaact cctcctaagt cccgttctct tcatccatct    1140
ctcacaacaa acaaaaag                                                  1158

<210> SEQ ID NO 2
<211> LENGTH: 1148
<212> TYPE: DNA
<213> ORGANISM: Arabidopsis thaliana

<400> SEQUENCE: 2
caagagtgta aaacgtaccg atcaaatgtc tttataaaaa aaacgtgttg atgttgttct      60
gtgaatacaa ttagttctgg ttaacagctg gtcgaccatt ttctgatgag aatttatgta     120
aggccattgc tctggtgttg agaaggttta gtttggttca agctaaccgt ggttagaaag     180
ttagaatata atgtgtttct tgatcagtga tatcgatcgg atttgtatta ttcatattgt     240
ttactctttg agtaattcat agtggtaact cttttttttt tttttttttt ttcatattgg     300
taactctttg aaatgaaaaa catagctaag aattgctagc tttgatttag tcgagacgta     360
cgaactctcg attttggttt ttgatttgtt ggtgtaaaac tctcgatatt cataactcgt     420
aagattttgt acgtatcatc ttcttattct cttcatcgct ctgttttcaa ttttatgtca     480
aaacatggtt ttggtaattt cttttactcc tacttcacgg tttgagttat aattttttg      540 gtaaacccctt aaccacgagt tttgatgtat tttgacacct ctaattatgt gtgtatacgt    600
acacatataa ttcggtattt tcttaacata tatatccctc ataaaaattt cttacatgca    660
ttgttcgtga gtgaccccgtt aatatatata ttgatagata ctcttataaa attatattct   720
aaatttcaga ttaagctggc acaactatat ttccaacatc actagctacc atcaaaagat    780
tgacttctca tcttactcga ttgaaaccaa attaacatag ggttttttatt taaataaaag   840 tttaaccttc ttttaaaaaa attgttcata gtgtcatgtc agaacaagag ctacaaatca    900
cacatagcat gcataagcgg agctatgatg agtggtattg ttttgttcgt cacttgtcac    960
tcttttccaa cacataatcc cgacaacaac gtaagagcat ctctctctct ccacacacac   1020
tcatgcatgc atgcattctt acacgtgatt gccatgcaaa tctcctttct cacctataaa   1080
tacaaaccaa cccttcacta cactcttcac tcaaaccaaa acaagaaaac atacacaaat   1140
agcaaaac                                                             1148

<210> SEQ ID NO 3
<211> LENGTH: 1032
<212> TYPE: DNA
<213> ORGANISM: Arabidopsis thaliana

<400> SEQUENCE: 3
caaaccattg tttacacgtc aatttgaatt gcgtcaaata ttcgactgga atcctacaac      60
atatttcttc tattatatca ataggaagca acgaacgttc acatgaagcc atgcaaaaac     120
aaattgagaa aaaaaatcag aaaatttatg acaagtggtc ttgcttctta tactacgtcg     180
tgaatggatg gtaataaaca attaaatgtt acctctagtt tttttttttt gagagaatgg     240
tttttatccg tatatggctt attacaagtt tcctcctttt tcgagtttgg tttgaggtct     300
atattgaaga tgagatacta aaaattgagg taaattcttt agtgtgaagg aaaattagta     360
aatacgatac gtttggaatt gtttactact aaaaaaaaaa ttgttttaga ccaagccagt     420
ccgacaaaaa ggcgtgtgaa tcataagaag tatcacatga tgctagacat aaaagatttt     480
tcaaacatga caaaacaaat tgtgagtgtc ttagtcatgc catttgaagt agaacgaaac    540
ttagtgatga gacacgtaac atcagtgaga atcaagatct aacttcggac ttatcgtacg    600
```

| | | | | |
|---|---|---|---|---|
| taccacgtcc | acctaagtgt | tatccatatc | tactacatgt | ctatcttcat tcaatttttt | 660 |
| ttttgcatta | acttgtaaac | atagtgcata | ataattagaa | tcaagatttg aatccaattc | 720 |
| gcttactaaa | tcctaaatgt | taaaagcata | catgttttc | aaatcctact tttaggtgct | 780 |
| aagttttttt | tctaaggtag | ttagagattg | ttagatttta | tatcattgaa ctgatcatca | 840 |
| gtctctatac | taacttctag | atctcattga | atgtttactc | aatttttttt aatttttgt | 900 |
| ttggataatc | gtctgctcgt | ggttttgatg | cgtacgaaca | ctcgtcacca tgcatgtcaa | 960 |
| gctctccttc | ctatataaac | taaaaccacc | cattattgtc | ctcaaaaaca aacacatcaa | 1020 |
| caaaacaaca | ag | | | | 1032 |

<210> SEQ ID NO 4
<211> LENGTH: 1409
<212> TYPE: DNA
<213> ORGANISM: Arabidopsis thaliana

<400> SEQUENCE: 4

| | | | | | |
|---|---|---|---|---|---|
| ctaaacgagt | aaagtttagc | acgattgaga | ccacactgac | ccatagcagt ccaatgagct | 60 |
| acggaaggcc | tagggcttga | ggcttgatga | gcgcgtggtg | gaatagcgtt tgaatctaaa | 120 |
| gttcggtttg | gtacgacttg | taatatgaaa | taataatgta | caagaagtt ctacgcttaa | 180 |
| gggaactgtt | ttgttttgag | ctttgtatta | ggacgtctag | tgtacaacaa cgaacgtcgt | 240 |
| gtataagcga | tcgttgactc | tgcacatgta | actcttttcct | gaataaaaaa tctttaagtc | 300 |
| tttaatttct | acatctttta | ggattatata | aacgttacta | tataaataaa aaagaaaaaa | 360 |
| aaatcagttc | actaacatgc | gagactttgg | gctaaatata | gtgattccaa agaaaatgag | 420 |
| ttataatatt | aattaatata | aagctcatt | tctttggaat | atcgttataa gaatatttta | 480 |
| acttggatat | aactgggctt | acgccatttg | catctcgagg | atttttgtt tttgttttg | 540 |
| ttttttaat | acattctcgc | acttacacac | taaaaatcat | aatgatcttc ttaattcttt | 600 |
| agcggaacca | ccaattaatc | tttttattaa | gaactttatt | acttatttca cttatttgtg | 660 |
| catacgtgca | ttatttgc | agtaacaaat | atcgcgttat | atatactgaa atccggacgc | 720 |
| attaataata | gggatatgat | tatatgaacc | actatctagc | tttggtagaa acccaattat | 780 |
| aatcaaataa | tttaccatta | ttgaataaat | taggctatat | aagttcatta atagatgcta | 840 |
| taggttttc | ttacaaggca | cacatttgat | tgttattttc | tttcatatac actgaatgta | 900 |
| catgtgtaca | cttggcatac | atggcaagat | tatgtgttac | aatatagact gtgccattgc | 960 |
| catgcaatgt | gactcctgtg | gccatttcta | tcacaatgtg | tcaatcttgg agtatccgtt | 1020 |
| gtttatcctc | taatttactg | attaatttat | gaacatgtat | aattatttat atcatatgat | 1080 |
| ctcgtaagat | atcttagcat | tttccaccat | atgttattag | taaatcatct agatggattg | 1140 |
| atgtaaatag | gaaagttaaa | ttaacacacc | aaaaagtaa | ctgattaaaa gcatacaact | 1200 |
| taatattcag | attatggtaa | ctaaatcagt | ctcatgcaaa | ctccaaaaaa ttatacgagt | 1260 |
| cacaactctt | gattttttc | cggttaaaca | aaatacatat | tttcatttgt atgcaaccag | 1320 |
| aataaaacac | taactatctc | ctttaaatac | cattttccct | acgagtctac gacgctctct | 1380 |
| aaacttctta | tacaaaacaa | aacacaccc | | | 1409 |

<210> SEQ ID NO 5
<211> LENGTH: 1112
<212> TYPE: DNA
<213> ORGANISM: Arabidopsis thaliana

```
<400> SEQUENCE: 5
gatccgaaaa gtagagtttc gtggatctga taattggaga agagagaacg agctgaaacc     60
ctaaattcgg ataaagtctg caacttctgt tgtttcggtg gcgagaacaa aaataatgag    120
aggaagagga aaatatcgtc gttttgtct cacagtctct ttagcagctt ttctttagat    180
atttatttta ttttttccat ggatagagag agctaggcat tccggttatt tggagatttt    240
ggaatttcaa ttttgcggtt tggtatttta ttttattta tcaatttgaa cgaaacagag    300
ctttgttttg gttacgatgc ggtggatttt ggttcggttt agagtgatat atatttggta    360
ccaaattaaa ccaagattcg ttttcggtaa aaacaaaatt tgattttaa gcatttttgg    420
aaaaattagt gttatatata tgagatttct taatcaaaat ctcacttttaa tccgatttag    480
tggtagttca taaagtggtt tcatgtatat gatacctgaa taaccaacat atgtatttta    540
agagacactt ggaataataa ttctaaatat cctaactact cgtgtccgta tgttttgtca    600
cggtgaaacg tgagaggact agttttgtc acccgtccat aacattctta gacatacatt    660
acttttgggag tgaaaaacat taagcttatc tttatccata tattgtctta ccatcaatag    720
acaatatcca atggaccggt gacctgcgtg tataagtaat ttttcaagat gctaaaactt    780
ttatgtattt cagaattaac ctccaaaaac atttattgac acactactac tctttccgta    840
ttgactctca actagtcatt tcaaaataat tgacatgtca gaacatgagt tacacatggt    900
tgcatattgc aagtagacgc ggaaacttgt cacttccttt acattttgagt ttccaacacc    960
taatcacgac aacaatcata tagctctcgc atacaaacaa acatatgcat gtattcttac   1020
acgtgaactc catgcaagtc tcttttctca cctataaata ccaaccacac cttcaccaca   1080
ttcttcactc gaaccaaaac atacacacat ag                                 1112

<210> SEQ ID NO 6
<211> LENGTH: 975
<212> TYPE: DNA
<213> ORGANISM: Arabidopsis thaliana

<400> SEQUENCE: 6
tcagaaagag aagtgagcta cctgcagtgt cctctgtttt gtcgatgaag gattttttaga    60
ttggtatgtg atgaagtaca acgagctgat gcctgcgttg atggctatct tcaccaaaag   120
tcgtgtttgt tatgaagcac aacgagctgg tgcctacgtt gatggctata ttcaccaaag   180
gtcgtgtttc atagatcaga aggcacacct acaacaatga gcagtgccaa ggtttgttct   240
tattttgttg ttgtcagttt tagatttcta gatgaatctt atgatgtgat aatgaaaaaa   300
cgaaagaaaa gcttttgtta aagtatctat gagtgatatc atgatatgtc aaaaatgttg   360
catggataca ttgattcttt agtacttgtt acgagctgct aagagagtcg tgtcaagttc   420
atactttttc cttgtcattt aacataattg cttgtctgtt tggattctat tgtgcggaag   480
ttatgattta tattttcaga ttcatatttt caattaggaa gctttagttg gaatcaaagt   540
ggatgaccct gattgaggat tttaatgatc gttgtgagaa cctttcttgt agttagttgg   600
tggattgtaa aaaaattata tgtatttaac tcttgattga gagtcagaag ttggaaaaat   660
gaattaagag gttttcgaat aagagatcac agttatagta tagtattaat tggatatcac   720
aatctattca taatattagc tagttagata aaattgtgtt tgatcttggc aagaggtgtt   780
aaaatagtat catgttgaca tgttggtatg actattagtc gtaatttaag cttatgtata   840
tttcttgtaa gaaatgttca tgtatcataa taaatacaag tgtatcgagt ttttgtatat   900
atagaggtct atgatttggg aagaagaaca caacataact caccacaaac acaatctaat   960
```
ccaaaaaatc aaaag 975

<210> SEQ ID NO 7
<211> LENGTH: 1117
<212> TYPE: DNA
<213> ORGANISM: Arabidopsis thaliana

<400> SEQUENCE: 7

| | | |
|---|---|---|
| tgacacgcaa caaccaaagc caaaagggtg cgttaccatt aattcaggga aagcgaaata | 60 |
| aacccaaatc tctcttctaa cgaagtaaca actcacccac ttctcacatt gattcactcc | 120 |
| tttccagttt ttacatatag ccttcgttca tcaatcacct taagcaaatt gcaatcacaa | 180 |
| aaaaaaaaaa gtacagtact tagcaaaatt ttaagttttt gttatttcca cggcaactta | 240 |
| gcaaatatgc accacatatt gacattagct aatatacaac acatgttttt ttagaaatgt | 300 |
| acaagcatta acaatatcc aacacaaaat gacatgatcg tagatgatta agataattcg | 360 |
| atccctataa ctaatagttt ccaaaacttc tgctgacttt tctctcgaca gcgatggtaa | 420 |
| gaagaaggta caagttttg aagcccgaat ataacaaaag gacagaaagc ttttagtttt | 480 |
| ctagataaga tcttagcttt ggtcacgtaa aaaaaattaa aagtgaattg gttaacaata | 540 |
| taggagtact ttgtatccaa aggtcattgc aataaataaa cacttaagta ctctgtagtc | 600 |
| acacatctct aggagcttaa tattggataa tcgcttgtag acttgtatta aaatatttag | 660 |
| taggtcaaat ccctatcttc tacagtttct actctcgtcc gtacagacta cagacactat | 720 |
| gctatagttt tgtgttgaat tctacaaagt acaaattctt ctttcggtgc caataacaaa | 780 |
| taaacacaat tctcaaatta catttgtcta aattttatt tgattcggta taaatgtaac | 840 |
| gctatgttgg gaatcatatg ataaatccag attaagactt cttatttaat ttattttgt | 900 |
| atatataaaa tataatatcc aaccataaag ttttttacc gatcgatgat aatgtgaatc | 960 |
| caaatatttt aacaggatga taaataattg atgtggcttt tataaccgca gcaattctgg | 1020 |
| cgtgactctc tccgcagcat ttattttct ctctataaat taaaaacatt acttactctt | 1080 |
| tctctcttcc acttaactca tatcaacctt cgccgga | 1117 |

<210> SEQ ID NO 8
<211> LENGTH: 1048
<212> TYPE: DNA
<213> ORGANISM: Arabidopsis thaliana

<400> SEQUENCE: 8

| | | |
|---|---|---|
| atctctgcaa atcaaacctt attattaagc tacatttaca tagtgtcctt ataattctca | 60 |
| tgacatagca acattattaa acgacaactt tctagcttca tttaaaatgg aaaatcacat | 120 |
| aacactcaca ttaactatac taacataaca ctcacattac cgactagcat ataaatggat | 180 |
| attgatataa caataatccc ccaaatttat gtctattttg ttcattatgc aaatgtccca | 240 |
| aaatgatata tcttggaaag tactaaccgg agacgagggt cgaggtatag aagtgatttg | 300 |
| gtcgaaccga aatgaggaac ccgggtttgg acaccaggag cattttggta atcatccaaa | 360 |
| tcagggtcat agtacaacat cattcgatcg ctgaagcacc tggtgaaggg agacaataac | 420 |
| actgctgcat cgaaccatag cctaaaccat ccaccactct tcttatgaat cggatataac | 480 |
| cagctgctac accagacact acttggcttg tattctctgt ccagccgtac ctctagctgg | 540 |
| ttacctccgt ttcctggaac cagaatcaaa gggtacacgt tgctacccac agcttgacac | 600 |
| atcgaggtca tcgtcaccac aacgagtatc gctatgacta ccgaataatg tgaagatatt | 660 |

| | |
|---|---|
| tttttcattt tcgttctaag aaacagactc tcatggtcat ggatctatgc agaaagctgg | 720 |
| agatttgaag aaaaaggtcc attgaatttg aaaaacagag tagtatctta aaacgtaagg | 780 |
| cttaagataa gtagtatatg gtggatatgg aacccgcgta atcatctaga ggctctacaa | 840 |
| atatttattt tgtatttcct tcttattttg tatttgccta cgtggcatta tacaacgtat | 900 |
| ttaacttgaa accagattta tggcccaatg ggtcgggtcg acccgaccga ttttaaactg | 960 |
| cgctcctaac taaaaaaaag tcaaaaccct ttgaaaaacc taaaaacgca atttgcttcg | 1020 |
| tcgtctctca tctctttctc tttctccg | 1048 |

<210> SEQ ID NO 9
<211> LENGTH: 1069
<212> TYPE: DNA
<213> ORGANISM: Arabidopsis thaliana

<400> SEQUENCE: 9

| | |
|---|---|
| gtaagtcgtt ctctaatctt ccatgccaat ttgctcggtt aaaaccagac tggttggact | 60 |
| gaaaaatcgg ttttaattaa ttgagttgtg cttatgaggt ctattggttt attttaaaa | 120 |
| tcctttgtag attaggagag taccaacaag agcgaaagac atcactaaac acgaagagtg | 180 |
| aaagtggaaa aagagaacta tcaagacttg actcgaagac cggattgtac ccggatgatt | 240 |
| cgaaacaggg cggtgctggt gctggtgctg gtggttggct ttcttgttgt ctctgttttt | 300 |
| cggtgaaaaa ttgaggttat tactctttgt catgtcaatt atttaggtca tagctgtcca | 360 |
| agagacgcga gacattagac aaggtaatta ccgattgtat cctatatatt cctatgtaac | 420 |
| gaaattcaga tactacgtaa tcttaatgtg tcgatggaat gaaaaaataa agtattctgt | 480 |
| aaatattttc tatatattat ttagcatata tacgctttat aaattataaa tttggtccct | 540 |
| cccaaataca tgaaaacaat gtagtgataa aaaaaaaaca aattctgtat atatgctatt | 600 |
| tttataacat aacaagcatt tttcttagtc ggttaaaatt tcaagtgttt aatactttta | 660 |
| tataattatg aacgtaagtt ataatttatg ttttttttgg tcagtccatt attgattatt | 720 |
| ccattcacac tatatgcaac ctatattctt cctatgaaac ttttgatcgt gtgttaaata | 780 |
| ataatacaaa tttgatttca tctaataggt gggtggggac tctctaatta cgttctttga | 840 |
| catctactca tcaacatttg gctaatcttt ctaaggaat tccatctacc ggtcattttt | 900 |
| gtttaaatgc tctcttgtaa ctaaaagtcc gtaccaaact tgtgtaattt cattaaacat | 960 |
| taattattta gtccattcca tgtcaaatat gacttatatg ctcttgtcct ataaatttta | 1020 |
| aagcaatgag gattcaccaa gtatacatgc ataacaaatt aagagcgag | 1069 |

<210> SEQ ID NO 10
<211> LENGTH: 1044
<212> TYPE: DNA
<213> ORGANISM: Arabidopsis thaliana

<400> SEQUENCE: 10

| | |
|---|---|
| gtgagaaaat tcatgagcac tcttagaaat gtaaatagtt tgatttgaag aaatgtggtt | 60 |
| tttaagaaga taattgcaaa actcagaaag gatttcacaa aaaacaattc gtgaaatctt | 120 |
| tcctgaattt cgtaaaatcc tttctaaatt ttagaaaatt attatttgaa tgattttacg | 180 |
| aaatttcgga aagaatctat aaaattcagg aaagatatca taaaatttat gaagagttat | 240 |
| acacaacaaa aagaaatttt tgaatttcat gaaatccttc gtaattgctt acattccttc | 300 |
| ctaaattttg taaaattctt cctggatttt cttttgcgag aaaatagggg catatatttt | 360 |
| ttacgggaaa ttttttgacg aaaacttatt ttggcggaaa aaattgtcag gaattttttgg | 420 |

| | |
|---|---|
| taatgaatat gtgtattttt ttaattgtta attttaataa taaaataaaa tagttatctg | 480 |
| aatgttattt atgtcaaaaa aaaatatgaa tgctatttt gtcttaaaaa cttaaaattg | 540 |
| tactatttga aggaatttca ttttatttta ttaatgtgat tagatttata attaaatata | 600 |
| attaaatgat tgtaaatact aacttaaatt cttatttata aacataaagt aatatttaat | 660 |
| tttctttaat taaaaataca tattttattt tcataattta ttttgctttt ttttttttt | 720 |
| agttttgatt tattttaaaa catataatat gagtatatga ctatatgaca tagcatattg | 780 |
| gtttatttg attagataga aaagagacg ggtgaataaa agggtttaat actatggtga | 840 |
| acccaagtat atatcgtcca taacaaaaac actatataat tgaggtttgt agattgtgca | 900 |
| aacacgtgtg ggcatatcag cttgtaggat tgccacatac attatcatga gaagcttcca | 960 |
| ccagaataaa gcaaacaaa aaactccgaa agcggagaga acaaggaaaa ctgaaaaacc | 1020 |
| attgtgaagt atagtccttg atgc | 1044 |

<210> SEQ ID NO 11
<211> LENGTH: 1141
<212> TYPE: DNA
<213> ORGANISM: Arabidopsis thaliana

<400> SEQUENCE: 11

| | |
|---|---|
| caaacgaggc tccaaattca tattcggcct gcatactttt gccctggccc ggtttttttt | 60 |
| tttcttttt tcggtgtttc ataatacatc agcttccata actggagcaa ccgttataga | 120 |
| aagacatgta taagaacccc aaaaaaacag gtacgtcaaa agaggaaatt ctcataacat | 180 |
| acacaatatg ctcctaatca gccatcgtgt tgtgctgatc tcctaggtga cattatgtat | 240 |
| atctgtttga tatttcttta acacaacatg ttatcagtta cccatcaaaa cgtagtcagc | 300 |
| ttgaggtctt ccaaaaaaat ccacactaga ccttccttca tcacttcaac agacttcaaa | 360 |
| cttctatccc aaaaggaaaa aactaaataa gttgaaagga atggtcgaag catggggag | 420 |
| acacctaata cggcagctag actaatccgg tggattgata agcaaactcg aaacactctt | 480 |
| tcctctatca gattattggg ggataggaga tatgacaaaa gactgcaaat gtggtttgct | 540 |
| tctagaagtt aagagcttcc gggattttgt ttttattttt ttcagtgttg taacaaattt | 600 |
| aaattctgtc gcacttgtcg taacaacgat attttttctt tgaatataat ttaacattaa | 660 |
| attaaaaga aaaactaaat aaattatttt gaagttaata tattatgtta ttatctttgg | 720 |
| tttgcaataa atagatcgag tcaaggtcgt tatatgacca ttgtttagtt acgacgctac | 780 |
| ttcatacttg gaatctaagg agaaaaaatg taacatagtt ctcagtactt aatcacatag | 840 |
| ttctcagttc ttaatcactt tattgttaaa acttttcatc gaataattaa tgatttgatc | 900 |
| tccaatctca attaattata tatttctaaa gccaaaagag ataatgaaag gagaggtggt | 960 |
| agaaagaaaa cgttaatgta tcaaactcta ataaaagaaa ctgcgtgtat agacacgaag | 1020 |
| gctccgatct tttgcatgtc tcgcacgtgt cgtcctcttt cttcctactt aacacatata | 1080 |
| tgcatgcacc cttcttagaa aagtagcaaa acattgtgaa tcatcggaga gagtgggaaa | 1140 |
| c | 1141 |

<210> SEQ ID NO 12
<211> LENGTH: 1292
<212> TYPE: DNA
<213> ORGANISM: Arabidopsis thaliana

<400> SEQUENCE: 12

```
caccaagcct atacaaacat aatttaacgc cgcctagttt tgtttattct gcacgtaaca    60
tataaagcta acagatatgc gacaaaatat ctataaatta catatataag tatatataat   120
ataagaatgt tggatgtata tattagtagt ttaatcaatg aaaatatatc tttatatctt   180
tattaaaaaa actaaaaatg tatctttata tacatttcgt agtttaaaat caaaattcaa   240
gatagagcga aaatgatttt ttttttttta aatgaaccaa aagtacaaca ttcctacctt   300
tatttttaat aactcgttta tattcgccaa tcagacacac acatagactt ttaaaatagt   360
aaaagtaact tagccgatta tttatgtaaa atattcgtat aaaatttta ttaacaaata    420 tatttgattt ctcatcttat aacctgttta ttgatcagat tacacgaaaa aataactaaa   480
cagataaatt tactcgaact gcatacaata gagatgtatt tgtgcatgag tgtagcccaa   540
aaatgtgtaa ggaaataaca cccattggta ggccgagaca tgcctgtacc atggccgctg   600
aaatagtaga agaaccaaat acctaccaaa gtactcttaa gctaacgttg acatgattta   660
attagattaa cgattgagta aacgacaaat tagcgctttc gttttatatt aaagacgcac   720
gatatttaaa tggcaactat acattaaaat tatataaaat ataactat aaccaatttg     780 ataaatgaga aaaatgtacg atatgtcgta ccactccatc ctgactatga cttatggagg   840
aagtcaatgc ttatcaacta cttgcttatc aatatcctat ttatcactat cagttttct    900 cttttctata catatattat ttcctataga tcatgttggt cataatgtaa tcaacttaaa   960
atttaagatc tactagtttg tgttgaagta taactgtata agcctaaatt cgaacgttag  1020
tctgacttaa tagttaattc cattttgttt tgggtaaatg tttcagtttc actgctgttt  1080
ggaaaatctt tggacagata ttgagattgg gcttataata tttattattg ggccttaatt  1140
taagagccct tttataggca gatacaaaaa cgacggcgtt taactcatcc gctcagcgac  1200
ttccacatag ccgttaaaac gatgataata aacccaatcc ggttcatctc caacagaaga  1260
acgtaataac tgatgcttgt cttcaagtca ac                                1292

<210> SEQ ID NO 13
<211> LENGTH: 1164
<212> TYPE: DNA
<213> ORGANISM: Arabidopsis thaliana

<400> SEQUENCE: 13
cacaaacata cactcaaaat ccagactcac atctactcaa ttatgcaact tcatcatgaa    60
aacatcaaaa acagtcaaag taacaaaatc aagtcagatt cagcacacaa agccagtaaa   120
gatagaaaat ttaacgaacg ctcatgctaa gctgcgcaaa atacttccta atcaaaacag   180
taacaacgag taattagcaa aatccgagca gaaaactctc acccacctcc gaaattcacg   240
tcttcactaa aattttcgaa aggaatcgat caataccaac ccattacaca aaatacataa   300
tcaaaatggc gagaatcgta cctggaaaact ttgcttcaag tcgcagagag aggaaaagga   360
agatcgtgga gaaggggtt tagggtttaa gctcagactt ctattggagt aaatgggacg    420
gtgtcacatt ttccgttttg gaaatgaact ttgggctcac gttatgggct attagatatt   480
tgatgggctt tctagtaaat acaatataag ttattgggct tagtttaaat aagcccatgt   540
tggaaatatt tgacacatgt cttggctact agtgctaaac atgcaaccga acagttgtcg   600
agacaagtcg cagcatatac aatggatcaa acacgcctag tgtcgccgcg tctcgctcat   660
gtgtcacctt gtttcctcgt ttttttttaa ttttcataa gttcttttgt tttatcttca    720
atacaaattt ttggctgtat cttgcaaact cttcgatcat atcgccaata tacgtgaaca   780
ctggtgatct aatttgttgt gttaattgtt aaatttagat tctattctcc ggtttaaaag   840
```

```
tgaattatat gtatcatggt taaaacattg taagtaagat gataataaaa tgataaattt    900
agttgatgga taacgtgaag caaaaaatga gatagataca tttgattttg tcgtattttg    960
acatatgcgg agagtgagct acgcgcatga agatcaagag acacttgctc gagctcacag   1020
agtgacgtgt aaaaagctta gactgaagtc cccatgcaaa cctaatccta cgtggctcaa   1080
accacgagct cacttgacaa tatataaact cctcctaagt cccgttctct tcatccatct   1140
ctcacaacaa acaaaaagaa aatg                                          1164

<210> SEQ ID NO 14
<211> LENGTH: 1155
<212> TYPE: DNA
<213> ORGANISM: Arabidopsis thaliana

<400> SEQUENCE: 14
caagagtgta aaacgtaccg atcaaatgtc tttataaaaa aaacgtgttg atgttgttct     60
gtgaatacaa ttagttctgg ttaacagctg gtcgaccatt ttctgatgag aatttatgta    120
aggccattgc tctggtgttg agaaggttta gtttggttca agctaaccgt ggttagaaag    180
ttagaatata atgtgtttct tgatcagtga tatcgatcgg atttgtatta ttcatattgt    240
ttactctttg agtaattcat agtggtaact cttttttttt tttttttttt ttcatattgg    300
taactctttg aaatgaaaaa catagctaag aattgctagc tttgatttag tcgagacgta    360
cgaactctcg attttggttt ttgatttgtt ggtgtaaaac tctcgatatt cataactcgt    420
aagattttgt acgtatcatc ttcttattct cttcatcgct ctgttttcaa ttttatgtca    480
aaacatggtt ttggtaattt cttttactcc tacttcacgg tttgagttat aattttttg     540 gtaaaccctt aaccacgagt tttgatgtat tttgacacct ctaattatgt gtgtatacgt    600
acacatataa ttcggtattt tcttaacata tatatccctc ataaaaattt cttacatgca    660
ttgttcgtga gtgacccgtt aatatatata ttgatagata ctcttataaa attatattct    720
aaatttcaga ttaagctggc acaactatat ttccaacatc actagctacc atcaaaagat    780
tgacttctca tcttactcga ttgaaaccaa attaacatag ggttttttatt taaataaaag    840 tttaaccttc tttttaaaaa attgttcata gtgtcatgtc agaacaagag ctacaaatca    900
cacatagcat gcataagcgg agctatgatg agtggtattg ttttgttcgt cacttgtcac    960
tcttttccaa cacataatcc cgacaacaac gtaagagcat ctctctctct ccacacacac   1020
tcatgcatgc atgcattctt acacgtgatt gccatgcaaa tctcctttct cacctataaa   1080
tacaaaccaa cccttcacta cactcttcac tcaaaccaaa acaagaaaac atacacaaat   1140
agcaaaacat ggcta                                                    1155

<210> SEQ ID NO 15
<211> LENGTH: 1040
<212> TYPE: DNA
<213> ORGANISM: Arabidopsis thaliana

<400> SEQUENCE: 15
caaaccattg tttcacacgtc aatttgaatt gcgtcaaata ttcgactgga atcctacaac    60
atatttcttc tattatatca ataggaagca acgaacgttc acatgaagcc atgcaaaaac   120
aaattgagaa aaaaaatcag aaaatttatg acaagtggtc ttgcttctta tactacgtcg   180
tgaatggatg gtaataaaca attaaatgtt acctctagtt ttttttttttt gagagaatgg   240 ttttttatccg tatatggctt attacaagtt tcctcctttt tcgagtttgg tttgaggtct   300
```

| atattgaaga tgagatacta aaaattgagg taaattcttt agtgtgaagg aaaattagta | 360 |
| aatacgatac gtttggaatt gtttactact aaaaaaaaaa ttgttttaga ccaagccagt | 420 |
| ccgacaaaaa ggcgtgtgaa tcataagaag tatcacatga tgctagacat aaaagatttt | 480 |
| tcaaacatga caaaacaaat tgtgagtgtc ttagtcatgc catttgaagt agaacgaaac | 540 |
| ttagtgatga gacacgtaac atcagtgaga atcaagatct aacttcggac ttatcgtacg | 600 |
| taccacgtcc acctaagtgt tatccatatc tactacatgt ctatcttcat tcaattttt | 660 |
| ttttgcatta acttgtaaac atagtgcata ataattagaa tcaagatttg aatccaattc | 720 |
| gcttactaaa tcctaaatgt taaaagcata catgttttc aaatcctact tttaggtgct | 780 |
| aagttttttt tctaaggtag ttagagattg ttagatttta tatcattgaa ctgatcatca | 840 |
| gtctctatac taacttctag atctcattga atgtttactc aattttttt aattttttgt | 900 |
| ttggataatc gtctgctcgt ggttttgatg cgtacgaaca ctcgtcacca tgcatgtcaa | 960 |
| gctctccttc ctatataaac taaaaccacc cattattgtc ctcaaaaaca aacacatcaa | 1020 |
| caaaacaaca agaaaaaatg | 1040 |

```
<210> SEQ ID NO 16
<211> LENGTH: 1416
<212> TYPE: DNA
<213> ORGANISM: Arabidopsis thaliana

<400> SEQUENCE: 16
```

| ctaaacgagt aaagtttagc acgattgaga ccacactgac ccatagcagt ccaatgagct | 60 |
| acggaaggcc tagggcttga ggcttgatga gcgcgtggtg aatagcgtt tgaatctaaa | 120 |
| gttcggtttg gtacgacttg taatatgaaa taataatgta caagaagtt ctacgcttaa | 180 |
| gggaactgtt ttgttttgag cttgtatta ggacgtctag tgtacaacaa cgaacgtcgt | 240 |
| gtataagcga tcgttgactc tgcacatgta actctttcct gaataaaaaa tctttaagtc | 300 |
| tttaatttct acatctttta ggattatata aacgttacta tataaataaa aagaaaaaa | 360 |
| aaatcagttc actaacatgc gagactttgg gctaaatata gtgattccaa agaaaatgag | 420 |
| ttataatatt aattaatata aagctcattt tctttggaat atcgttataa gaatatttta | 480 |
| acttggatat aactgggctt acgccatttg catctcgagg attttttgtt tttgttttg | 540 |
| ttttttttaat acattctcgc acttacacac taaaaatcat aatgatcttc ttaattcttt | 600 |
| agcggaacca ccaattaatc ttttttattaa gaactttatt acttatttca cttatttgtg | 660 |
| catacgtgca ttatttggc agtaacaaat atcgcgttat atatactgaa atccggacgc | 720 |
| attaataata gggatatgat tatatgaacc actatctagc tttggtagaa acccaattat | 780 |
| aatcaaataa tttaccatta ttgaataaat taggctatat aagttcatta atagatgcta | 840 |
| taggtttttc ttacaaggca cacatttgat tgttattttc tttcatatac actgaatgta | 900 |
| catgtgtaca cttggcatac atggcaagat tatgtgttac aatatagact gtgccattgc | 960 |
| catgcaatgt gactcctgtg gccattcta tcacaatgtg tcaatcttgg agtatccgtt | 1020 |
| gtttatcctc taatttactg attaatttat gaacatgtat aattatttat atcatatgat | 1080 |
| ctcgtaagat atcttagcat tttccaccat atgttattag taaatcatct agatggattg | 1140 |
| atgtaaatag gaaagttaaa ttaacacacc aaaaagtaa ctgattaaaa gcatacaact | 1200 |
| taatattcag attatggtaa ctaaatcagt ctcatgcaaa ctccaaaaaa ttatacgagt | 1260 |
| cacaactctt gatttttttc cggttaaaca aaatacatat tttcatttgt atgcaaccag | 1320 |
| aataaaacac taactatctc ctttaaatac cattttccct acgagtctac gacgctctct | 1380 |

```
aaacttctta tacaaaacaa aacacaccca aatatg                              1416

<210> SEQ ID NO 17
<211> LENGTH: 1121
<212> TYPE: DNA
<213> ORGANISM: Arabidopsis thaliana

<400> SEQUENCE: 17
gatccgaaaa gtagagtttc gtggatctga taattggaga agagagaacg agctgaaacc      60
ctaaattcgg ataaagtctg caacttctgt tgtttcggtg gcgagaacaa aaataatgag     120
aggaagagga aaatatcgtc gttttgtct cacagtctct ttagcagctt ttctttagat      180
atttatttta ttttttccat ggatagagag agctaggcat tccggttatt tggagatttt     240
ggaatttcaa ttttgcggtt tggtatttta ttttattta tcaatttgaa cgaaacagag      300
ctttgttttg gttacgatgc ggtggatttt ggttcggttt agagtgatat atatttggta     360
ccaaattaaa ccaagattcg ttttcggtaa aaacaaaatt tgattttaa gcatttttgg      420 aaaaattagt gttatatata tgagattct taatcaaaat ctcacttta tccgatttag       480 tggtagttca taaagtggtt tcatgtatat gatacctgaa taaccaacat atgtatttta     540
agagacactt ggaataataa ttctaaatat cctaactact cgtgtccgta tgttttgtca     600
cggtgaaacg tgagaggact agttttttgtc acccgtccat aacattctta gacatacatt    660
actttgggag tgaaaaacat taagcttatc tttatccata tattgtctta ccatcaatag     720
acaatatcca atggaccggt gacctgcgtg tataagtaat ttttcaagat gctaaaactt    780
ttatgtattt cagaattaac ctccaaaaac atttattgac acactactac tcttccgta    840 ttgactctca actagtcatt tcaaaataat tgacatgtca gaacatgagt tacacatggt   900
tgcatattgc aagtagacgc ggaaacttgt cacttccttt acatttgagt ttccaacacc   960
taatcacgac aacaatcata tagctctcgc atacaaacaa acatatgcat gtattcttac  1020
acgtgaactc catgcaagtc tcttttctca cctataaata ccaaccacac cttcaccaca  1080
ttcttcactc gaaccaaaac atacacacat agcaaaaaat g                       1121

<210> SEQ ID NO 18
<211> LENGTH: 981
<212> TYPE: DNA
<213> ORGANISM: Arabidopsis thaliana

<400> SEQUENCE: 18
tcagaaagag aagtgagcta cctgcagtgt cctctgtttt gtcgatgaag gattttaga      60 ttggtatgtg atgaagtaca acgagctgat gcctgcgttg atggctatct tcaccaaaag    120
tcgtgtttgt tatgaagcac aacgagctgg tgcctacgtt gatggctata ttcaccaaag    180
gtcgtgtttc atagatcaga aggcacacct acaacaatga gcagtgccaa ggttgttct    240 tattttgttg ttgtcagttt tagatttcta gatgaatctt atgatgtgat aatggaaaaa    300
cgaaagaaaa gcttttgtta aagtatctat gagtgatatc atgatatgtc aaaaatgttg   360
catggataca ttgattcttt agtacttgtt acgagctgct aagagagtcg tgtcaagttc   420 aatactttc cttgtcattt aacataattg cttgtctgtt tggattctat tgtgcggaag    480
ttatgattta tattttcaga ttcatatttt caattaggaa gctttagttg gaatcaaagt   540
ggatgaccct gattgaggat tttaatgatc gttgtgagaa ccttttcttgt agttagttgg  600 tggattgtaa aaaaattata tgtatttaac tcttgattga gagtcagaag ttggaaaaat   660
```

```
gaattaagag gttttcgaat aagagatcac agttatagta tagtattaat tggatatcac      720
aatctattca taatattagc tagttagata aaattgtgtt tgatcttggc aagaggtgtt      780
aaaatagtat catgttgaca tgttggtatg actattagtc gtaatttaag cttatgtata      840
tttcttgtaa gaatgttca tgtatcataa taaatacaag tgtatcgagt ttttgtatat       900
atagaggtct atgatttggg aagaagaaca caacataact caccacaaac acaatctaat      960
ccaaaaaatc aaaagatgaa t                                                981
```

<210> SEQ ID NO 19
<211> LENGTH: 1124
<212> TYPE: DNA
<213> ORGANISM: Arabidopsis thaliana

<400> SEQUENCE: 19

```
tgacacgcaa caccaaagc caaaggggtg cgttaccatt aattcaggga aagcgaaata       60
aacccaaatc tctcttctaa cgaagtaaca actcacccac ttctcacatt gattcactcc     120
tttccagttt ttacatatag ccttcgttca tcaatcacct taagcaaatt gcaatcacaa     180
aaaaaaaaaa gtacagtact tagcaaaatt ttaagttttt gttatttcca cggcaactta     240
gcaaatatgc accacatatt gacattagct aatatacaac acatgttttt ttagaaatgt     300
acaagcatta acaaatatcc aacacaaaat gacatgatcg tagatgatta agataattcg     360
atccctataa ctaatagttt ccaaaacttc tgctgacttt tctctcgaca gcgatggtaa     420
gaagaaggta caaagttttg aagcccgaat ataacaaaag gacagaaagc ttttagtttt     480
ctagataaga tcttagcttt ggtcacgtaa aaaaaattaa aagtgaattg gttaacaata     540
taggagtact ttgtatccaa aggtcattgc aataaataaa cacttaagta ctctgtagtc     600
acacatctct aggagcttaa tattggataa tcgcttgtag acttgtatta aaatatttag     660
taggtcaaat ccctatcttc tacagtttct actctcgtcc gtacagacta cagacactat     720
gctatagttt tgtgttgaat tctacaaagt acaaattctt ctttcggtgc caataacaaa     780
taaacacaat tctcaaatta catttgtcta aatttttatt tgattcggta taaatgtaac     840
gctatgttgg gaatcatatg ataaatccag attaagactt cttatttaat ttattttgt     900 atatataaaa tataatatcc aaccataaag ttttttttacc gatcgatgat aatgtgaatc     960
caaatatttt aacaggatga taaataattg atgtggcttt ataaccgca gcaattctgg     1020 cgtgactctc tccgcagcat ttatttttct ctctataaat taaaaacatt acttactctt     1080
tctctcttcc acttaactca tatcaacctt cgccggaaat aatg                     1124
```

<210> SEQ ID NO 20
<211> LENGTH: 1059
<212> TYPE: DNA
<213> ORGANISM: Arabidopsis thaliana

<400> SEQUENCE: 20

```
atctctgcaa atcaaacctt attattaagc tacatttaca tagtgtcctt ataattctca      60
tgacatagca acattattaa acgacaactt tctagcttca tttaaaatgg aaaatcacat     120
aacactcaca ttaactatac taacataaca ctcacattac cgactagcat ataaatggat     180
attgatataa caataatccc ccaaatttat gtctattttg ttcattatgc aaatgtccca     240
aaatgatata tcttggaaag tactaaccgg agacgagggt cgaggtatag aagtgatttg     300
gtcgaaccga aatgaggaac ccgggtttgg acaccaggag cattttggta atcatccaaa     360
tcagggtcat agtacaacat cattcgatcg ctgaagcacc tggtgaaggg agacaataac     420
```

```
actgctgcat cgaaccatag cctaaaccat ccaccactct tcttatgaat cggatataac    480
cagctgctac accagacact acttggcttg tattctctgt ccagccgtac ctctagctgg    540
ttacctccgt ttcctggaac cagaatcaaa gggtacacgt tgctacccac agcttgacac    600
atcgaggtca tcgtcaccac aacgagtatc gctatgacta ccgaataatg tgaagatatt    660
tttttcattt tcgttctaag aaacagactc tcatggtcat ggatctatgc agaaagctgg    720
agatttgaag aaaaaggtcc attgaatttg aaaaacagag tagtatctta aaacgtaagg    780
cttaagataa gtagtatatg gtggatatgg aacccgcgta atcatctaga ggctctacaa    840
atatttattt tgtatttcct tcttattttg tatttgccta cgtggcatta taacgtat     900 ttaacttgaa accagattta tggcccaatg ggtcgggtcg acccgaccga ttttaaactg    960
cgctcctaac taaaaaaaag tcaaacccct tgaaaaacc taaaaacgca atttgcttcg    1020
tcgtctctca tctctttctc tttctccgtc gccaccatg                          1059

<210> SEQ ID NO 21
<211> LENGTH: 1077
<212> TYPE: DNA
<213> ORGANISM: Arabidopsis thaliana

<400> SEQUENCE: 21
gtaagtcgtt ctctaatctt ccatgccaat ttgctcggtt aaaaccagac tggttggact     60
gaaaaatcgg ttttaattaa ttgagttgtg cttatgaggt ctattggttt attttttaaaa   120 tcctttgtag attaggagag taccaacaag agcgaaagac atcactaaac acgaagagtg    180
aaagtggaaa aagagaacta tcaagacttg actcgaagac cggattgtac ccggatgatt    240
cgaaacaggg cggtgctggt gctggtgctg gtggttggct tcttgttgt ctctgttttt     300 cggtgaaaaa ttgaggttat tactcttttgt catgtcaatt atttaggtca tagctgtcca   360
agagacgcga gacattagac aaggtaatta ccgattgtat cctatatatt cctatgtaac    420
gaaattcaga tactacgtaa tcttaatgtg tcgatggaat gaaaaaataa agtattctgt    480
aaatattttc tatatattat ttagcatata tacgctttat aaattataaa tttggtccct    540
cccaaataca tgaaaacaat gtagtgataa aaaaaaaaca aattctgtat atatgctatt    600
tttataacat aacaagcatt tttcttagtc ggttaaaatt tcaagtgttt aatacttttta  660 tataattatg aacgtaagtt ataatttatg ttttttttgg tcagtccatt attgattatt    720
ccattcacac tatatgcaac ctatattctt cctatgaaac ttttgatcgt gtgttaaata    780
ataatacaaa tttgatttca tctaataggt gggtggggac tctctaatta cgttctttga    840
catctactca tcaacatttg gctaatcttt ctaaaggaat tccatctacc ggtcattttt    900
gtttaaatgc tctcttgtaa ctaaaagtcc gtaccaaact tgtgtaattt cattaaacat    960
taattattta gtccattcca tgtcaaatat gacttatatg ctcttgtcct ataaattta   1020 aagcaatgag gattcaccaa gtatacatgc ataacaaatt aagagcgagc aataatg     1077

<210> SEQ ID NO 22
<211> LENGTH: 1051
<212> TYPE: DNA
<213> ORGANISM: Arabidopsis thaliana

<400> SEQUENCE: 22
gtgagaaaat tcatgagcac tcttagaaat gtaaatagtt tgatttgaag aaatgtggtt     60
tttaagaaga taattgcaaa actcagaaag gatttcacaa aaaacaattc gtgaaatctt    120
```

```
tcctgaattt cgtaaaatcc tttctaaatt ttagaaaatt attatttgaa tgattttacg      180
aaatttcgga aagaatctat aaaattcagg aaagatatca taaaatttat gaagagttat      240
acacaacaaa aagaaatttt tgaatttcat gaaatccttc gtaattgctt acattccttc      300
ctaaattttg taaaattctt cctggatttt cttttgcgag aaaatagggg catatatttt      360
ttacgggaaa ttttttgacg aaaacttatt ttggcggaaa aaattgtcag gaattttttgg     420 taatgaatat gtgtattttt ttaattgtta attttaataa taaaataaaa tagttatctg      480 aatgttatt atgtcaaaaa aaatatgaa tgctattttt gtcttaaaaa cttaaaattg        540
tactatttga aggaatttca ttttattta ttaatgtgat tagatttata attaaatata       600
attaaatgat tgtaaatact aacttaaatt cttatttata aacataaagt aatatttaat      660
tttctttaat taaaaataca tattttattt tcataattta ttttgctttt ttttttttt       720 agttttgatt tattttaaaa catataatat gagtatatga ctatatgaca tagcatattg      780
gtttattttg attagataga aaagagacg ggtgaataaa agggtttaat actatggtga       840
acccaagtat atatcgtcca taacaaaaac actatataat tgaggtttgt agattgtgca      900
aacacgtgtg ggcatatcag cttgtaggat tgccacatac attatcatga gaagcttcca      960
ccagaataaa gcaaaacaaa aaactccgaa agcggagaga acaaggaaaa ctgaaaaacc     1020
attgtgaagt atagtccttg atgcatggat t                                    1051

<210> SEQ ID NO 23
<211> LENGTH: 1148
<212> TYPE: DNA
<213> ORGANISM: Arabidopsis thaliana

<400> SEQUENCE: 23
caaacgaggc tccaaattca tattcggcct gcatactttt gccctggccc ggttttttt       60 tttctttttt tcggtgtttc ataatacatc agcttccata actggagcaa ccgttataga     120
aagacatgta taagaacccc aaaaaaacag gtacgtcaaa agaggaaatt ctcataacat     180
acacaatatg ctcctaatca gccatcgtgt tgtgctgatc tcctaggtga cattatgtat     240
atctgtttga tatttcttta acacaacatg ttatcagtta cccatcaaaa cgtagtcagc     300
ttgaggtctt ccaaaaaaat ccacactaga ccttccttca tcacttcaac agacttcaaa     360
cttctatccc aaaaggaaaa aactaaataa gttgaaagga atggtcgaag gcatggggag     420
acacctaata cggcagctag actaatccgg tggattgata agcaaactcg aaacactctt     480
tcctctatca gattattggg ggataggaga tatgacaaaa gactgcaaat gtggtttgct     540
tctagaagtt aagagcttcc gggatttttgt tttttatttt ttcagtgttg taacaaattt     600
aaattctgtc gcacttgtcg taacaacgat attttttctt tgaatataat ttaacattaa     660
attaaaaaga aaactaaat aaattatttt gaagttaata tattatgtta ttatctttgg      720
tttgcaataa atagatcgag tcaaggtcgt tatatgacca ttgtttagtt acgacgctac     780
ttcatacttg gaatctaagg agaaaaaatg taacatagtt ctcagtactt aatcacatag     840
ttctcagttc ttaatcactt tattgttaaa acttttcatc gaataattaa tgatttgatc     900
tccaatctca attaattata tatttctaaa gccaaaagag ataatgaaag gagaggtggt     960
agaaagaaaa cgttaatgta tcaaactcta ataaagaaa ctgcgtgtat agacacgaag     1020
gctccgatct tttgcatgtc tcgcacgtgt cgtcctcttt cttcctactt aacacatata    1080
tgcatgcacc cttcttagaa aagtagcaaa acattgtgaa tcatcggaga gagtgggaaa    1140
catggaga                                                             1148
```

<210> SEQ ID NO 24
<211> LENGTH: 1300
<212> TYPE: DNA
<213> ORGANISM: Arabidopsis thaliana

<400> SEQUENCE: 24

```
caccaagcct atacaaacat aatttaacgc cgcctagttt tgtttattct gcacgtaaca    60
tataaagcta acagatatgc gacaaaatat ctataaatta catatataag tatatataat   120
ataagaatgt tggatgtata tattagtagt ttaatcaatg aaaatatatc tttatatctt   180
tattaaaaaa actaaaaatg tatctttata tacatttcgt agtttaaaat caaaattcaa   240
gatagagcga aaatgatttt ttttttttta aatgaaccaa aagtacaaca ttcctacctt   300
tattttttaat aactcgttta tattcgccaa tcagacacac acatagactt ttaaaatagt   360
aaaagtaact tagccgatta tttatgtaaa atattcgtat aaaattttta ttaacaaata   420
tatttgattt ctcatcttat aacctgttta ttgatcagat tacacgaaaa aataactaaa   480
cagataaatt tactcgaact gcatacaata gagatgtatt tgtgcatgag tgtagcccaa   540
aaatgtgtaa ggaaataaca cccattggta ggccgagaca tgcctgtacc atggccgctg   600
aaatagtaga agaaccaaat acctaccaaa gtactcttaa gctaacgttg acatgattta   660
attagattaa cgattgagta aacgacaaat tagcgctttc gttttatatt aaagacgcac   720
gatatttaaa tggcaactat acattaaaat tatataaaat atataactat aaccaatttg   780
ataaatgaga aaaatgtacg atatgtcgta ccactccatc ctgactatga cttatggagg   840
aagtcaatgc ttatcaacta cttgcttatc aatatcctat ttatcactat cagttttttct   900
cttttctata catatattat ttcctataga tcatgttggt cataatgtaa tcaacttaaa   960
atttaagatc tactagtttg tgttgaagta taactgtata agcctaaatt cgaacgttag  1020
tctgacttaa tagttaattc cattttgttt tgggtaaatg tttcagttc actgctgttt  1080
ggaaaatctt tggacagata ttgagattgg gcttataata tttattattg ggccttaatt  1140
taagagccct tttataggca gatacaaaaa cgacggcgtt taactcatcc gctcagcgac  1200
ttccacatag ccgttaaaac gatgataata aacccaatcc ggttcatctc caacagaaga  1260
acgtaataac tgatgcttgt cttcaagtca accatggagt                        1300
```

<210> SEQ ID NO 25
<211> LENGTH: 1433
<212> TYPE: DNA
<213> ORGANISM: Arabidopsis thaliana

<400> SEQUENCE: 25

```
gatctctccc gaagaagcta aacgagtaaa gtttagcacg attgagacca cactgaccca    60
tagcagtcca atgagctacg gaaggcctag ggcttgaggc ttgatgagcg cgtggtggaa   120
tagcgtttga atctaaagtt cggtttggta cgacttgtaa tatgaaataa taatgtacaa   180
agaagttcta cgcttaaggg aactgttttg ttttgagctt tgtattagga cgtctagtgt   240
acaacaacga acgtcgtgta taagcgatcg ttgactctgc acatgtaact ctttcctgaa   300
taaaaaatct ttaagtcttt aatttctaca tcttttagga ttatataaac gttactatat   360
aaataaaaaa gaaaaaaaaa tcagttcact aacatgcgag actttgggct aaatatagtg   420
attccaaaga aaatgagtta taatattaat taatataaag ctcatttttct ttggaatatc   480
gttataagaa tatttttaact tggatataac tgggcttacg ccatttgcat ctcgaggatt   540
```

```
ttttgttttt gttttttgttt ttttaataca ttctcgcact tacacactaa aaatcataat        600
gatcttctta attctttagc ggaaccacca attaatcttt ttattaagaa ctttattact        660
tatttcactt atttgtgcat acgtgcatta ttttggcagt aacaaatatc gcgttatata        720
tactgaaatc cggacgcatt aataataggg atatgattat atgaaccact atctagcttt        780
ggtagaaacc caattataat caaataattt accattattg aataaattag gctatataag        840
ttcattaata gatgctatag gttttcttta caaggcacac atttgattgt tattttcttt        900
catatacact gaatgtacat gtgtacactt ggcatacatg gcaagattat gtgttacaat        960
atagactgtg ccattgccat gcaatgtgac tcctgtggcc atttctatca caatgtgtca       1020
atcttggagt atccgttgtt tatcctctaa tttactgatt aatttatgaa catgtataat       1080
tatttatatc atatgatctc gtaagatatc ttagcatttt ccaccatatg ttattagtaa       1140
atcatctaga tggattgatg taaataggaa agttaaatta acacaccaaa aaagtaactg       1200
attaaaagca tacaacttaa tattcagatt atggtaacta aatcagtctc atgcaaactc       1260
caaaaaatta tacgagtcac aactcttgat ttttttccgg ttaaacaaaa tacatatttt       1320
catttgtatg caaccagaat aaaacactaa ctatctcctt taaataccat tttccctacg       1380
agtctacgac gctctctaaa cttcttatac aaaacaaaac acacccaaat atg             1433
```

<210> SEQ ID NO 26
<211> LENGTH: 57
<212> TYPE: DNA
<213> ORGANISM: Arabidopsis thaliana

<400> SEQUENCE: 26

```
attccaaaga aaatgagtta taatattaat taatataaag ctcatttttct ttggaat          57
```

<210> SEQ ID NO 27
<211> LENGTH: 1080
<212> TYPE: DNA
<213> ORGANISM: Arabidopsis thaliana

<400> SEQUENCE: 27

```
catctctgca aatcaaacct tattattaag ctacatttac atagtgtcct tataattctc         60
atgacatagc aacattatta aacgacaact ttctagcttc atttaaaatg gaaaatcaca        120
taacactcac attaactata ctaacataac actcacatta ccgactagca tataaatgga        180
tattgatata acaataatcc cccaaattta tgtctatttt gttcattatg caaatgtccc        240
aaaatgatat atcttggaaa gtactaaccg gagacgaggg tcgaggtata gaagtgattt        300
ggtcgaaccg aaatgaggaa cccgggtttg gacaccagga gcattttggt aatcatccaa        360
atcagggtca tagtacaaca tcattcgatc gctgaagcac ctggtgaagg gagacaataa        420
cactgctgca tcgaaccata gcctaaacca tccaccactc ttcttatgaa tcggatataa        480
ccagctgcta caccagacac tacttggctt gtattctctg tccagccgta cctctagctg        540
gttacctccg tttcctggaa ccagaatcaa agggtacacg ttgctaccca gcttgaca         600
catcgaggtc atcgtcacca caacgagtat cgctatgact accgaataat gtgaagatat        660
ttttttcatt ttcgttctaa gaaacagact ctcatggtca tggatctatg cagaaagctg        720
gagatttgaa gaaaaggtc cattgaattt gaaaaacaga gtagtatctt aaaacgtaag        780
gcttaagata agtagtatat ggtggatatg gaacccgcgt aatcatctag aggctctaca        840
aatatttatt ttgtatttcc ttcttatttt gtatttgcct acgtggcatt atacaacgta        900
tttaacttga aaccagattt atggcccaat gggtcgggtc gacccgaccg atttaaact       960
```

```
gcgctcctaa ctaaaaaaaa gtcaaaaccc tttgaaaaac ctaaaaacgc aatttgcttc   1020
gtcgtctctc atctctttct ctttctccgt cgccaccatg tttgagtacc ggtgcagctc   1080
```

<210> SEQ ID NO 28
<211> LENGTH: 26
<212> TYPE: DNA
<213> ORGANISM: Arabidopsis thaliana

<400> SEQUENCE: 28

```
aatgggtcgg gtcgacccga ccgatt                                         26
```

<210> SEQ ID NO 29
<211> LENGTH: 1140
<212> TYPE: DNA
<213> ORGANISM: Arabidopsis thaliana

<400> SEQUENCE: 29

```
agggactagg aacttaagaa aaacaaagtc atcaaaaaaa caaaaaaaaa gttgtgagaa     60
aattcatgag cactcttaga aatgtaaata gtttgatttg aagaaatgtg gttttttaaga   120 agataattgc aaaactcaga aaggatttca caaaaaacaa ttcgtgaaat ctttcctgaa   180
tttcgtaaaa tccttttctaa atttttagaaa attattattt gaatgatttt acgaaatttc   240
ggaaagaatc tataaaattc aggaaagata tcataaaatt tatgaagagt tatacacaac   300
aaaaagaaat ttttgaattt catgaaatcc ttcgtaattg cttacattcc ttcctaaatt   360
ttgtaaaatt cttcctggat tttcttttgc gagaaaatag gggcatatat tttttacggg   420
aaattttttg acgaaaactt atttttggcgg aaaaaaattgt caggaatttt tggtaatgaa   480
tatgtgtatt tttttaattg ttaattttaa taataaaata aatagttat ctgaatgtta   540 tttatgtcaa aaaaaaaatat gaatgctatt tttgtcttaa aaacttaaaa ttgtactatt   600
tgaaggaatt tcatttttatt ttattaatgt gattagattt ataattaaat ataattaaat   660
gattgtaaat actaacttaa attcttattt ataaacataa agtaatattt aattttcttt   720
aattaaaaat acatattttta ttttcataat ttatttttgct tttttttttt tttagttttg   780
atttattttt aaacatataa tatgagtata tgactatatg acatagcata ttggtttatt   840
ttgattagat agaaaagag acgggtgaat aaaagggttt aatactatgg tgaacccaag   900
tatatatcgt ccataacaaa aacactatat aattgaggtt tgtagattgt gcaaacacgt   960
gtgggcatat cagcttgtag gattgccaca tacattatca tgagaagctt ccaccagaat  1020
aaagcaaaac aaaaaactcc gaaagcggag agaacaagga aaactgaaaa accattgtga  1080
agtatagtcc ttgatgcatg gattcaatca acaagatcat caacttcttg tttcctctct  1140
```

<210> SEQ ID NO 30
<211> LENGTH: 109
<212> TYPE: DNA
<213> ORGANISM: Arabidopsis thaliana

<400> SEQUENCE: 30

```
tgaaatcttt cctgaatttc gtaaaatcct ttctaaattt tagaaaatta ttatttgaat    60
gattttacga aatttcggaa agaatctata aaattcagga agatatca                109
```

<210> SEQ ID NO 31
<211> LENGTH: 32
<212> TYPE: DNA
<213> ORGANISM: Arabidopsis thaliana -continued

```
<400> SEQUENCE: 31
cactggatcc tttttgtttg ttgtgagaga tg                          32

<210> SEQ ID NO 32
<211> LENGTH: 30
<212> TYPE: DNA
<213> ORGANISM: Arabidopsis thaliana

<400> SEQUENCE: 32
cactgaattc acaaacatac actcaaaatc                             30

<210> SEQ ID NO 33
<211> LENGTH: 34
<212> TYPE: DNA
<213> ORGANISM: Arabidopsis thaliana

<400> SEQUENCE: 33
cactggatcc gttttgctat ttgtgtatgt tttc                        34

<210> SEQ ID NO 34
<211> LENGTH: 27
<212> TYPE: DNA
<213> ORGANISM: Arabidopsis thaliana

<400> SEQUENCE: 34
cactgaattc aagagtgtaa aacgtac                                27

<210> SEQ ID NO 35
<211> LENGTH: 31
<212> TYPE: DNA
<213> ORGANISM: Arabidopsis thaliana

<400> SEQUENCE: 35
cactggatcc ttgttgtttt gttgatgtgt t                           31

<210> SEQ ID NO 36
<211> LENGTH: 25
<212> TYPE: DNA
<213> ORGANISM: Arabidopsis thaliana

<400> SEQUENCE: 36
cactgaattc cattgtttac acgtc                                  25

<210> SEQ ID NO 37
<211> LENGTH: 33
<212> TYPE: DNA
<213> ORGANISM: Arabidopsis thaliana

<400> SEQUENCE: 37
cactggatcc gggtgtgttt tgttttgtat aag                         33

<210> SEQ ID NO 38
<211> LENGTH: 31
<212> TYPE: DNA
<213> ORGANISM: Arabidopsis thaliana

<400> SEQUENCE: 38
cactgaattc taaacgagta aagtttagca c                           31

<210> SEQ ID NO 39
<211> LENGTH: 31
<212> TYPE: DNA
<213> ORGANISM: Arabidopsis thaliana
```

<400> SEQUENCE: 39
cactggatcc tatgtgtgta tgttttggtt c                               31

<210> SEQ ID NO 40
<211> LENGTH: 30
<212> TYPE: DNA
<213> ORGANISM: Arabidopsis thaliana

<400> SEQUENCE: 40
cactgaattc gatccgaaaa gtagagtttc                                 30

<210> SEQ ID NO 41
<211> LENGTH: 43
<212> TYPE: DNA
<213> ORGANISM: Arabidopsis thaliana

<400> SEQUENCE: 41
cactggatcc ttttgatttt ttggattaga ttgtgtttgt ggt                  43

<210> SEQ ID NO 42
<211> LENGTH: 26
<212> TYPE: DNA
<213> ORGANISM: Arabidopsis thaliana

<400> SEQUENCE: 42
cactgaattc agaaagagaa gtgagc                                     26

<210> SEQ ID NO 43
<211> LENGTH: 27
<212> TYPE: DNA
<213> ORGANISM: Arabidopsis thaliana

<400> SEQUENCE: 43
cactggatcc ggcgaaggtt gatatga                                    27

<210> SEQ ID NO 44
<211> LENGTH: 28
<212> TYPE: DNA
<213> ORGANISM: Arabidopsis thaliana

<400> SEQUENCE: 44
cactcaattg acacgcaaca accaaagc                                   28

<210> SEQ ID NO 45
<211> LENGTH: 28
<212> TYPE: DNA
<213> ORGANISM: Arabidopsis thaliana

<400> SEQUENCE: 45
cactggatcc ggagaaagag aaagagat                                   28

<210> SEQ ID NO 46
<211> LENGTH: 28
<212> TYPE: DNA
<213> ORGANISM: Arabidopsis thaliana

<400> SEQUENCE: 46
cactgaattc atctctgcaa atcaaacc                                   28

<210> SEQ ID NO 47
<211> LENGTH: 30
<212> TYPE: DNA

<213> ORGANISM: Arabidopsis thaliana

<400> SEQUENCE: 47
cactggatcc tcgctcttaa tttgttatgc                                  30

<210> SEQ ID NO 48
<211> LENGTH: 30
<212> TYPE: DNA
<213> ORGANISM: Arabidopsis thaliana

<400> SEQUENCE: 48
cactcaattg taagtcgttc tctaatcttc                                  30

<210> SEQ ID NO 49
<211> LENGTH: 31
<212> TYPE: DNA
<213> ORGANISM: Arabidopsis thaliana

<400> SEQUENCE: 49
cactggatcc gcatcaagga ctatacttca c                                31

<210> SEQ ID NO 50
<211> LENGTH: 32
<212> TYPE: DNA
<213> ORGANISM: Arabidopsis thaliana

<400> SEQUENCE: 50
cactgaattc gtgagaaaat tcatgagcac tc                               32

<210> SEQ ID NO 51
<211> LENGTH: 26
<212> TYPE: DNA
<213> ORGANISM: Arabidopsis thaliana

<400> SEQUENCE: 51
cactggatcc gtttcccact ctctcc                                      26

<210> SEQ ID NO 52
<211> LENGTH: 28
<212> TYPE: DNA
<213> ORGANISM: Arabidopsis thaliana

<400> SEQUENCE: 52
cactgaattc aaacgaggct ccaaattc                                    28

<210> SEQ ID NO 53
<211> LENGTH: 28
<212> TYPE: DNA
<213> ORGANISM: Arabidopsis thaliana

<400> SEQUENCE: 53
cactggatcc gttgacttga agacaagc                                    28

<210> SEQ ID NO 54
<211> LENGTH: 27
<212> TYPE: DNA
<213> ORGANISM: Arabidopsis thaliana

<400> SEQUENCE: 54
cactgaattc accaagccta tacaaac                                     27

<210> SEQ ID NO 55
<211> LENGTH: 22

```
<212> TYPE: DNA
<213> ORGANISM: Arabidopsis thaliana

<400> SEQUENCE: 55
gtaatacgac tcactatagg gc                                           22

<210> SEQ ID NO 56
<211> LENGTH: 22
<212> TYPE: DNA
<213> ORGANISM: Arabidopsis thaliana

<400> SEQUENCE: 56
acaggaaaca gctatgacca tg                                           22

<210> SEQ ID NO 57
<211> LENGTH: 23
<212> TYPE: DNA
<213> ORGANISM: Arabidopsis thaliana

<400> SEQUENCE: 57
cccagtcacg acgttgtaaa acg                                          23

<210> SEQ ID NO 58
<211> LENGTH: 23
<212> TYPE: DNA
<213> ORGANISM: Arabidopsis thaliana

<400> SEQUENCE: 58
agcggataac aatttcacac agg                                          23

<210> SEQ ID NO 59
<211> LENGTH: 23
<212> TYPE: DNA
<213> ORGANISM: Arabidopsis thaliana

<400> SEQUENCE: 59
cgaagctttc ttcatcggtg att                                          23

<210> SEQ ID NO 60
<211> LENGTH: 22
<212> TYPE: DNA
<213> ORGANISM: Arabidopsis thaliana

<400> SEQUENCE: 60
ggtcggaatt cgtgtatgtt tt                                           22

<210> SEQ ID NO 61
<211> LENGTH: 57
<212> TYPE: DNA
<213> ORGANISM: Arabidopsis thaliana

<400> SEQUENCE: 61
attccaaaga aaatgagctt tatattaatt aatattataa ctcattttct ttggaat     57

<210> SEQ ID NO 62
<211> LENGTH: 26
<212> TYPE: DNA
<213> ORGANISM: Arabidopsis thaliana

<400> SEQUENCE: 62
aatcggtcgg gtcgacccga cccatt                                       26

<210> SEQ ID NO 63
```

```
<211> LENGTH: 109
<212> TYPE: DNA
<213> ORGANISM: Arabidopsis thaliana

<400> SEQUENCE: 63
tgatatcttt cctgaatttt atagattctt tccgaaattt cgtaaaatca ttcaaataat      60
aattttctaa aatttagaaa ggattttacg aaattcagga aagatttca                 109
```